United States Patent
Tsukamoto et al.

(10) Patent No.: US 6,740,777 B2
(45) Date of Patent: May 25, 2004

(54) THIOLALKYL BENZOIC ACID DERIVATIVES

(75) Inventors: Takashi Tsukamoto, Ellicott City, MD (US); Doris Stoermer, Baltimore, MD (US); Dilrukshi Vitharana, Towson, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 10/156,880

(22) Filed: May 30, 2002

(65) Prior Publication Data
US 2003/0100607 A1 May 29, 2003

Related U.S. Application Data
(60) Provisional application No. 60/342,746, filed on Dec. 28, 2001, and provisional application No. 60/294,036, filed on May 30, 2001.

(51) Int. Cl.$^7$ .............................................. C02C 321/00
(52) U.S. Cl. ........................................ 562/426; 514/317
(58) Field of Search ............................ 562/426; 514/317

(56) References Cited

U.S. PATENT DOCUMENTS

| | | | |
|---|---|---|---|
| 3,053,890 A | * | 9/1962 | Schatter |
| 5,089,388 A | | 2/1992 | Singh et al. |
| 5,204,358 A | | 4/1993 | Young et al. |
| 5,258,551 A | | 11/1993 | Murabayashi et al. |
| 5,314,918 A | | 5/1994 | Frazee et al. |
| 5,409,780 A | | 4/1995 | Schrier et al. |
| 5,453,502 A | | 9/1995 | Aikins et al. |
| 5,998,334 A | | 12/1999 | Murai et al. |
| 6,265,609 B1 | | 7/2001 | Jackson et al. |
| 2002/0019430 A1 | | 2/2002 | Jackson et al. |

FOREIGN PATENT DOCUMENTS

| | | |
|---|---|---|
| WO | WO 94/03835 | 12/1994 |
| WO | WO 98/42661 | 10/1998 |
| WO | WO 00/01668 A2 | 1/2000 |
| WO | WO 2001092274 * | 5/2001 |
| WO | WO 01/91738 A2 | 12/2001 |
| WO | WO 01/92273 A2 | 12/2001 |
| WO | WO 01/92274 A2 | 12/2001 |

OTHER PUBLICATIONS

Salteris, et al., "Ortho–directed lithiation of—omega, –phenoxyalkanethiols and N,N–dimethyl—omega—phenyoxyalkylamines," C.A. 131:243360.

Haj–Yehia, Abdullah, "Preparation of aromatic and heterocyclic nitrato derivatives as vasodilators," C.A. 129:275693.

Ollmann, et al., "Investigation of the inhibition of leukotriene A4 hydrolase," C.A. 123:160088.

Arnost, et al., Thermally developable photosensitive material, C.A. 121:145198.

Chauvel, et al., "Investigation of the Active Site of Aminopeptidase A using a Series of NewTthiol–Containing Inhibitors," C.A. 121:57907.

Singh, Prithipal, et al., "Salicylate conjugates and their preparation for immunogens and immunoassays,":C.A. 116:207795.

Hirai, Hiroyuki, et al., Heat–developable photographic material, C.A. 116:48968.

Frazee, et al., Leukotriene antagonists, C.A. 115:49105.

Young, Robert N., et al., "Preparation of diarylstyrylquinoline diacids as leukotriene antagonists,"C.A. 115:256016.

Bernstein, Peter R., et al., Synthesis and pharmacological characterization of a series of leukotriene analogs with antagonist and agonist activities, C.A. 108:94241.

Thorpe, Phillip E., et al., "New coupling agents for the synthesis of immunotoxins containing a hindered disulfide bond with improved stability in vivo," C.A. 108:87663.

Asahi chemical Industry Co., Ltd., Japan, "Printing of textiles with sulfur or sulfur vat dyes," C.A. 98:18055.

Portnyagina, V.A., et al., "Synthesis and properties of 1,3–dimercapto derivatives of aromatic carboxylic acids and o–aminophenol," C.A. 96:68506.

Staab, Heinz A., et al., [2.2.](2,7) Pyrenophane as an excimer model: synthesis and spectroscopic properties, C.A. 92:58489.

Chan, Edward Y., et al., "Benzothiazepinones, related compounds, and the Smiles rearrangement," C.A. 92:41909.

Mizyukova, I.G., et al., "Structure–toxicity relations of some thiol compounds," C.A. 73:23599.

Hsieh, Yu–Yuan, et al., "Chemotherapeutic studies on schistosomiasis—(IV) aryl ethers of dimercaptopropanol and their antimonial mercaptides," C.A. 52:15510b (CAOLD).

Lysenko, N.M., "Synthesis of certain beta—diothiols," C.A. 61:10583h (CAOLD).

Schlatter, Maurice J., "Products from HCHO and o–mercaptomethylbenzoic acid," C.A. 58:3359g (CAOLD).

Rees, Rees B., et al., "Aminopterin for psoriasis," C.A. 5320529f (CAOLD).

Beilstein Reg. No. (BRN): 3237981, (Autonom Name) 4–mercaptomethyl–benzoic acid.

(List continued on next page.)

*Primary Examiner*—Paul J. Killos
*Assistant Examiner*—Hector Reyes
(74) *Attorney, Agent, or Firm*—Foley & Lardner LLP

(57) ABSTRACT

The present invention relates to new thiolalkyl benzoic acids, pharmaceutical compositions and diagnostic kits comprising such compounds, and methods of using such compounds for inhibiting NAALADase enzyme activity, detecting diseases where NAALADase levels are altered, effecting neuronal activity, effecting TGF-β activity, inhibiting angiogenesis, and treating glutamate abnormalities, neuropathy, pain, compulsive disorders, prostate diseases, cancers, glaucoma, retinal disorders, and cancer.

17 Claims, 36 Drawing Sheets

OTHER PUBLICATIONS

Bernstein, P.R., et al., *J. Med. Chem.* (1988), 31(3), 692–6.
Chan, E.Y., et al., *Phosphorus and Sulfur*, 1979, vol. 7, pp. 41–45.
Staab, H.A., *Liebigs Ann. Chem.* (1979), (6), 886–98.
Thorpe, P.E., *Cancer Res.* (1987), 47, 5924–31.
U.S. patent application No. 09/346,711, filed Jul. 2, 1999.
Reed et al., "Nucleophilicities of Selected Ions in Water at 195°C", *Journal of Organic Chemistry*, 1993, pp. 6372–6376, vol. 58, No. 23, American Chemical Society, Washington, D.C.
Martin et al., "β–Amino–thiols Inhibit the Zinc Metallopeptidase Activity of Tetanus Toxin Light Chain", *Journal of Medicinal Chemistry*, 1998, pp. 3450–3460, vol. 41, No. 18, American Chemical Society, Washington, D.C.

Barkenbus et al., "The Reaction of Para–Substituted Benzyl Chlorides with Sodium Hydrogen Sulfide", *Journal of the American Chemical Society*, Oct. 1927, pp. 2549–2553, vol. 27, No. 10, American Chemical Society, Washington, D.C.

Database Crossfire Beilstein Online!, Beilstein Institut zur Förderung der Chemischen Wissenschaften, Frankfurt am Main DE; Database accession No. 3215120 (Citation No.) XP–002217097.

Vegh et al., "A New Convenient Method for Preparation of Condensed Aromatic and Heterocyclic Thiolactones," *Synthetic Communications*, 1992, pp. 2057–2061, vol. 22, No. 4, Marcel Dekker Inc., Basel, Switzerland.

* cited by examiner

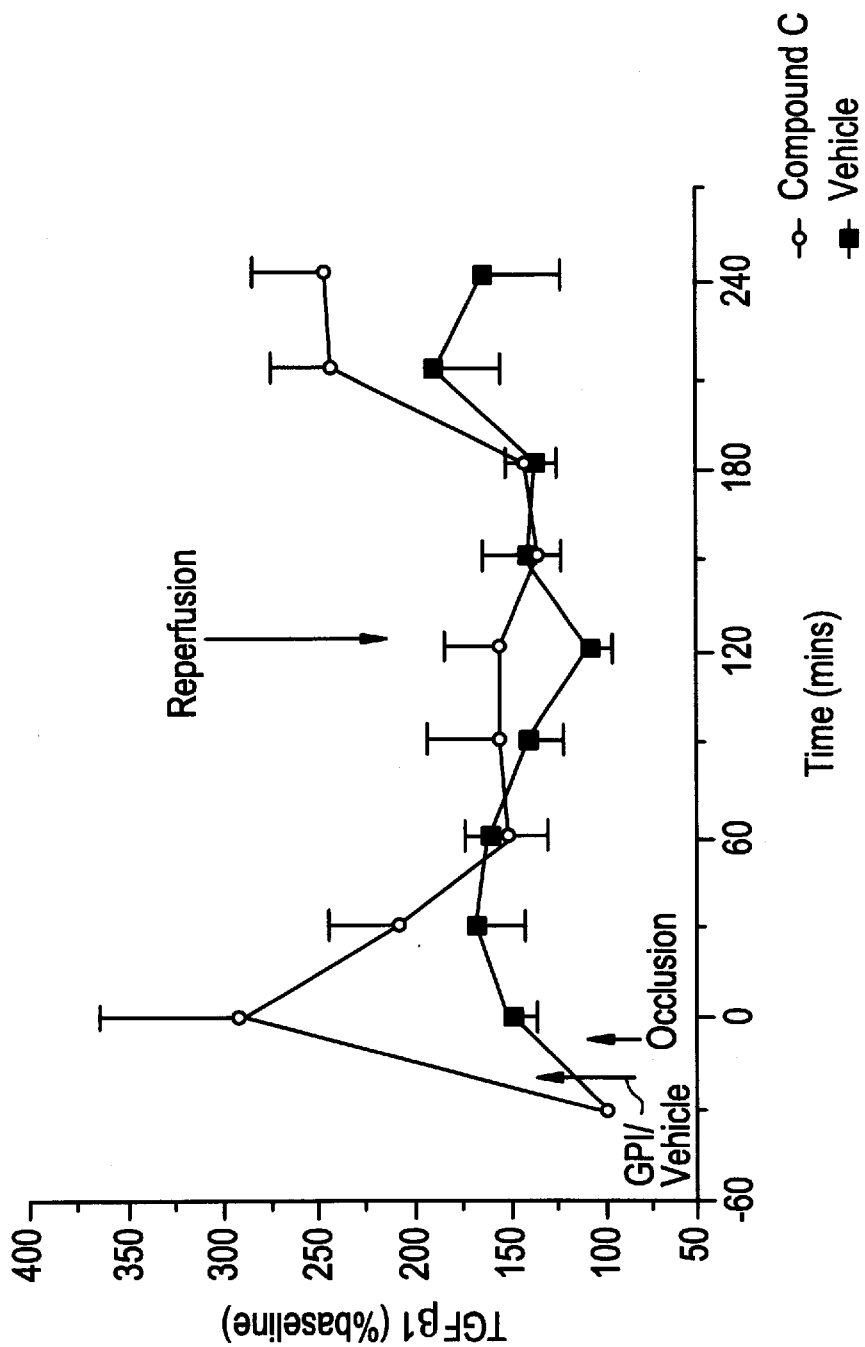

Presence of Limb Shaking at 210 Days

Kaplan-Meir Survival Curve of Mice After Treatment with Compound B and Vehicle

NAALADase Inhibition Reverses Sensory Nerve Conduction Deficit in Well-Established Diabetes MNCV on STZ-Rats Treated with Compound D/Vehicle Compound D Reverses Sensory Nerve Conduction Velocity Deficit in Established Diabetes Sensory Nerve Conduction Velocity Deficit Reversed by Compound D from 90 days post STZ

THIOLALKYL BENZOIC ACID DERIVATIVES

This application claims the benefit of U.S. Provisional Patent Application Nos. 60/294,036 and 60/342,746 filed on May 30, 2001, and Dec. 28, 2001, respectively, the entire disclosures of which are incorporated herein by reference.

The present invention relates to new compounds, pharmaceutical compositions and diagnostic kits comprising such compounds, and methods of using such compounds for inhibiting NAALADase enzyme activity, detecting diseases where NAALADase levels are altered, effecting neuronal activity, effecting TGF-β activity, inhibiting angiogenesis, and treating glutamate abnormalities, neuropathy, pain, compulsive disorders, prostate diseases, cancers, glaucoma, and retinal disorders.

The NAALADase enzyme, also known as prostate specific membrane antigen ("PSM" or "PSMA") and human glutamate carboxypeptidase II ("GCP II"), catalyzes the hydrolysis of the neuropeptide N-acetyl-aspartyl-glutamate ("NAAG") to N-acetyl-aspartate ("NAA") and glutamate. Based upon amino acid sequence homology, NAALADase has been assigned to the M28 family of peptidases.

Studies suggest NAALADase inhibitors may be effective in treating ischemia, spinal cord injury, demyelinating diseases, Parkinson's disease, Amyotrophic Lateral Sclerosis ("ALS"), alcohol dependence, nicotine dependence, cocaine dependence, cancer, neuropathy, pain and schizophrenia, and in inhibiting angiogenesis. In view of their broad range of potential applications, a need exists for new NAALADase inhibitors and pharmaceutical compositions comprising such compounds.

SUMMARY OF THE INVENTION

The present invention relates to a compound of formula Ia or a pharmaceutically acceptable equivalent:

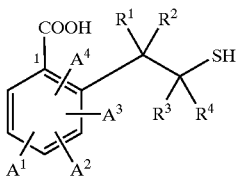

Ia wherein:
$R^1$, $R^2$, $R^3$, and $R^4$ are independently hydrogen or $C_1$–$C_3$ alkyl; and $A^1$, $A^2$, $A^3$, and $A^4$ are independently hydrogen, $C_1$–$C_9$ alkyl, $C_2$–$C_9$ alkenyl, $C_2$–$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$–$C_9$ alkylsulfonyl, $C_1$–$C_9$ alkoxy, $C_2$–$C_9$ alkenoxy, phenoxy, or benzyloxy, wherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s).

In one embodiment, $R^1$, $R^2$, $R^3$, $R^4$, $A^2$, $A^3$, and $A^4$ are hydrogen; and $A^1$ is hydrogen, —$(CH_2)_n$—W, or —Y—$(CH_2)_n$—W, wherein: n is 0–3; Y is O, S, or NR wherein R is hydrogen or C1–C4 alkyl; and W is C1–C6 alkyl or phenyl, wherein W is unsubstituted or substituted with C1–C4 alkyl, C1–C4 alkoxy, carboxy, or halo.

The present invention further relates to a compound of formula Ib or a pharmaceutically acceptable equivalent:

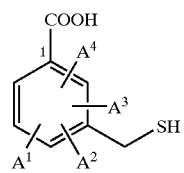

Ib wherein $A^1$, $A^2$, $A^3$ and $A^4$ are independently hydrogen, $C_1$–$C_9$ alkyl, $C_2$–$C_9$ alkenyl, $C_2$–$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$–$C_9$ alkylsulfonyl, $C_1$–$C_9$ alkoxy, $C_2$–$C_9$ alkenoxy, phenoxy, or benzyloxy, wherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s), wherein if $A^1$ is chloro, fluoro, amino, or thiomethyl then $A^2$, $A^3$, and $A^4$ may not all be hydrogen, and wherein at least one of $A^1$, $A^2$, $A^3$, and $A^4$ is not hydrogen.

In one embodiment, $A^2$, $A^3$, and $A^4$ are hydrogen; and $A^1$ is —$(CH_2)_n$—Ar or —Y—$(CH_2)_n$—Ar, wherein n is 0–3, Y is O, S, or NR wherein R is hydrogen or C1–C4 alkyl, and Ar is phenyl, unsubstituted or substituted with C1–C4 alkyl, carboxy, or halo.

The present invention further relates to a compound of formula I:

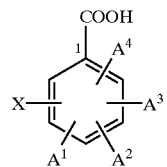

I or a pharmaceutically acceptable equivalent, wherein:
X is —$(CR^1R^2)_n$SH, —O$(CR^1R^2)_2$SH, —S$(CR^1R^2)_2$SH, or —NR$(CR^1R^2)_2$SH;

n is 1–3; and

R, $R^1$, $R^2$, $A^1$, $A^2$, $A^3$ and $A^4$ are independently hydrogen, $C_1$–$C_9$ alkyl, $C_2$–$C_9$ alkenyl, $C_2$–$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$–$C_9$ alkylsulfonyl, $C_1$–$C_9$ alkoxy, $C_2$–$C_9$ alkenoxy, phenoxy, or benzyloxy, wherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s).

Additionally, the present invention relates to a method for inhibiting NAALADase enzyme activity, detecting diseases where NAALADase levels are altered, effecting neuronal activity, effecting TGF-β, activity, inhibiting angiogenesis, or treating glutamate abnormalities, neuropathy, pain, compulsive disorders, prostate diseases, cancers, glaucoma, or retinal disorders, comprising administering to a mammal in need of such inhibition, treatment or effect, an effective amount of a compound of formula I, Ia, or Ib, as defined above.

The present invention further relates to a method for detecting a disease, disorder or condition where NAALADase levels are altered, comprising:

(i) contacting a sample of bodily tissue or fluid with a compound of formula I, Ia, or Ib, as defined above, wherein said compound binds to any NAALADase in said sample; and (ii) measuring the amount of any NAALADase bound to said sample, wherein the amount of NAALADase is diagnostic for said disease, disorder, or condition.

The present invention also relates to a method for detecting a disease, disorder or condition where NAALADase levels are altered in an animal or a mammal, comprising:

(i) labeling a compound of formula I, Ia, or Ib, as defined above, with an imaging reagent;

(ii) administering to said animal or mammal an effective amount of the labeled compound;

(iii) allowing said labeled compound to localize and bind to NAALADase present in said animal or mammal; and (iv) measuring the amount of NAALADase bound to said labeled compound, wherein the amount of NAALADase is diagnostic for said disease, disorder, or condition.

Additionally, the present invention further relates to a diagnostic kit for detecting a disease, disorder, or condition where NAALADase levels are altered, comprising a compound of formula I, Ia, or Ib, as defined above, labeled with a marker.

Finally, the present invention relates to a pharmaceutical composition comprising:

(i) an effective amount of a compound of formula I, Ia, or Ib, as described above; and (ii) a pharmaceutically acceptable carrier.

BRIEF DESCRIPTION OF THE DRAWINGS

FIG. 6 is a bar graph showing the effect of Compound C on TGF-β1 levels during occlusion and reperfusion in rats subjected to MCAO.

DETAILED DESCRIPTION

Definitions

Figure 1:
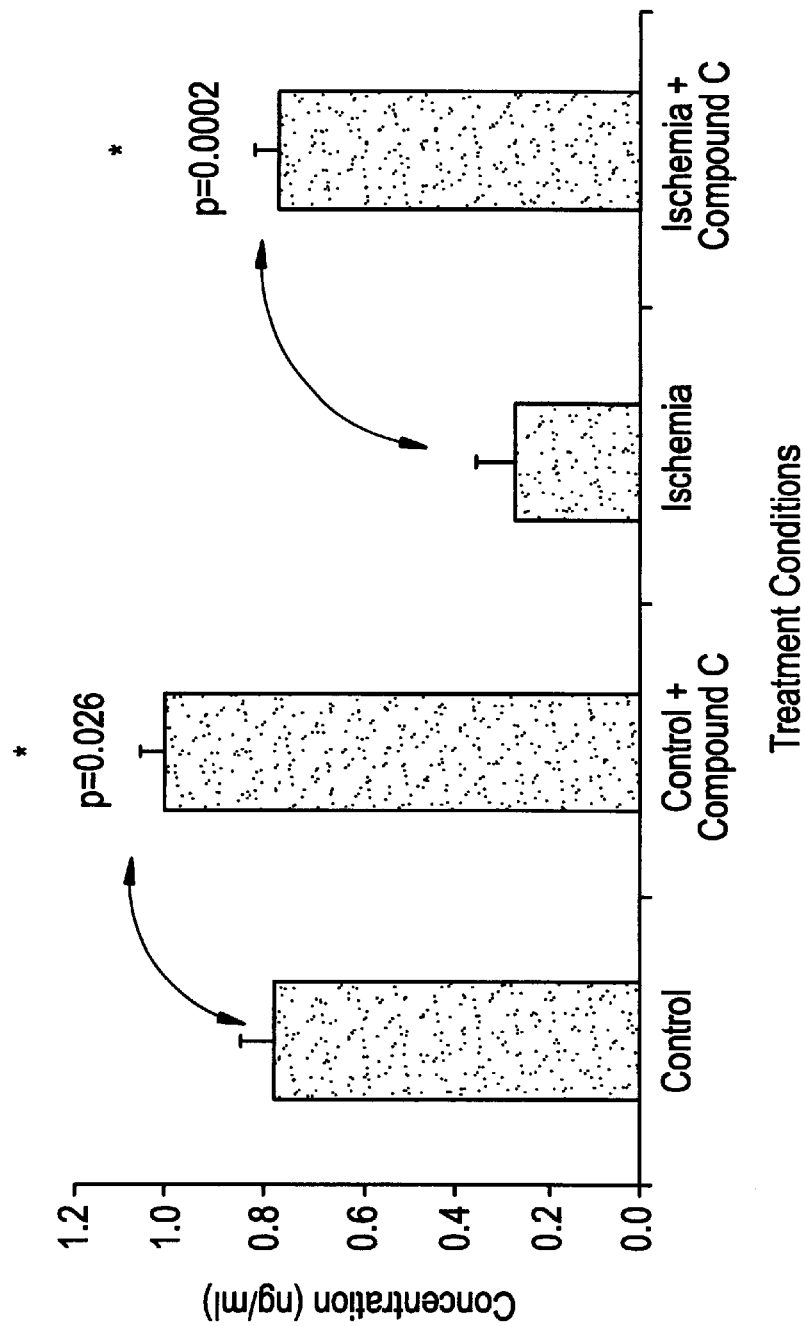
FIG. 1 is a bar graph showing the effect of Compound C on TGF-β1 concentrations in ischemic cell cultures.

"Compound A" refers to 2-[[2,3,4,5,6-pentafluorobenzyl) hydroxyphosphinyl]methyl]pentanedioic acid.

"Compound B" refers to 2-(3-sulfanylpropyl) pentanedioic acid.

"Compound C" refers to 2-(phosphonomethyl) pentanedioic acid ("PMPA").

"Compound D" refers to 2-(2-sulfanylethyl)pentanedioic acid.

"Compound E" refers to 3-carboxy-alpha-(3-mercaptopropyl)-benzenepropanoic acid.

"Compound F" refers to 3-carboxy-5-(1,1-dimethylethyl)-alpha-(3-mercaptopropyl)-benzenepropanoic acid.

"Compound 9" refers to 2-[(4-carboxyphenyl)methoxy]-6-(2-mercaptoethyl)-benzoic acid.

"Compound 10" refers to 3-(2-mercaptoethyl)-[1,1'-biphenyl]-2,3'-dicarboxylic acid.

"Alkyl" refers to a branched or unbranched saturated hydrocarbon chain comprising a designated number of carbon atoms. For example, $C_1$–$C_9$ alkyl is a straight or branched hydrocarbon chain containing 1 to 9 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$–$C_9$ alkenyl is a straight or branched hydrocarbon chain containing 2 to 9 carbon atoms having at least one double bond, and includes but is not limited to substituents such as ethenyl, propenyl, iso-propenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 9 carbon atoms.

"Carbocycle" refers to a hydrocarbon, cyclic moiety having one or more closed ring(s) that is/are alicyclic, aromatic, fused, and/or bridged. Examples include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl, and pyrene.

"Aryl" refers to an aromatic, hydrocarbon cyclic moiety having one or more closed rings. Examples include, without limitation, phenyl, benzyl, naphthyl, anthracenyl, phenanthracenyl, biphenyl, and pyrenyl.

"Heterocycle" refers to a cyclic moiety having one or more closed rings that is/are alicyclic, aromatic, fused, and/or bridged, with one or more heteroatoms (for example, sulfur, nitrogen or oxygen) in at least one of the rings. Examples include, without limitation, pyrrolidine, pyrrole, thiazole, thiophene, piperidine, pyridine, isoxazolidine, and isoxazole.

"Heteroaryl" refers to an aromatic, cyclic moiety having one or more closed rings with one or more heteroatoms (for example, sulfur, nitrogen, or oxygen) in at least one of the rings. Examples include, without limitation, pyrrole, thiophene, pyridine, and isoxazole.

"Derivative" refers to a substance produced from another substance either directly or by modification or partial substitution.

"Effective amount" refers to the amount required to produce the desired effect. "Therapeutically effective amount" refers to the amount required to inhibit NAALADase enzyme activity and/or angiogenesis, to effect neuronal activity or TGF-β activity, and/or to treat glutamate abnormality, neuropathy, pain, compulsive disorder, prostate disease, cancer, glaucoma, and/or retinal disorders.

"Electromagnetic radiation" includes without limitation radiation having the wavelength of $10^{-20}$ to $10^0$ meters. Examples include, without limitation, gamma radiation ($10^{-20}$ to $10^{-13}$ m), X-ray radiation ($10^{-11}$ to $10^{-9}$ m), ultraviolet light (10 nm to 400 nm), visible light (400 nm to 700 nm), infrared radiation (700 nm to 1.0 mm) and microwave radiation (1 mm to 30 cm).

"Halo" refers to at least one fluoro, chloro, bromo, or iodo moiety.

"Isosteres" refer to elements, functional groups, substitutents, molecules or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Ideally, isosteric compounds should be isomorphic and able to co-crystallize. Other physical properties that isosteric compounds usually share include boiling point, density, viscosity and thermal conductivity. However, certain properties are usually different: dipolar moments, polarity, polarization, size and shape since the external orbitals may be hybridized differently. The term "isosteres" encompasses "bioisosteres."

"Bioisosteres" are isosteres that, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acylcyanamides, and acylsulfonamides; planar acidic heterocycles such as tetrazoles, mercaptoazoles, sulfinylazoles, sulfonylazoles, isoxazoles, isothiazoles, hydroxythiadiazoles, and hydroxychromes; and nonplanar sulfur- or phosphorus-derived acidic functions such as phosphinates, phosphonates, phosphonamides, sulphonates, sulphonamides, and acylsulphonamides.

"Metabolite" refers to a substance produced by metabolism or by a metabolic process.

"NAAG" refers to N-acetyl-aspartyl-glutamate, an important peptide component of the brain, with levels comparable to the major inhibitor neurotransmitter gamma-aminobutyric acid ("GABA"). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. In addition, NAAG is an agonist at group II metabotropic glutamate receptors, specifically mGluR3 receptors; when attached to a moiety capable of inhibiting NAALADase, it is expected that metabotropic glutamate receptor ligands will provide potent and specific NAALADase inhibitors.

"NAALADase" refers to N-acetylated α-linked acidic dipeptidase, a membrane bound metallopeptidase which catabolizes NAAG to N-acetylaspartate ("NAA") and glutamate ("GLU"):

CATABOLISM OF NAAG BY NAALADASE

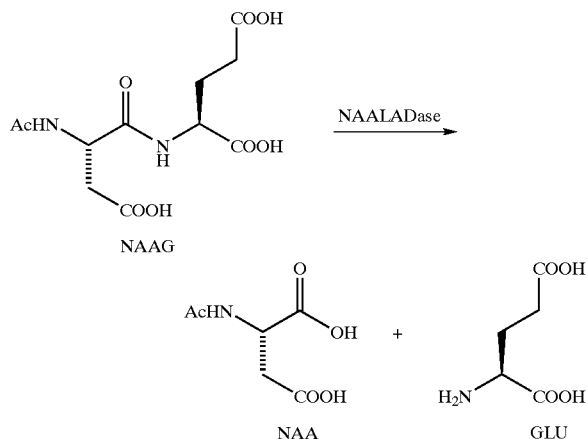

NAALADase has been assigned to the M28 peptidase family and is also called PSMA or GCP II, EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

"Pharmaceutically acceptable equivalent" includes, without limitation, pharmaceutically acceptable salts, hydrates, metabolites, prodrugs, and isosteres. Many pharmaceutically acceptable equivalents are expected to have the same or similar in vitro or in vivo activity as the compounds of the invention.

"Pharmaceutically acceptable salt" refers to a salt of the inventive compounds which possesses the desired pharmacological activity and which is neither biologically nor otherwise undesirable. The salt can be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate, and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. Basic nitrogen-containing groups can be quarternized with agents including lower alkyl halides such as methyl, ethyl, propyl and butyl chlorides, bromides, and iodides; dialkyl sulfates such as dimethyl, diethyl, dibutyl, and diamyl sulfates; long chain halides such as decyl, lauryl, myristyl and stearyl chlorides, bromides, and iodides; and aralkyl halides such as benzyl and phenethyl bromides.

"Prodrug" refers to a derivative of the inventive compounds that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995).

"Radiosensitizer" refers to a low molecular weight compound administered to animals in therapeutically effective amounts to promote the treatment of diseases that are treatable with electromagnetic radiation. Diseases that are treatable with electromagnetic radiation include, without limitation, neoplastic diseases, benign and malignant tumors, and cancerous cells. Electromagnetic radiation treatment of other diseases not listed herein are also contemplated by the present invention.

"Inhibition," in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound that is required to cause a 50% inhibition of the target enzyme.

"NAALADase inhibitor" refers to any compound that inhibits NAALADase enzyme activity. Preferably, a NAALADase inhibitor exhibits a $K_i$ of less than 100 μM, more preferably less than 10 μM, and even more preferably less than 1 μM, as determined using any appropriate assay known in the art.

"Isomers" refer to compounds having the same number and kind of atoms, and hence the same molecular weight, but differing in respect to the arrangement or configuration of the atoms.

"Stereoisomers" are isomers that differ only in the arrangement of the atoms in space.

"Optical isomers" refer to enantiomers or diastereoisomers.

"Diastereoisomers" are stereoisomers that are not mirror images of each other. Diastereoisomers occur in compounds having two or more asymmetric carbon atoms; thus, such compounds have $2^n$ optical isomers, where n is the number of asymmetric carbon atoms.

"Enantiomers" are a pair of stereoisomers that are non-superimposable mirror images of each other. Enantiomers result from the presence of one or more asymmetric carbon atoms in the compound (e.g., glyceraldehyde, lactic acid, sugars, tartaric acid, amino acids).

"Enantiomer-enriched" refers to a mixture in which one enantiomer predominates.

"Racemic mixture" means a mixture containing equal amounts of individual enantiomers.

"Non-racemic mixture" is a mixture containing unequal amounts of enantiomers.

"Angiogenesis" refers to the process whereby new capillaries are formed. "Inhibition" of angiogenesis may be measured by many parameters in accordance with the present invention and, for instance, may be assessed by delayed appearance of neovascular structures, slowed development of neovascular structures, decreased occurrence of neovascular structures, slowed or decreased severity of angiogenesis-dependent disease effects, arrested angiogenic growth, or regression of previous angiogenic growth. In the extreme, complete inhibition is referred to herein as prevention. In relation to angiogenesis or angiogenic growth, "prevention" refers to no substantial angiogenesis or angiogenic growth if none had previously occurred, or no substantial further angiogenesis or angiogenic growth if growth had previously occurred.

"Angiogenesis-dependent disease" includes, without limitation, rheumatoid arthritis, cardiovascular diseases, neovascular diseases of the eye, peripheral vascular disorders, dermatologic ulcers, and cancerous tumor growth, invasion and metastasis.

"Animal" refers to a living organism having sensation and the power of voluntary movement, and which requires for its existence oxygen and organic food. Examples include, without limitation, members of the human, equine, porcine, bovine, murine, canine, or feline species. In the case of a human, an "animal" may also be referred to as a "patient."

"Mammal" refers to a warm-blooded vertebrate animal.

"Anxiety" includes without limitation the unpleasant emotion state including psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. *Dorland's Illustrated Medical Dictionary*, 27th ed. (W. B. Saunders Co. 1988).

"Anxiety Disorder" includes without limitation mental disorders in which anxiety and avoidance behavior predominate. *Dorland's Illustrated Medical Dictionary*. Examples include without limitation panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in *Diagnostic and Statistical Manual of Mental Disorders* (American Psychiatric Association 4th ed. 1994).

"Attention Deficit Disorder" ("ADD") refers to a disorder characterized by developmentally inappropriate inattention and impulsiveness, with or without hyperactivity. Inattention means a failure to finish tasks started, easily distracted, seeming lack of attention, and difficulty concentrating on tasks requiring sustained attention. Impulsiveness means acting before thinking, difficulty taking turns, problems organizing work, and constant shifting from one activity to another. Hyperactivity means difficulty staying seated and sitting still, and running or climbing excessively.

"Cancer" includes, without limitation, ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"Compulsive disorder" refers to any disorder characterized by irresistible impulsive behavior. Examples of compulsive disorders include without limitation substance dependence, eating disorders, pathological gambling, ADD, and Tourette's syndrome.

"Substance dependence" refers to a psychologic addiction or a physical tolerance to a substance, e.g., a drug. Tolerance means a need to increase the dose progressively in order to produce the effect originally achieved by smaller amounts.

"Demyelinating disease" refers to any disease involving damage to or removal of the myelin sheath naturally surrounding nerve tissue, such as that defined in U.S. Pat. No.

5,859,046 and International Publication No. WO 98/03178, herein incorporated by reference. Examples include without limitation peripheral demyelinating diseases (such as Guillain-Barré syndrome, peripheral neuropathies and Charcot-Marie Tooth disease) and central demyelinating diseases (such as multiple sclerosis).

"Disease" refers to any deviation from or interruption of the normal structure or function of any part, organ or system (or combinations) of the body that is manifested by a characteristic set of symptoms and signs and whose etiology, pathology, and prognosis may be known or unknown. *Dorland's Illustrated Medical Dictionary.*

"Disorder" refers to any derangement or abnormality of function; a morbid physical or mental state. *Dorland's Illustrated Medical Dictionary.*

"Eating disorder" refers to compulsive overeating, obesity or severe obesity. Obesity means body weight of 20% over standard height-weight tables. Severe obesity means over 100% overweight.

"Glaucoma" includes without limitation chronic (idiopathic) open-angle glaucomas (e.g., high-pressure, normal-pressure); pupillary block glaucomas (e.g., acute angle-closure, subacute angle-closure, chronic angle-closure, combined-mechanism); developmental glaucomas (e.g., congenital (infantile), juvenile, Anxenfeld-Rieger syndrome, Peters' anomaly, Aniridia); glaucomas associated with other ocular disorders (e.g., glaucomas associated with disorders of the corneal endothelium, iris, ciliary body, lens, retina, choroid and vitreous); glaucomas associated with elevated episcleral venous pressure (e.g., systemic diseases with associated elevated intraocular pressure and glaucoma, corticosteroid-induced glaucoma); glaucomas associated with inflammation and trauma (e.g., glaucomas associated with keratitis, episcleritis, scleritis, uveitis, ocular trauma, and hemorrhage); glaucomas following intraocular surgery, e.g., ciliary block (malignant) glaucoma, glaucomas in aphakia and pseudophakia, glaucomas associated with corneal surgery, glaucomas associated with vitreoretinal surgery.

"Glutamate abnormality" refers to any disease, disorder, or condition in which glutamate is implicated, including pathological conditions involving elevated levels of glutamate. Examples of glutamate abnormalities include, without limitation, spinal cord injury, epilepsy, stroke, Alzheimer's disease, Parkinson's disease, ALS, Huntington's disease ("HD"), schizophrenia, pain, ischemia, peripheral neuropathy (including but not limited to neuropathy), traumatic brain injury, neuronal insult, inflammatory diseases, anxiety, anxiety disorders, memory impairment, compulsive disorders, glaucoma, and/or retinal disorders.

"Ischemia" refers to localized tissue anemia due to obstruction of the inflow of arterial blood. Global ischemia occurs when blood flow ceases for a period of time, as may result from cardiac arrest. Focal ischemia occurs when a portion of the body, such as the brain, is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_1$, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Metastasis" refers to "[t]he ability of cells of a cancer to disseminate and form new foci of growth at noncontiguous sites (ie., to form metastases)." See Hill, R. P, "Metastasis", *The Basic Science of Oncology*, Tannock et al., Eds., pp. 178–195 (McGraw-Hill 1992), herein incorporated by reference. "The transition from in situ tumor growth to metastatic disease is defined by the ability of tumor cells of the primary site to invade local tissues and to cross tissue barriers . . . To initiate the metastatic process, carcinoma cells must first penetrate the epithelial basement membrane and then invade the interstitial stroma . . . For distant metastases, intravasation requires tumor cell invasion of the subendothelial basement membrane that must also be negotiated during tumor cell extravasation . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* (1993) 71:1368–1383, herein incorporated by reference.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination processes, epilepsy, cognitive disorder, glutamate abnormality and secondary effects thereof.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuropathy" refers to any disease or malfunction of the nerves. Neuropathy includes, without limitation, peripheral neuropathy, diabetic neuropathy, autonomic neuropathy and mononeuropathy. Peripheral neuropathy may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barré syndrome, diabetes including Type I and Type II diabetes), chemicals (for example, toxins, lead, dapsone, vitamins, paclitaxel chemotherapy, HAART therapy) and physical injuries to a particular nerve or nerve plexus (for example, trauma, compression, constriction).

"Neuroprotective" refers to the effect of reducing, arresting or ameliorating nervous insult, and protecting, resuscitating or reviving nervous tissue that has suffered nervous insult.

"Pain" refers to localized sensations of discomfort, distress or agony, resulting from the stimulation of specialized nerve endings. It serves as a protective mechanism insofar as it induces the sufferer to remove or withdraw from the source. *Dorland's Illustrated Medical Dictionary*. Examples of pain include, without limitation, acute, chronic, cancer, burn, incisional, inflammatory, diabetic neuropathic and back pain.

"Neuropathic pain" refers to a condition of pain associated with a nerve injury. Depending on the particular syndrome, the pain may be due to alterations of the brain or spinal cord or may be due to abnormalities in the nerve itself. Neuropathic pain may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barré syndrome, and diabetes, including Type I and Type II diabetes), chemicals (for example, toxins, lead, dapsone, vitamins, paclitaxel chemotherapy, and HAART therapy) and physical injuries to a particular nerve or nerve plexus (for example, trauma, compression, and constriction).

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Prostate disease" refers to any disease affecting the prostate. Examples of prostate disease include without limitation prostate cancer such as adenocarcinoma and metastatic cancers of the prostate; and conditions characterized by abnormal growth of prostatic epithelial cells such as benign prostatic hyperplasia.

"Schizophrenia" refers to a mental disorder or group of mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include, without limitation, acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia. *Dorland's Illustrated Medical Dictionary*.

"TGF-β" refers to transforming growth factor beta. TGF-β is recognized as a prototype of multifunctional growth factors. It regulates various cell and tissue functions, including cell growth and differentiation, angiogenesis, wound healing, immune function, extracellular matrix production, cell chemotaxis, apoptosis and hematopoiesis.

"TGF-β abnormality" refers to any disease, disorder or condition in which TGF-β is implicated, including diseases disorders and conditions characterized by an abnormal level of TGF-β.

"Abnormal level of TGF-β" refers to a measurable variance from normal levels of TGF-β, as determined by one of ordinary skill in the art using known techniques.

"Therapeutic window of opportunity" or "window" refers, in relation to stroke, to the maximal delay between the onset of stroke and the initiation of efficacious therapy.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Treating" refers to:
(i) preventing a disease, disorder or condition from occurring in an animal that may be predisposed to the disease, disorder and/or condition but has not yet been diagnosed as having it;
(ii) inhibiting the disease, disorder or condition, i.e., arresting its development; and/or
(iii) relieving the disease, disorder or condition, i.e., causing regression of the disease, disorder and/or condition.

"Treating ALS" refers to:
(i) preventing ALS from occurring in an animal that may be predisposed to ALS but has not yet been diagnosed as having it;
(ii) inhibiting ALS, e.g., arresting its development;
(iii) relieving ALS, e.g., causing regression of the disease, disorder and/or condition;
(iv) delaying onset of ALS or ALS symptom(s);
(v) slowing progression of ALS or ALS symptom(s);
(vi) prolonging survival of an animal suffering from ALS; and/or
(vii) attenuating ALS symptom(s).

"Treating Huntington's disease" refers to:
(i) preventing Huntington's disease from occurring in an animal that may be predisposed to Huntington's disease but has not yet been diagnosed as having it;
(ii) inhibiting or slowing Huntington's disease, e.g. arresting its development;
(iii) relieving Huntington's disease, e.g. causing its regression;

15

(iv) improving motor coordination in an animal having Huntington's disease; and/or (v) prolonging the survival of an animal having Huntington's disease.

"Treating substance dependence" refers to suppressing the psychologic addiction or physical tolerance to the drug of abuse, and/or relieving and/or preventing a withdrawal syndrome resulting from the drug dependence.

"Dependence" refers to a maladaptive pattern of substance use, leading to clinically significant impairment or distress. Dependence is typically characterized by tolerance and/or withdrawal. Substances for which dependence may be developed include, without limitation, depressants (opioids, synthetic narcotics, barbiturates, glutethimide, methyprylon, etchlorvynol, methaqualone, alcohol); anxiolytics (diazepam, chlordiazepoxide, alprazolam, oxazepam, temazepam); stimulants (amphetamine, methamphetamine, cocaine); and hallucinogens (LSD, mescaline, peyote, marijuana).

"Tolerance" refers to an acquired reaction to a substance characterized by diminished effect with continued use of the same dose and/or a need for increased doses to achieve intoxication or desired effect previously achieved by lower doses. Both physiological and psychosocial factors may contribute to the development of tolerance. With respect to physiological tolerance, metabolic and/or functional tolerance may develop. By increasing the rate of metabolism of the substance, the body may be able to eliminate the substance more readily. Functional tolerance is defined as a decrease in sensitivity of the central nervous system to the substance.

"Withdrawal" refers to a syndrome characterized by untoward physical changes that occur following cessation of or reduction in substance use, or administration of a pharmacologic antagonist.

"Treating a retinal disorder" refers to:

(i) preventing a retinal disorder from occurring in an animal that may be predisposed to a retinal disorder but has not yet been diagnosed as having it;

(ii) inhibiting a retinal disorder, e.g., arresting its development; and/or (iii) relieving a retinal disorder, e.g., causing its regression.

"Retinal disorder" refers to vascular retinopathy, for example, hypertensive retinopathy, diabetic retinopathy (nonproliferative or proliferative), central retinal artery occlusion, or central retinal vein occlusion; age-related macular degeneration; retinal detachment; or retinitis pigmentosa.

One of ordinary skill in the art will recognize that there are alternative nomenclatures, nosologies and classification systems for the diseases, disorders and conditions defined above, and that such systems evolve with medical scientific progress.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

16

COMPOUNDS OF THE INVENTION

The present invention relates to a compound of formula Ia:

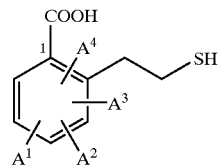

Ia wherein $A^1$, $A^2$, $A^3$ and $A^4$ are independently hydrogen, $C_1$–$C_9$ alkyl, $C_2$–$C_9$ alkenyl, $C_2$–$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$–$C_9$ alkylsulfonyl, $C_1$–$C_9$ alkoxy, $C_2$–$C_9$ alkenoxy, phenoxy, or benzyloxy, wherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s).

In one embodiment, $R^1$, $R^2$, $R^3$, $R^4$, $A^2$, $A^3$, and $A^4$ are hydrogen; and $A^1$ is hydrogen, —$(CH_2)_n$—W, or —Y—$(CH_2)_n$—W, wherein: n is 0–3; Y is O, S, or NR wherein R is hydrogen or C1–C4 alkyl; and W is C1–C6 alkyl or phenyl, wherein W is unsubstituted or substituted with C1–C4 alkyl, C1–C4 alkoxy, carboxy, or halo.

The present invention further relates to a compound of formula Ib:

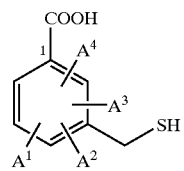

Ib wherein $A^1$, $A^2$, $A^3$ and $A^4$ are independently hydrogen, $C_1$–$C_9$ alkyl, $C_2$–$C_9$ alkenyl, $C_2$–$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$–$C_9$ alkylsulfonyl, $C_1$–$C_9$ alkoxy, $C_2$–$C_9$ alkenoxy, phenoxy, or benzyloxy, wherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s), wherein if $A^1$ is chloro, fluoro, amino, or thiomethyl then $A^2$, $A^3$, and $A^4$ may not all be hydrogen, and wherein at least one of $A^1$, $A^2$, $A^3$, and $A^4$ is not hydrogen.

In one embodiment, $A^2$, $A^3$, and $A^4$ are hydrogen; and $A^1$ is —$(CH_2)_n$—Ar or —Y—$(CH_2)_n$—Ar, wherein n is 0–3, Y is O, S, or NR wherein R is hydrogen or C1–C4 alkyl, and Ar is phenyl, unsubstituted or substituted with C1–C4 alkyl, carboxy, or halo.

The present invention further relates to a compound of formula I:

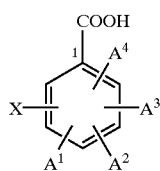

or a pharmaceutically acceptable equivalent, wherein:
X is —(CR$^1$R$^2$)$_n$SH, —O(CR$^1$R$^2$)$_2$SH, —S(CR$^1$R$^2$)$_2$SH, or —NR(CR$^1$R$^2$)$_2$SH;
n is 1–3; and
R, R$^1$, R$^2$, A$^1$, A$^2$, A$^3$ and A$^4$ are independently hydrogen, C$_1$–C$_9$ alkyl, C$_2$–C$_9$ alkenyl, C$_2$–C$_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, C$_1$–C$_9$ alkylsulfonyl, C$_1$–C$_9$ alkoxy, C$_2$–C$_9$ alkenoxy, phenoxy, or benzyloxy, wherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s).

Possible substituents of said alkyl, alkenyl, alkynyl, aryl, heteroaryl, carbocycle, heterocycle, alkoxy, alkenyloxy, phenoxy, benzyloxy, and fused ring include, without limitation, C$_1$–C$_6$ alkyl, C$_2$–C$_6$ alkenyl, C$_2$–C$_6$ alkynyl, C$_1$–C$_6$ alkoxy, C$_2$–C$_6$ alkenyloxy, phenoxy, benzyloxy, hydroxy, carboxy, hydroperoxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, nitro, nitroso, isonitroso, nitrosamino, imino, nitrosimino, oxo, C$_1$–C$_6$ alkylthio, sulfamino, sulfamoyl, sulfeno, sulfhydryl, sulfinyl, sulfo, sulfonyl, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, disilanyl, siloxy, silyl, silylene, and carbocyclic and heterocyclic moieties. Carbocyclic moieties include alicyclic and aromatic structures.

Examples of carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

Representative compounds of the present invention are set forth below in Table I.

TABLE I

| Compound No. | Structure | Name |
|---|---|---|
| 1 | 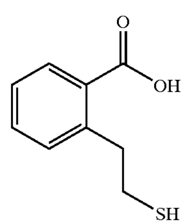 | 2-(2-mercaptoethyl)-benzoic acid |
| 2 | 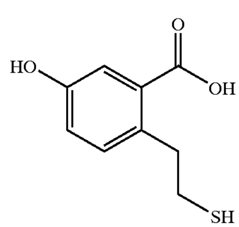 | 5-hydroxy-2-(2-mercaptoethyl)-benzoic acid |
| 3 | 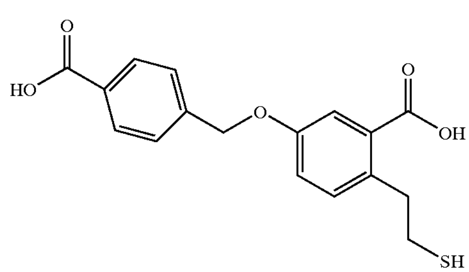 | 5-[(4-carboxyphenyl)methoxy]-2-(2-mercaptoethyl)-benzoic acid |

TABLE I-continued
| Compound No. | Structure | Name |
|---|---|---|
| 4 | 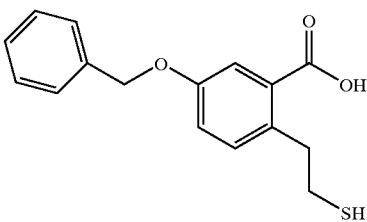 | 2-(2-mercaptoethyl)-5-(phenylmethoxy)-benzoic acid, |
| 5 | 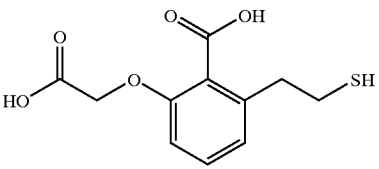 | 2-(carboxymethoxy)-6-(2-mercaptoethyl)-benzoic acid |
| 6 | 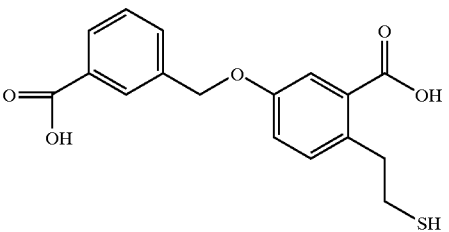 | 5-[(3-carboxyphenyl)methoxy]-2-(2-mercaptoethyl)-benzoic acid |
| 7 | 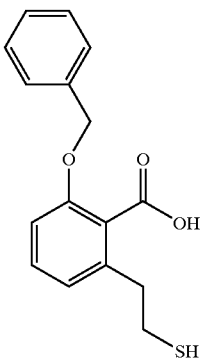 | 2-(2-mercaptoethyl)-6-(phenylmethoxy)-benzoic acid |
| 8 | 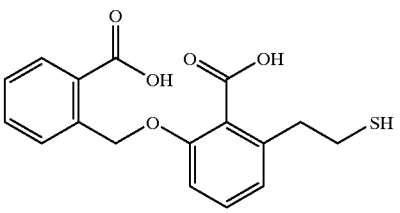 | 2-[(2-carboxyphenyl)methoxy]-6-(2-mercaptoethyl)-benzoic acid |
| 9 | 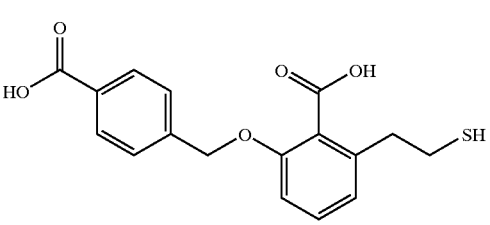 | 2-[(4-carboxyphenyl)methoxy]-6-(2-mercaptoethyl)-benzoic acid |

TABLE I-continued

| Compound No. | Structure | Name |
|---|---|---|
| 10 | 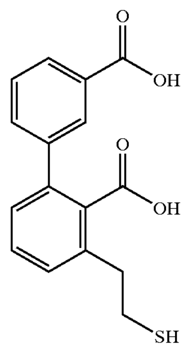 | 3-(2-mercaptoethyl)-[1,1'-biphenyl]-2,3'-dicarboxylic acid |
| 11 | 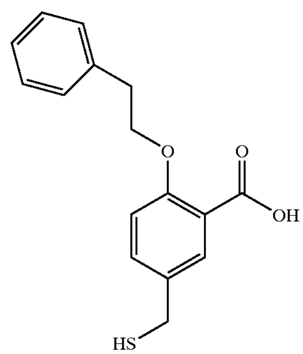 | 5-(mercaptomethyl)-2-(2-phenylethoxy)-benzoic acid |
| 12 | 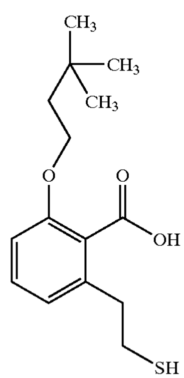 | 2-(3,3-dimethylbutoxy)-6-(2-mercaptoethyl)-benzoic acid |
| 13 | 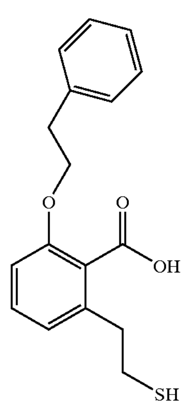 | 2-(2-mercaptoethyl)-6-(2-phenylethoxy)-benzoic acid |

TABLE I-continued

| Compound No. | Structure | Name |
|---|---|---|
| 14 | 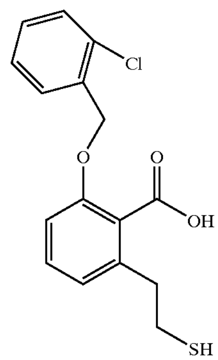 | 2-[(2-chlorophenyl)methoxy]-6-(2-mercaptoethyl)-benzoic acid |
| 15 | 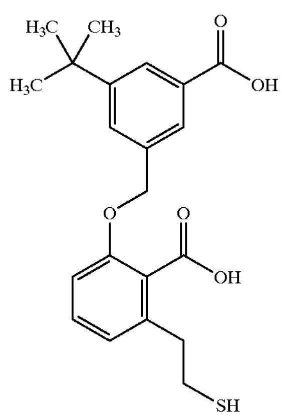 | 2-[[3-carboxy-5-(1,1-dimethylethyl)phenyl]methoxy]-6-(2-mercaptoethyl)-benzoic acid |
| 16 | 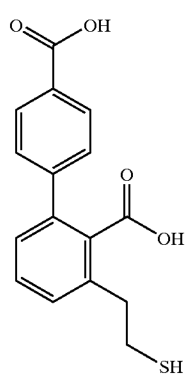 | 3-(2-mercaptoethyl)-[1,1'-biphenyl]-2,4'-dicarboxylic acid |

TABLE I-continued

| Compound No. | Structure | Name |
|---|---|---|
| 17 | 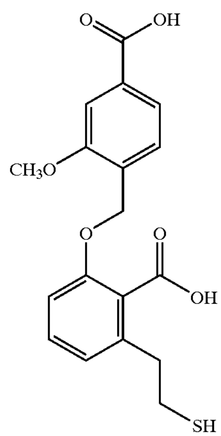 | 2-[(4-carboxy-2-methoxyphenyl)methoxy]-6-(2-mercaptoethyl)-benzoic acid |
| 18 | 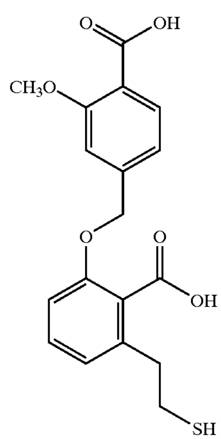 | 2-[(4-carboxy-3-methoxyphenyl)methoxy]-6-(2-mercaptoethyl)-benzoic acid |
| 19 | 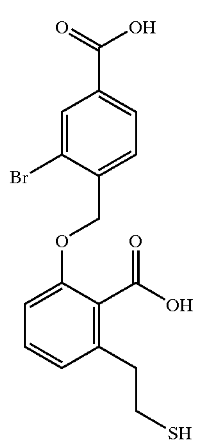 | 2-[(2-bromo-4-carboxyphenyl)methoxy]-6-(2-mercaptoethyl)-benzoic acid |

TABLE I-continued

| Compound No. | Structure | Name |
|---|---|---|
| 20 | 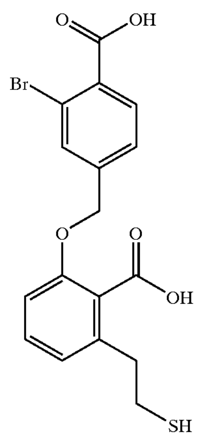 | 2-[(3-bromo-4-carboxyphenyl)methoxy]-6-(2-mercaptoethyl)-benzoic acid |
| 21 | 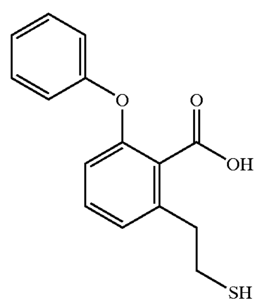 | 2-(2-mercaptoethyl)-6-phenoxy-benzoic acid |
| 22 | 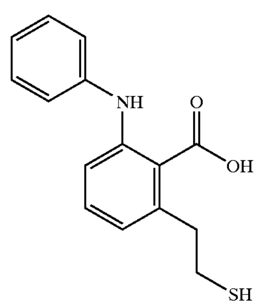 | 2-(2-mercaptoethyl)-6-phenylamino-benzoic acid |
| 23 | 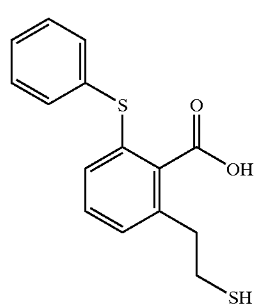 | 2-(2-mercaptoethyl)-6-(phenylthio)-benzoic acid |

TABLE I-continued

| Compound No. | Structure | Name |
|---|---|---|
| 24 | 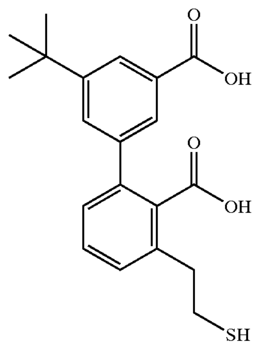 | 5'-(1,1-dimethylethyl)-3-(2-mercaptoethyl)-[1,1'-biphenyl]-2,3'-dicarboxylic acid |
| 25 | 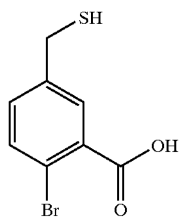 | 2-bromo-5-(mercaptomethyl)-benzoic acid |
| 26 | 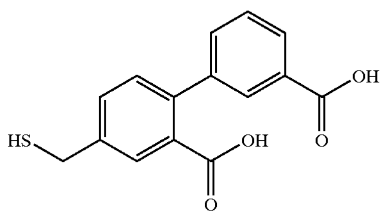 | 4-(mercaptomethyl)-[1,1'-biphenyl]-2,3'-dicarboxylic acid |
| 27 | 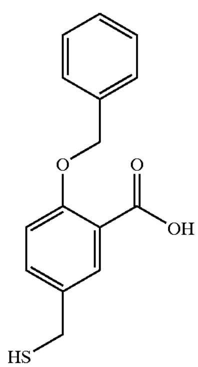 | 5-(mercaptomethyl)-2-(phenylmethoxy)-benzoic acid |
| 28 | 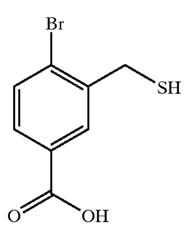 | 4-bromo-3-(mercaptomethyl)-benzoic acid |
| 29 | 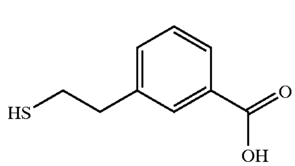 | 3-(2-mercaptoethyl)-benzoic acid |

TABLE I-continued
| Compound No. | Structure | Name |
|---|---|---|
| 30 | 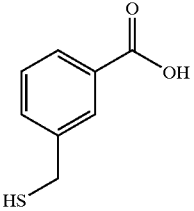 | 3-(mercaptomethyl)-benzoic acid |
| 31 | 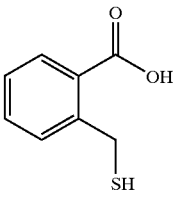 | 2-(mercaptomethyl)-benzoic acid |
| 32 | 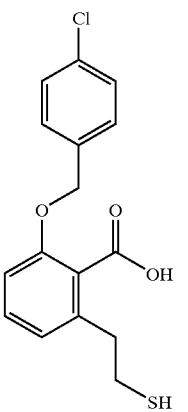 | 2-[(4-chlorophenyl)methoxy]-6-(2-mercaptoethyl)-benzoic acid |
| 33 | 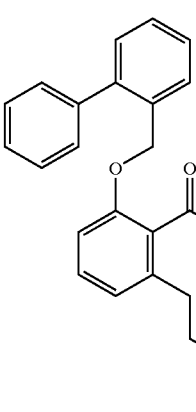 | 2-(biphenyl-2-ylmethoxy)-6-(2-mercaptoethyl)-benzoic acid |

TABLE I-continued

| Compound No. | Structure | Name |
|---|---|---|
| 34 | 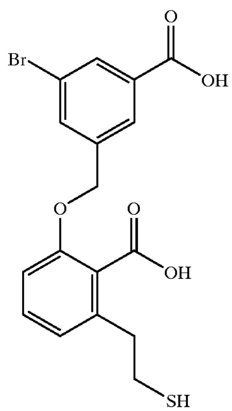 | 2-[(3-bromo-5-carboxyphenyl) methoxy]-6-(2-mercaptoethyl)-benzoic acid |
| 35 | 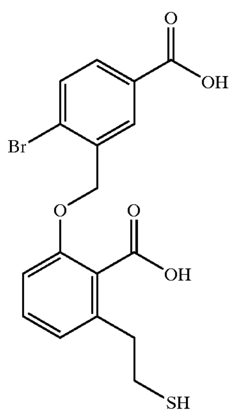 | 2-[(2-bromo-5-carboxyphenyl) methoxy]-6-(2-mercaptoethyl)-benzoic acid |
| 36 | 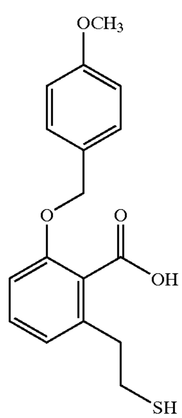 | 2-(2-mercaptoethyl)-6-[(4-methoxyphenyl)methoxy]-benzoic acid |

TABLE I-continued

| Compound No. | Structure | Name |
|---|---|---|
| 37 | 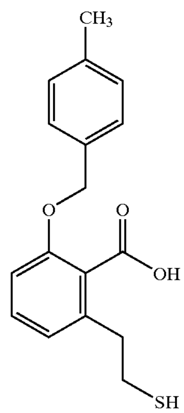 | 2-(2-mercaptoethyl)-6-[(4-methylphenyl)methoxy]-benzoic acid |
| 38 | 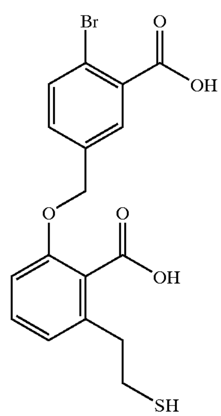 | 2-[(4-bromo-3-carboxyphenyl) methoxy]-6-(2-mercaptoethyl)-benzoic acid |
| 39 | 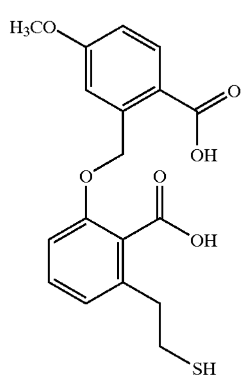 | 2-[(2-carboxy-5-methoxyphenyl) methoxy]-6-(2-mercaptoethyl)-benzoic acid |
| 40 | 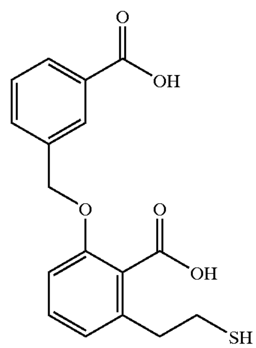 | 2-(3-carboxy-benzyloxy)-6-(2-mercapto-ethyl)-benzoic acid |

TABLE I-continued

| Compound No. | Structure | Name |
|---|---|---|
| 41 | 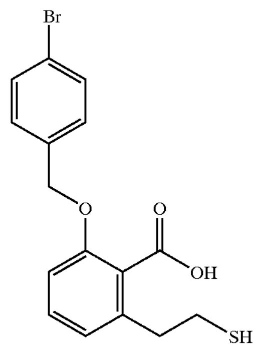 | 2-(4-bromo-benzyloxy)-6-(2-mercapto-ethyl)-benzoic acid |
| 42 | 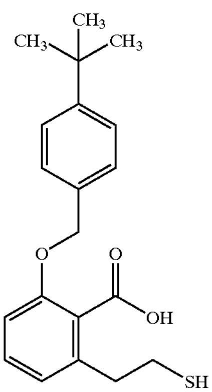 | 2-(4-tert-butyl-benzyloxy)-6-(2-mercapto-ethyl)-benzoic acid |
| 43 | 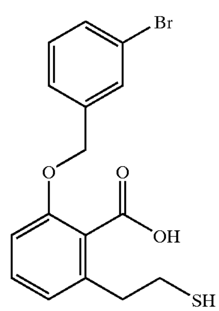 | 2-(3-bromo-benzyloxy)-6-(2-mercapto-ethyl)-benzoic acid |
| 44 | 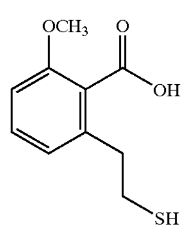 | 2-(2-mercapto-ethyl)-6-methoxy-benzoic acid |

TABLE I-continued

| Compound No. | Structure | Name |
|---|---|---|
| 45 | 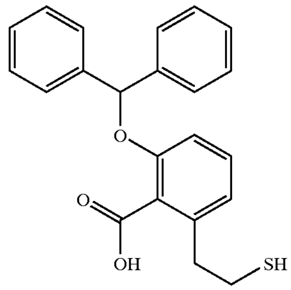 | 2-benzhydryloxy-6-(2-mercapto-ethyl)-benzoic acid |
| 46 | 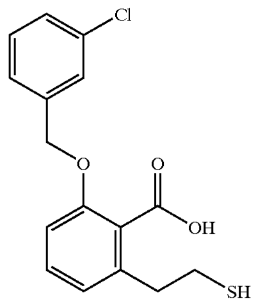 | 2-(3-chloro-benzyloxy)-6-(2-mercapto-ethyl)-benzoic acid |
| 47 | 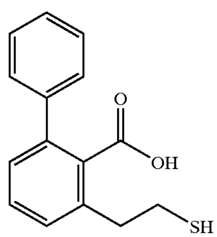 | 3-(2-mercapto-ethyl)-biphenyl-2-carboxylic acid |
| 48 | 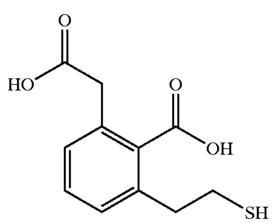 | 2-carboxymethyl-6-(2-mercapto-ethyl)-benzoic acid |

The compounds of the invention possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base and then separation of the mixture of diastereoisomers by crystallization followed by liberation of the optically active bases from these salts. Examples of useful acids include tartaric, diacetyltartaric, dibenzoyltartaric, ditoluoyltartaric, and camphorsulfonic acids.

A different process for separating optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means, such as chromatography, distillation, crystallization or sublimation, and then hydrolyzed to deliver the enantiomerically pure compound. In some cases, hydrolysis to the parent optically active drug prior to dosing the patient is unnecessary since the compound can behave as a prodrug. The optically active compounds of the present invention can likewise be obtained by utilizing optically active starting materials.

It is understood that the compounds of the invention encompass optical isomers as well as racemic and non-racemic mixtures.

METHODS OF THE INVENTION
Methods for Inhibiting NAALADase Enzyme Activity

The present invention relates to a method for inhibiting NAALADase enzyme activity in an animal or a mammal, comprising administering to said animal or mammal an effective amount of a compound of the invention, as defined above.

Methods for Treating Glutamate Abnormalities

The present invention further relates to a method for treating a glutamate abnormality in an animal or a mammal, comprising administering to said animal or mammal an effective amount of a compound of the invention, as defined above.

Glutamate abnormalities to be treated may include compulsive disorder, stroke, demyelinating disease, schizophrenia, Parkinson's disease, ALS, diabetic neuropathy, pain, anxiety, anxiety disorder, memory impairment, and glaucoma. Preferably, the compulsive disorder is alcohol, nicotine or cocaine dependence.

Stroke patients often experience a significant temporal delay between the onset of ischemia and the initiation of therapy. Thus, there is a need for neuroprotectants with a long therapeutic window of opportunity. It is expected that the compounds of the invention have a therapeutic window of opportunity of at least 1 hour. Accordingly, when the glutamate abnormality is stroke, the compound of the invention may be administered to said animal or mammal for up to 60 minutes, 120 minutes or more following onset of stroke.

Without being bound to any particular mechanism of action, preferred compounds of the present invention are expected to be those that block glutamate release presynaptically without interacting with post-synaptic glutamate receptors. Such compounds would be devoid of the behavioral toxicities associated with post-synaptic glutamate antagonists.

Methods for Effecting Neuronal Activities

The present invention further relates to a method for effecting a neuronal activity in an animal or a mammal, comprising administering to said animal or mammal an effective amount of a compound of the invention, as defined above.

The neuronal activity that is effected by the inventive method may be stimulation of damaged neurons, promotion of neuronal regeneration, prevention of neurodegeneration or treatment of a neurological disorder.

Preferably, the neuronal activity is treatment of a neurological disorder that is pain, neuropathy, traumatic brain injury, physical damage to spinal cord, stroke associated with brain damage, a demyelinating disease, or a neurological disorder relating to neurodegeneration.

Examples of neurological disorders that are treatable by the methods of the present invention include without limitation: trigeminal neuralgia; glossopharyngeal neuralgia; Bell's Palsy; myasthenia gravis; muscular dystrophy; ALS; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; diabetic neuropathy; pain; Alzheimer's disease; and Parkinson's disease.

The inventive method is particularly useful for treating a neurological disorder selected from the group consisting of peripheral neuropathy caused by physical injury or disease state, diabetic neuropathy, HIV-, chemical-, and vitamin-induced neuropathies, pain, traumatic brain injury, physical damage to spinal cord, stroke associated with brain damage, demyelinating disease and neurological disorder relating to neurodegeneration.

When the neurological disorder is pain, the compound of the invention is preferably administered in combination with an effective amount of morphine.

The inventive method is particularly useful for treating neuropathic pain, e.g., HIV-, chemical-, and vitamin-induced neuropathic pain.

Examples of neurological disorders relating to neurodegeneration include Alzheimer's disease, Parkinson's disease, and ALS.

Methods for Treating Prostrate Diseases

The present invention further relates to a method for treating a prostate disease in an animal or a mammal, comprising administering to said animal or mammal an effective amount of a compound of the invention, as defined above. A preferred prostate disease is prostate cancer.

Methods for Treating Cancers

The present invention further relates to a method for treating cancer in an animal or a mammal, comprising administering to said animal or mammal an effective amount of a compound of the invention, as defined above.

Preferred cancers to be treated are those in tissues where NAALADase resides, including without limitation the brain, kidney and testis.

Methods for Inhibiting Angiogenesis

The present invention further relates to a method for inhibiting angiogenesis in an animal or a mammal, comprising administering to said animal or mammal an effective amount of a compound of the invention, as defined above.

Angiogenesis may be necessary for fertility or metastasis of cancer tumors, or may be related to an angiogenic-dependent disease. Thus, the inventive methods may also be useful for treating an angiogenic-dependent disease including, without limitation, rheumatoid arthritis, cardiovascular diseases, neovascular diseases of the eye, peripheral vascular disorders, dermatologic ulcers and cancerous tumor growth, invasion, or metastasis.

Methods for Effecting TGF-β Activity

The present invention further relates to a method for effecting a TGF-β activity in an animal or a mammal, comprising administering to said animal or mammal an effective amount of a compound of the invention, as defined above.

Effecting a TGF-β activity includes increasing, reducing or regulating TGF-β levels, and treating TGF-β abnormalities. Examples of TGF-β abnormalities to be treated include neurodegenerative disorders, extra-cellular matrix formation disorders, cell-growth related diseases, infectious diseases, immune related diseases, epithelial tissue scarring, collagen vascular diseases, fibroproliferative disorders, connective tissue disorders, inflammation, inflammatory diseases, respiratory distress syndrome, infertility and diabetes.

Typical neurodegenerative disorders to be treated include neural tissue damage resulting from ischemia reperfusion injury, myelination and neurodegeneration.

Typical cell-growth related disorders to be treated include those affecting kidney cells, hematopoietic cells, lymphocytes, epithelial cells and endothelial cells.

Typical infectious diseases to be treated include those caused by a macrophage pathogen, particularly a macrophage pathogen selected from the group consisting of bacteria, yeast, fungi, viruses, protozoa, *Trypanosoma cruzi*, *Histoplasma capsulatum*, *Candida albicans*, *Candida parapsilosis*, *Cryptococcus neoformans*, Salmonella, Pneumocystis, Toxoplasma, Listeria, Mycobacteria, Rickettsia and Leishmania. Mycobacteria include without limitation *Mycobacterium tuberculosis* and *Mycobacterium leprae*. Toxoplasma includes without limitation *Toxoplasma gondii*. Rickettsia includes without limitation *R. prowazekii*, *R. coronii*, and *R. tsutsugamushi*.

Other examples of infectious diseases to be treated include single or multiple cutaneous lesions, mucosal disease, Chagas' disease, acquired immunodeficiency syndrome ("AIDS"), toxoplasmosis, leishmaniasis, trypanosomiasis, shistosomiasis, cryptosporidiosis, Mycobacterium avium infections, *Pneumocystis carinii* pneumonia and leprosy.

Typical immune related diseases to be treated include autoimmune disorders; impaired immune function; and immunosuppression associated with an infectious disease, particularly, trypanosomal infection, viral infection, human immunosuppression virus, human T cell lymphotropic virus ("HTLV-1"), lymphocytic choriomeningitis virus, or hepatitis.

Typical collagen vascular diseases to be treated include progressive systemic sclerosis ("PSS"), polymyositis, scleroderma, dermatomyositis, eosinophilic fascitis, morphea, Raynaud's syndrome, interstitial pulmonary fibrosis, scleroderma and systemic lupus erythematosus.

Typical fibroproliferative disorders to be treated include diabetic nephropathy, kidney disease, proliferative vitreoretinopathy, liver cirrhosis, biliary fibrosis, and myelofibrosis. Especially preferred kidney diseases include mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Typical connective tissue disorders to be treated include scleroderma, myelofibrosis, and hepatic, intraocular and pulmonary fibrosis.

Typical inflammatory diseases to be treated are associated with PSS, polymyositis, scleroderma, dermatomyositis, eosinophilic fascitis, morphea, Raynaud's syndrome, interstitial pulmonary fibrosis, scleroderma, systemic lupus erythematosus, diabetic nephropathy, kidney disease, proliferative vitreoretinopathy, liver cirrhosis, biliary fibrosis, myelofibrosis, mesangial proliferative glomerulonephritis, crescentic glomerulonephritis, diabetic neuropathy, renal interstitial fibrosis, renal fibrosis in transplant patients receiving cyclosporin, or HIV-associated nephropathy.

Without being limited to any particular mechanism of action, preferred compounds of the present invention treat inflammatory diseases by regulating TGF-β and/or inhibiting myeloperoxidase.

Other uses associated with the inventive compounds' TGF-β regulating properties include:

stimulating growth of tissue, glands or organs, particularly growth that would enhance milk production or weight gain;

stimulating cell proliferation, particularly proliferation of fibroblasts, mesenchymal cells or epithelial cells;

inhibiting cell growth, particularly of epithelial cells, endothelial cells, T and B lymphocytes and thymocytes;

inhibiting expression of adipose, skeletal muscle and hematopoietic phenotypes, neoplasms, non-cytocidal viral or other pathogenic infections and autoimmune disorders;

mediating disease resistance and susceptibility;

suppressing cellular immune response;

inhibiting scar tissue formation, preferably in skin or other epithelial tissue that has been damaged by wounds resulting from accidental injury, surgical operations, trauma-induced lacerations or other trauma, or wounds involving the peritoneum for which the excessive connective tissue formation is abdominal adhesions;

increasing the effectiveness of a vaccine, particularly a vaccine for an allergy towards, for example, dust or hayfever; and inhibiting polyp formation.

Methods for Treating a Retinal Disorder

The present invention further relates to a method of treating a retinal disorder comprising administering an effective amount of a NAALADase inhibitor to an animal in need of such treatment.

Diagnostic Methods and Kits

The compounds of the present invention are useful for in vitro and in vivo diagnostic methods for detecting diseases, disorders and conditions where NAALADase levels are altered including, without limitation, neurological disorders, glutamate abnormalities, neuropathy, pain, compulsive disorders, prostate diseases, cancers, TGF-β abnormalities, and glaucoma.

Accordingly, the present invention also relates to a method for detecting a disease, disorder or condition where NAALADase levels are altered, comprising:

(i) contacting a sample of bodily tissue or fluid with a compound of the invention, as defined above, wherein said compound binds to any NAALADase in said sample; and (ii) measuring the amount of any NAALADase bound to said sample, wherein the amount of NAALADase is diagnostic for said disease, disorder or condition.

Examples of bodily tissues and fluids include, without limitation, prostate tissue, ejaculate, seminal vesicle fluid, prostatic fluid, urine, blood, saliva, tears, sweat, lymph and sputum.

The compound may be labeled with a marker using techniques known in the art. Useful markers include, without limitation, enzymatic markers and imaging reagents. Examples of imaging reagents include radiolabels such as $^{131}I$, $^{111}In$, $^{123}I$, $^{99}Tc$, $^{32}P$, $^{125}I$, $^{3}H$, and $^{14}C$; fluorescent labels such as fluorescein and rhodamine; and chemiluminescers such as luciferin.

The amount of NAALADase can be measured using techniques known in the art including, without limitation, assays (such as immunometric, calorimetric, densitometric, spectrographic and chromatographic assays) and imaging techniques (such as magnetic resonance spectroscopy ("MRS"), magnetic resonance imaging ("MRI"), single-photon emission computed tomography ("SPECT"), and positron emission tomography ("PET")).

The present invention further relates to a diagnostic kit for detecting a disease, disorder or condition where NAALADase levels are altered. The diagnostic kit includes a compound of the invention, as defined above, labeled with a marker. The diagnostic kit may further include buffering agents, agents for reducing background interference, control reagents and/or apparatus for conducting the test.

The present invention further relates to a method for detecting a disease, disorder or condition where NAALADase levels are altered in an animal or a mammal, comprising:

(i) labeling a compound of the invention, as defined above, with an imaging reagent;

(ii) administering to said animal or mammal an effective amount of the labeled compound;

(iii) allowing said labeled compound to localize and bind to NAALADase present in said animal or mammal; and (iv) measuring the amount of NAALADase bound to said labeled compound, wherein the amount of NAALADase is diagnostic for said disease, disorder or condition.

The amount of NAALADase can be measured in vivo using known imaging techniques, as described above.

INCORPORATION BY REFERENCE

The relationship between NAALADase inhibitors and glutamate, and the effectiveness of NAALADase inhibitors in treating and detecting various diseases, disorders and conditions have been discussed in U.S. Pat. Nos. 5,672,592; 5,795,877; 5,804,602; 5,824,662; 5,863,536; 5,977,090; 5,981,209; 6,011,021; 6,017,903; 6,025,344; 6,025,345; 6,046,180; 6,228,888 and 6,265,609; International Publication Nos. WO 00/01668 and WO 00/38785; provisional U.S. patent application Ser. No. 60/261,754; and other references generally known in the art. The present inventors hereby incorporate by reference, as though set forth herein in full, the entire contents of the aforementioned patents, patent applications, and publications, particularly their discussions, figures and data regarding the effectiveness of NAALADase inhibitors in inhibiting angiogenesis, in effecting TGF-β activity, in diagnosing diseases, and in treating ischemia, spinal cord injury, demyelinating diseases, Parkinson's disease, ALS, alcohol dependence, nicotine dependence, cocaine dependence, prostate disease, cancer, neuropathy, pain, schizophrenia, anxiety, anxiety disorder, and memory impairment. The present inventors have discovered that the inventive compounds are effective NAALADase inhibitors. Thus, the inventive compounds are expected to have the same uses as the NAALADase inhibitors disclosed in the patents, patent applications, and publications that are incorporated by reference.

Pharmaceutical Compositions of the Invention

The present invention also relates to a pharmaceutical composition comprising an effective amount of a compound of the invention or a pharmaceutically acceptable equivalent; and a pharmaceutically acceptable carrier.

Preferably, the compound of the invention is present in an effective amount for inhibiting NAALADase enzyme activity or angiogenesis, effecting a neuronal activity or TGF-β activity, or treating a glutamate abnormality, neuropathy, pain, prostate disease, or cancer in an animal or a mammal.

Route of Administration

In the inventive methods, the compounds will generally be administered to a patient in the form of a pharmaceutical formulation. Such formulation preferably includes, in addition to the active agent, a physiologically acceptable carrier and/or diluent. The compounds may be administered locally or systemically by any means known to an ordinarily skilled artisan. For example, the compounds may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intraarterial, intramuscular, intraperitoneal, intrathecal, intraventricular, intrasternal, intracranial or intraosseous injection and infusion techniques. The exact administration protocol will vary depending upon various factors including the age, body weight, general health, sex and diet of the patient; the determination of specific administration procedures would be routine to an ordinarily skilled artisan.

To be effective therapeutically as central nervous system targets, the compounds should readily penetrate the blood-brain barrier when peripherally administered. Compounds that cannot penetrate the blood-brain barrier can be effectively administered by an intraventricular route or by other methods recognized in the art. See, for example, U.S. Pat. Nos. 5,846,565; 5,651,986; and 5,626,862, incorporated herein by reference.

Dosage

The compounds and compositions of the present invention may be administered by a single dose, multiple discrete doses, or continuous infusion. The compounds are well suited to continuous infusion. Pump means, particularly subcutaneous pump means, are preferred for continuous infusion.

Dose levels on the order of about 0.001 to about 10,000 mg/kg of the active ingredient compound are useful in the treatment of the above conditions, with preferred levels being about 0.1 to about 1,000 mg/kg, and more preferred levels being about 1 to about 100 mg/kg. The specific dose level for any particular patient will vary depending upon a variety of factors, including the activity and the possible toxicity of the specific compound employed; the age, body weight, general health, sex, and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Aministration Regimen

For the methods of the present invention, any administration regimen well known to an ordinarily skilled artisan for regulating the timing and sequence of drug delivery can be used and repeated as necessary to effect treatment. Such regimen may include pretreatment and/or co-administration with additional therapeutic agents.

Co-Administration with Other Treatments

The compounds and compositions of the present invention may be used alone or in combination with one or more additional agent(s) for simultaneous, separate or sequential use.

The additional agent(s) may be any therapeutic agent(s) known to an ordinarily skilled artisan, including without limitation: one or more compound(s) of the invention; steroids, for example, hydrocortisones such as methylprednisolone; anti-inflammatory or anti-immune drugs, such as methotrexate, azathioprine, cyclophosphamide or cyclosporin A; interferon-β; antibodies, such as anti-CD4 antibodies; agents which can reduce the risk of a second ischemic event, such as ticlopidine; chemotherapeutic agents; immunotherapeutic compositions; electromagnetic radiosensitizers; and morphine.

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying, and pH buffering agents.

Preparations of Compounds

The compounds of the present invention can be readily prepared by standard techniques of organic chemistry, utilizing the general synthetic pathways depicted below in Schemes I, II, III, and IV. Precursor compounds are either commercially available or may be prepared by methods known to a person of skill in the art.

SCHEME I

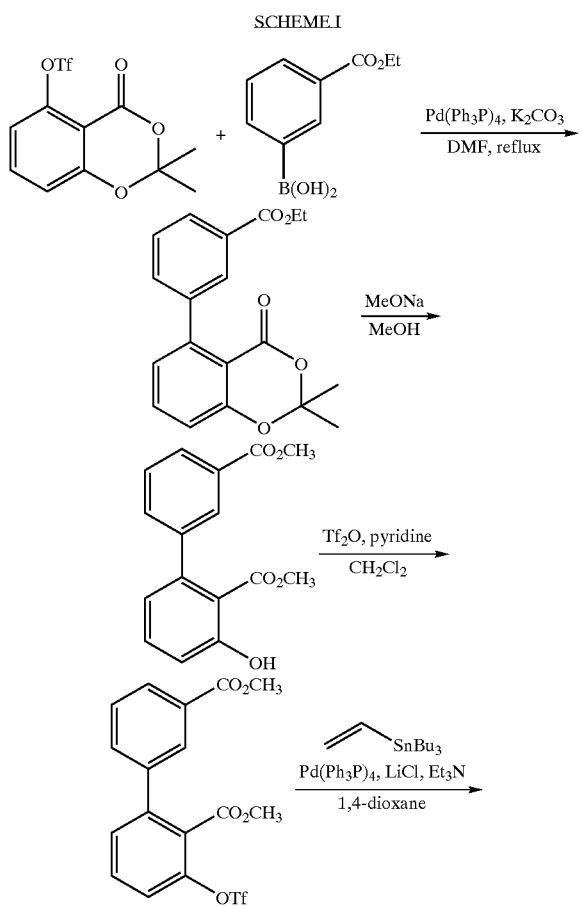

SCHEME II

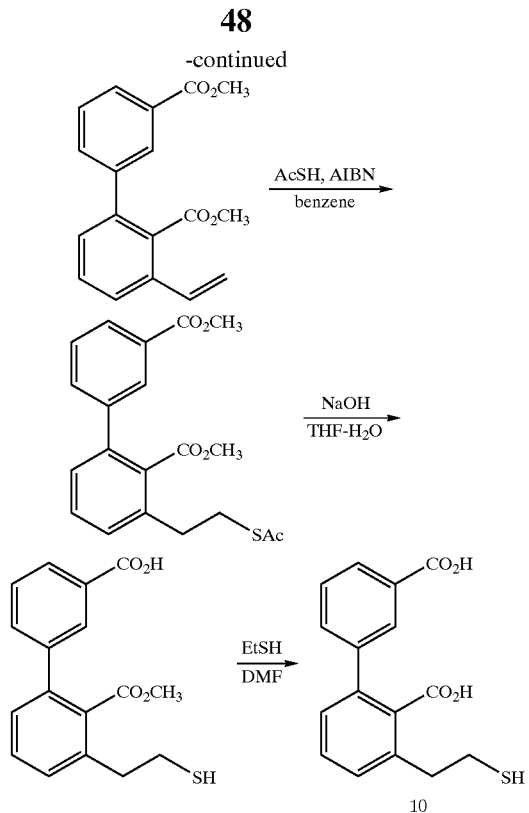

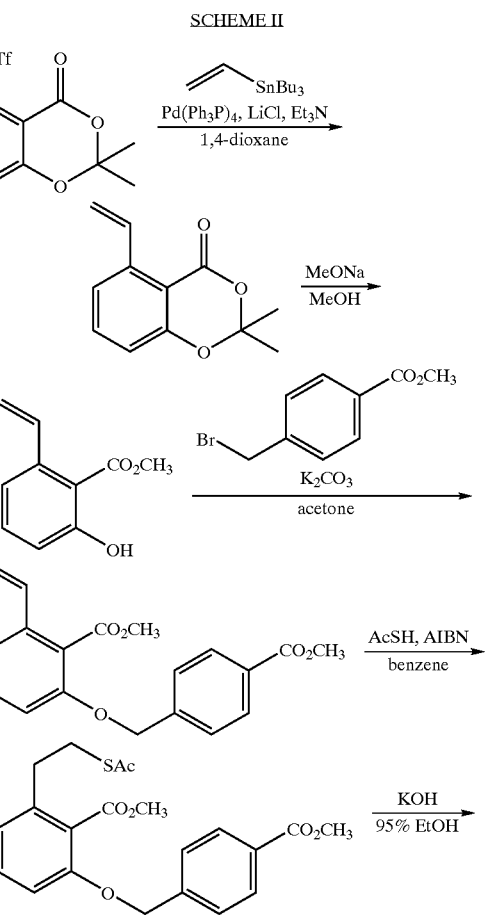

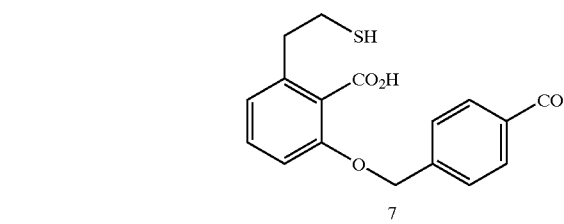
SCHEME III
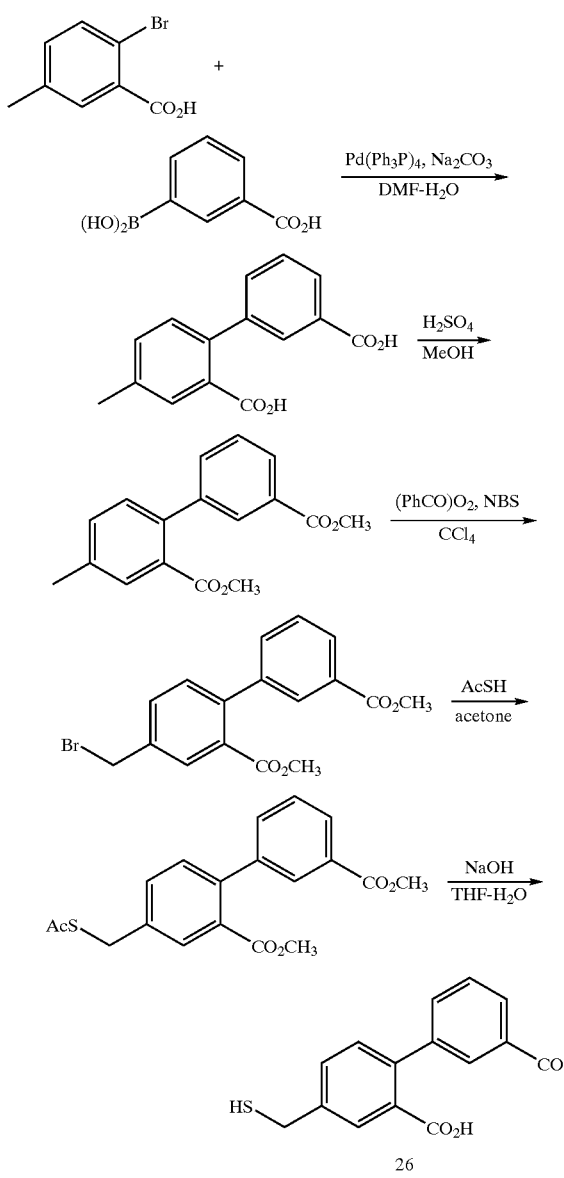
SCHEME IV
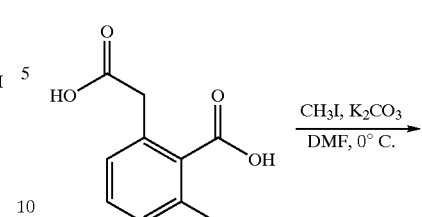
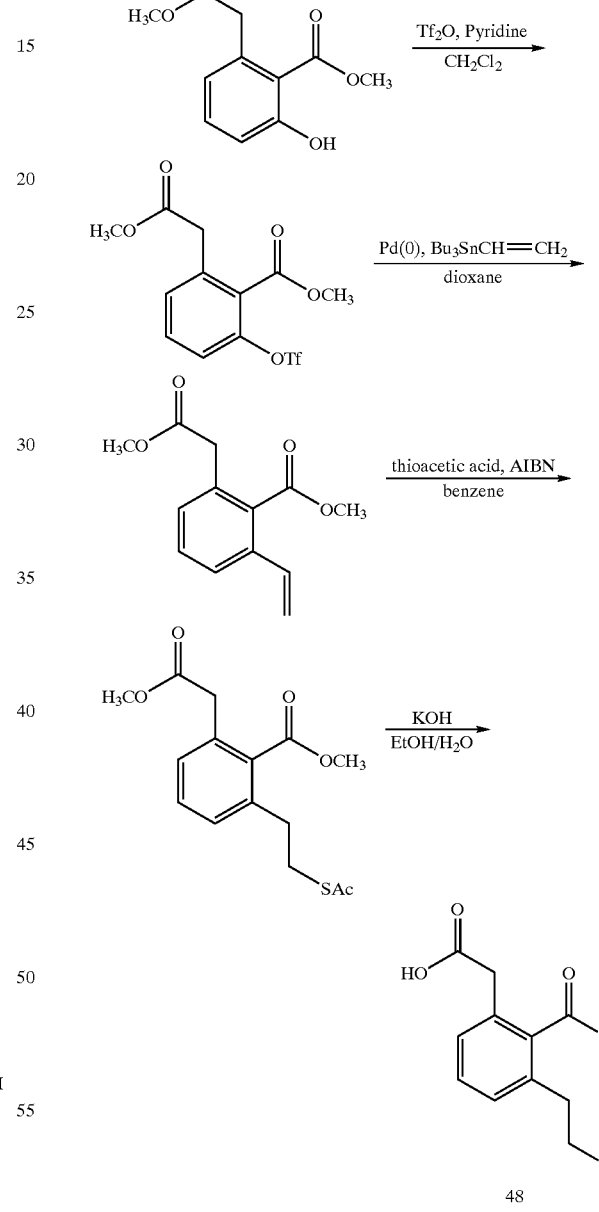

EXAMPLES

The following examples are illustrative of the present invention and are not intended to be limitations thereon. Unless otherwise indicated, all percentages are based upon 100% by weight of the final composition.

Example 1

Procedure for the Synthesis of 3-(2-Mercaptoethyl)-[1,1'-Biphenyl]-2,3'-Dicarboxylic Acid (10) (Scheme I)

3-(2,2-Dimethyl-4-oxo-4H-1,3-benzodioxin-5-yl)-benzoic acid, ethyl ester

To a solution of 2,2-dimethyl-5-trifluoromethane-sulfonyloxy-4H-1,3-benzodioxin-4-one (2.0 g, 5.8 mmol), 3-ethoxycarbonylphenylboronic acid (1.34 g, 6.9 mmol) and anhydrous $K_2CO_3$ powder (2.61 g, 18.9 mmol) in DMF (30 mL) was added tetrakis(triphenylphosphine)palladium (0.202 g, 0.175 mmol). The mixture was heated at reflux for 2 h. The reaction mixture was allowed to cool to room temperature ("rt") and 1 N HCl (25 mL) was added. The mixture was extracted with EtOAc (3×25 mL). The combined extracts were washed with water and brine, then dried over $MgSO_4$, filtered, and concentrated. The crude material was purified by flash chromatography (1:15 EtOAc/hexanes) to afford 3-(2,2-dimethyl4-oxo4H-1,3-benzodioxin-5-yl)-benzoic acid, ethyl ester (1.2 g, 63%) as a white solid: $^1$H NMR (CDCl$_3$) δ1.39 (t, J=7.1 Hz, 3H), 1.80 (s, 6H), 4.39 (q, J=7.0 Hz, 2H), 7.01 (d, J=8.0 Hz, 2H), 7.47–7.57 (m, 3H), 8.00 (t, J=1.5 Hz, 1H) 8.07 (dt, J=7.5, 1.5 Hz, 1H).

3-Hydroxy-[1,1'-biphenyl]-2,3'-dicarboxylic acid, dimethyl ester

To a solution of 3-(2,2-dimethyl-4-oxo4H-1,3-benzodioxin-5-yl)-benzoic acid, ethyl ester (1.4 g, 4.3 mmol) in methanol (10 mL) was added sodium methoxide (0.5 M in methanol, 25 mL) at 0° C. The solution was stirred at rt for 15 min. The reaction was quenched by addition of 1 N HCl (30 mL) and extracted with EtOAc (3×30 mL). The combined organic extracts were dried over $MgSO_4$ and concentrated to afford 3-hydroxy-[1,1'-biphenyl]-2,3'-dicarboxylic acid, dimethyl ester (1.2 g, 95%) as a yellow solid: $^1$H NMR (CDCl$_3$) δ3.43 (s, 3H), 3.93 (s, 3H), 6.79 (dd, J=7.5, 0.9 Hz, 1H) 7.04 (dd, J=7.5, 0.9 Hz, 1H), 7.43 (m, 3H), 7.93 (m, 1H), 8.02 (dm, J=7.0 Hz, 1H), 10.8 (s, 1H).

3-Trifluoromethanesulfonyloxy-[1,1'-biphenyl]-2,3'-dicarboxylic acid, dimethyl ester To a solution of 3-hydroxy-[1,1'-biphenyl]-2,3'-dicarboxylic acid, dimethyl ester (1.1 g, 3.8 mmol) in dichloromethane (15 mL) were added pyridine (1.00 mL, 12.3 mmol) and trifluromethanesulfonic anhydride (0.90 mL, 5.4 mmol) at 0° C. The solution was stirred at 0° C. for 2 h. Aqueous 1 N HCl (20 mL) was added, and the mixture was extracted with dichloromethane (3×20 mL). The combined organic extracts were washed with water and brine, dried over $MgSO_4$, filtered, and concentrated to give 3-trifluoromethanesulfonyloxy-[1,1'-biphenyl]-2,3'-dicarboxylic acid, dimethyl ester (1.4 g, 87%) as a yellow solid: $^1$H NMR (CDCl$_3$) δ3.72 (s, 3H), 3.94 (s, 3H), 7.38–7.62 (m, 5H), 8.08 (m, 2H).

3-Ethenyl-[1,1'-biphenyl]-2,3'-dicarboxylic acid, dimethyl ester

A mixture of 3-trifluoromethanesulfonyloxy-[1,1'-biphenyl]-2,3'-dicarboxylic acid, dimethyl ester (1.3 g, 3.1 mmol), tetrakis(triphenylphosphine)palladium (0.36 g, 0.31 mmol), LiCl (0.94 g, 22.2 mmol), triethylamine (0.6 mL, 4.3 mmol) and tri-n-butyl(vinyl)tin (1.0 mL, 3.4 mmol) in 1,4-dioxane (30 mL) was heated at reflux under $N_2$ for 4 h. After cooling to rt, the mixture was filtered through a plug of silica gel and the filtrate was concentrated. Purification by flash chromatography (1:10 EtOAc/hexanes) provided 3-ethenyl-[1,1'-biphenyl]-2,3'-dicarboxylic acid, dimethyl ester (0.91 g, 99%) as a white solid: $^1$H NMR (CDCl$_3$) δ3.61 (s, 3H), 3.92 (s, 3H), 5.40 (d, J=11.1 Hz, 1H), 5.79 (d, J=17.5 Hz, 1H), 6.87 (dd, J=17.4, 11.0 Hz, 1H), 7.31 (d, J=7.5 Hz, 1H), 7.44 7.49 (m, 2H), 7.56 (dm, J=7.5 Hz, 1H), 7.62 (d, J=8.0 Hz, 1H), 8.03 (dm, J=1H), 8.08 (t, 1, J=1.5 Hz, 1H).

3-[2-(Acetylthio)ethyl]-[1,1'-biphenyl]-2,3'-dicarboxylic acid, dimethyl ester

To a solution of 3-ethenyl-[1,1'-biphenyl]-2,3'-dicarboxylic acid, dimethyl ester (0.85 g, 2.9 mmol) in benzene (10 mL) was added thioacetic acid (2.1 mL, 29.4 mmol) followed by AIBN (0.053 g, 0.32 mmol). The solution was deoxygenated for 30 min by bubbling nitrogen through the solution and then heated at reflux for 4 h. Saturated aqueous $NaHCO_3$ (20 mL) was added to the solution and the mixture was extracted with EtOAc (2×20 mL). The combined organic extracts were washed with water and brine, dried over $MgSO_4$, filtered, and concentrated. The residue was purified by flash chromatography (1:12 EtOAc/hexanes) to give 3-[2-(acetylthio)ethyl]-[1,1'-biphenyl]-2,3'-dicarboxylic acid, dimethyl ester (0.51 g, 48%) as an off white solid: $^1$H NMR (CDCl$_3$) δ2.35 (s, 3H), 2.93 (m, 2H), 3.14 (m, 2H), 3.62 (s, 3H), 3.93 (s, 3H), 7.29 (dd, J=7.6, 0.9 Hz, 1H), 7,35 (dd, J=7.5, 0.8 Hz, 1H), 7.44 (d, J=7.6 Hz, 1H), 7.48 (d, J=7.5 Hz, 1), 7.55 (dt, J=8.0, 1.5 Hz, 1H), 8.03 (dt, J=7.9, 1.5 Hz, 1H), 8.07 (t, J=1.5 Hz, 1H).

3-(2-Mercaptoethyl)-[1,1'-biphenyl]-2,3'-dicarboxylic acid, 2-methyl ester

To a deoxygenated solution of 3-[2-(acetylthio)ethyl]-[1,1'-biphenyl]-2,3'-dicarboxylic acid, dimethyl ester (0.50 g, 1.34 mmol) in THF (3.5 mL) was added a deoxygenated solution of NaOH (0.38 g, 9.4 mmol) in water (3.5 mL). The mixture was stirred overnight, and 1 N HCl (20 mL) was added. The mixture was extracted with EtOAc (3×20 mL). The combined organic extracts were washed with water and brine, dried over $MgSO_4$, filtered, and concentrated to afford 3-(2-mercaptoethyl)-[1,1'-biphenyl]-2,3'-dicarboxylic acid, 2-methyl ester (0.35 g, 83%) as an off white solid: $^1$H NMR (CDCl$_3$) δ1.46 (t, J=8.0 Hz, 1H), 2.83 (m, 2H), 3.00 (m, 2H), 3.60 (s, 3H), 7.33–7.31 (m, 2H), 7.46 (t, J=7.7 Hz, 1H), 7.52 (t, J=7.7 Hz, 1H), 7.61 (dm, J=7.9 Hz, 1H), 8.10 (dm, J=7.9 Hz, 1H), 8.14 (m, 1H).

3-(2-Mercaptoethyl)-[1,1'-biphenyl]-2,3'-dicarboxylic acid (10)

To a deoxygenated suspension of sodium ethanethiolate (0.135 g, 1.60 mmol) in DMF (0.5 mL) was added a solution of 3-(2-mercaptoethyl)-[1,1'-biphenyl]-2,3'-dicarboxylic acid, 2-methyl ester (0.10 g, 0.32 mmol) in DMF (0.5 mL). Argon was bubbled through the mixture for 10 min. The reaction was heated at 100° C. for 1 h and 200° C. for another hour. After the mixture cooled to rt, the reaction was quenched with 1 N HCl (20 mL) and was extracted with EtOAc (3×20 mL). The combined organic extracts were washed with water and brine, dried over $MgSO_4$, filtered, and concentrated to afford 3-(2-mercaptoethyl)-[1,1'-biphenyl]-2,3'-dicarboxylic acid (0.055 g, 57%) as a white solid: $^1H$ NMR ($CDCl_3$) δ1.51 (t, J=8.0 Hz, 1H), 2.87–2.93 (m, 2H), 3.12–3.08 (m, 2H), 7.37 (m, 2H), 7.57–7.47 (m, 2H), 7.70 (dm, J=7.9 Hz, 1H), 7.98 (dm, J=7.8 Hz, 1H), 8.30 (m, 1H); $^{13}C$ NMR ($CDCl_3$) δ26.2, 38.8, 128.1, 129.3, 129.7, 129.8, 129.9 (2C), 130.5, 133.3, 134.4, 137.7, 139.1, 141.2, 172.3, 176.9. Anal. Calcd for $C_{16}H_{14}O_4S$: C, 63.56; H, 4.67; S, 10.61. Found: C, 63.65; H, 4.88; S, 10.33.

Example 2

Procedure for the Synthesis of 2-[(4-Carboxyphenyl)Methoxyl]-6-(2-Mercaptoethyl)-Benzoic Acid (7) (Scheme II)

5-Ethenyl-2,2-dimethyl-4H-1,3-benzodioxin-4-one

A mixture of 2,2-dimethyl-5-trifluoromethanesulfonyloxy-4H-1,3-benzodioxin4-one (9.90 g, 30.3 mmol), tributyl(vinyl)tin (10.10 g, 31.9 mmol), lithium chloride (8.70 g, 205 mmol), and triethylamine (5.0 mL, 36.0 mmol) in 1,4-dioxane (300 mL) was deoxygenated by bubbling nitrogen through the mixture for 1 h. To the mixture was added tetrakis(triphenylphosphine)palladium (3.40 g, 2.90 mmol) and the mixture was heated at 100° C. for 3 h. The mixture was allowed to cool to rt and was filtered. The filtrate was concentrated and purified by flash chromatography (1:12, EtOAc/hexanes) to provide 5-ethenyl-2,2-dimethyl-4H-1,3-benzodioxin-4-one (5.00 g, 81%) as a yellow oil: $^1H$ NMR: ($CDCl_3$) δ1.72 (s, 6H), 5.43 (dd, J=11.0, 1.3 Hz, 1), 5.72 (dd, J=17.5, 1.3 Hz, 1 Hz, 1H), 6.89 (d, J=8.0 Hz, 1H), 7.27 (d, J=8.0 Hz, 1H), 7.47 (t, J=8.0 Hz, 1H), 7.73 (dd, J=17.5, 11.0 Hz, 1H).

2-Ethenyl-6-hydroxybenzoic acid, methyl ester

To 5-ethenyl-2,2-dimethyl-4H-1,3-benzodioxin-4-one (4.01 g, 19.6 mmol) was added 0.5 M sodium methoxide in methanol (85 mL, 42.5 mmol) at rt. Aqueous 1 N HCl (100 mL) was added to the solution after 15 min. The cloudy solution was extracted with ether (2×100 mL). The combined organic extracts were washed with $H_2O$ (50 mL) and brine (50 mL), dried over $Na_2SO_4$, filtered, and concentrated to afford 2-ethenyl-6-hydroxybenzoic acid, methyl ester (2.0 g, 57%) as a yellow oil. This material was used without further purification in the next step: $^1H$ NMR ($CDCl_3$) δ3.96 (s, 3H), 5.26 (dd, J=10.8, 1.5 Hz, 1H), 5.49 (dd, J=17.3, 1.5 Hz, 1H), 6.95 (m, 2H), 7.23–7.39 (m, 2H), 11.12 (s, 1H).

2-Ethenyl-6-[4-(methoxycarbonyl)phenyl]methoxy-benzoic acid, methyl ester

To a stirred solution of the above material (0.500 g, 2.8 mmol) in acetone (10 mL) were added $K_2CO_3$ (1.50 g, 10.9 mmol) and methyl 4-(bromomethyl)benzoate (0.71 g, 3.10 mmol) at rt. The mixture was stirred under nitrogen for 3 h and filtered. The filtrate was concentrated and residue was purified by flash chromatography (1:10 EtOAc/hexanes) to provide 2-ethenyl-6-[4-(methoxycarbonyl)phenyl]methoxy-benzoic acid, methyl ester (0.73 g, 80%) as a white solid: $^1H$ NMR ($CDCl_3$) δ3.92 (s, 6H), 5.17 (s, 2H), 5.37 (dd, J=11.1, 1.0 Hz, 1H), 5.78 (dd, J=17.6, 0.9 Hz, 1H), 6.70 (dd, 1, J=17.4, 11.1 Hz, 1H), 6.83 (d, J=7.8 Hz, 1H), 7.20 (d, J=8.0 Hz, 1H) 7.29 (t, J=80 Hz, 1H), 7.46 (d, J=8.4 Hz, 2H), 8.04 (d, J=8.3 Hz, 2H).

2-[2-(Acetylthio)ethyl]-6-[4-(methoxycarbonyl)phenyl]methoxy-benzoic acid, methyl ester To a solution of 2-ethenyl-6-[4-(methoxycarbonyl)phenyl]methoxy-benzoic acid, methyl ester (0.71 g, 2.18 mmol) in benzene (10 mL) was added thioacetic acid (1.80 mL, 25.2 mmol) followed by AIBN (37 mg, 0.23 mmol). After nitrogen was bubbled through the solution for 30 min, the solution was heated at reflux for 4 h. The reaction was allowed to cool to rt and saturated $NaHCO_3$ (20 mL) was added. The mixture was extracted with EtOAc (3×20 mL). The combined organic extracts were washed with water and brine, dried over $MgSO_4$, filtered and concentrated in vacuo. The residue was purified by flash chromatography (1:10 EtOAc/hexanes) to give 2-[2-(acetylthio)ethyl]-6-[4-(methoxycarbonyl)phenyl]methoxy-benzoic acid, methyl ester (0.50 g, 60%) as a clear oil: $^1H$ NMR ($CDCl_3$) δ2.34 (s, 3H), 2.85–2.82 (m, 2H), 3.07–3.10 (m, 2H), 3.92 (s, 3H), 3.94 (s, 3H), 5.16 (s, 2H), 6.81 (d, J=8.2 Hz, 1H), 6.92 (d, J=7.7 Hz, 1H), 7.28 (t, J=8.2 Hz, 1H), 7.46 (d, J=8.3 Hz, 2H), 8.04 (d, J=8.3 Hz, 2H).

2-[(4-Carboxyphenyl)methoxy]-6-(2-mercaptoethyl)-benzoic acid (7)

To a deoxygenated solution of 2-[2-(acetylthio)ethyl]-6-[4-(methoxycarbonyl)phenyl]methoxy-benzoic acid, methyl ester (0.20 g, 0.50 mmol) in 95% EtOH (3 mL) was added a deoxygenated solution of KOH (0.463 g, 8.3 mmol) in 95% EtOH (3 mL) under nitrogen. The solution was heated at reflux overnight and quenched by addition of 1 N HCl (20 mL). The mixture was extracted with EtOAc (3×20 mL) and the combined organic extracts were washed with water and brine, then dried over $MgSO_4$, filtered, and concentrated. Purification by flash chromatography (1:1 dichloromathane/hexanes with 1% acetic acid) provided 2-[(4-carboxyphenyl)methoxy]-6-(2-mercaptoethyl)-benzoic acid (0.077 g, 46%) as a white solid: $^1H$ NMR ($CD_3OD$) δ2.75 (m, 2H), 2.92 (m, 2H), 5.22 (s, 2H), 6.93 (d, J=7.5 Hz, 1H), 6.98 (d, J=8.2 Hz, 1H), 7.30 (t, J=8.3 Hz, 1H), 7.55 (d, J=7.9 Hz, 2H), 8.02 (d, J=8.0 Hz, 2H); $^{13}C$ NMR ($CD_3OD$) δ26.5, 39.8, 71.1, 112.4, 123.9, 126.9, 128.3, 131.3, 131.7, 131.8, 139.9, 144.2, 156.7, 170.0, 172.3. Anal. Calcd for $C_{17}H_{16}O_5S$: C, 61.43; H, 4.85; S, 9.65. Found: C, 61.16; H, 4.95; S, 9.44.

Example 3

Procedure for the Synthesis of 4-Mercaptomethyl-[1,1'-Biphenyl]-2,3'-Dicarboxylic Acid (26) (Scheme III)

4-Methyl-[1,1'-biphenyl]-2,3'-dicarboxylic acid

To a solution of 2-bromo-5-methylbenzoic acid (5.00 g, 23.3 mmol) in DME (100 mL) were added 3-carboxyphenylboronic acid (3.86 g; 23.3 mmol), a solution of $Na_2CO_3$ (9.90 g, 93 mmol) in $H_2O$ and tetrakis (triphenylphosphine)palladium. The mixture was stirred at 90° C. for 4 days. The mixture was allowed to cool to rt, diluted with EtOAc (50 mL), and washed with a saturated $NaHCO_3$ solution. The aqueous layer was separated, acidified with 10% HCl, and extracted with EtOAc (3×20 mL). The combined extracts were dried over $MgSO_4$ and concentrated. The crude material was purified by column chromatography (9:1 hexanes/EtOAc 1% acetic acid) to afford 4-methyl-[1,1'-biphenyl]-2,3'-dicarboxylic acid (2.20 g, 37%) as a solid: $^1H$ NMR (DMSO-$d_6$) δ2.40 (s, 3H), 7.30 (m, 1H), 7.42 (m, 1H), 7.52–7.57 (m, 2H), 7.60 (s, 1H), 7.85 (s, 1H), 7.91–7.92 (m, 1H).

4-Methyl-[1,1'-biphenyl]-2,3'-dicarboxylic acid, dimethyl ester

To a solution of 4-methyl-[1,1'-biphenyl]-2,3'-dicarboxylic acid (2.20 g, 8.6 mmol) in methanol (150 mL) was added conc. $H_2SO_4$ (1.6 mL) and the mixture was heated at reflux overnight. The solvent was removed under a reduced pressure and the residue was partitioned between saturated aqueous $NaHCO_3$ solution and EtOAc (20 mL). The organic layer was dried over $MgSO_4$ and concentrated to give 4-methyl-[1,1'-biphenyl]-2,3'-dicarboxylic acid, dimethyl ester (2.26 g, 92%) as a crude material. This product was used for the next reaction without further purification: $^1$H NMR (DMSO-$d_6$) δ2.41 (s, 3H), 3.58 (s, 3H), 3.88 (s, 3H), 7.36–7.38 (m, 1H), 7.47–7.48 (m, 1H), 7.56–7.58 (m, 2H), 7.62 (s, 1H), 7.82 (s, 1H), 7.94–7.96 (m, 1H).

4-Bromomethyl-[1,1'-biphenyl]-2,3'-dicarboxylic acid, dimethyl ester

To a solution of 4-methyl-[1,1'-biphenyl]-2,3'-dicarboxylic acid, dimethyl ester (2.26 g, 7.9 mmol) in $CCl_4$ (50 mL) were added benzoyl peroxide (0.010 g, 0.04 mmol) and NBS (1.42 g, 8.0 mmol), and the mixture was refluxed for 3 days. The reaction mixture was allowed to cool to rt, filtered, and concentrated. The residue was purified by column chromatography (95:5 to 90:10 hexanes/EtOAc) to afford 4-bromomethyl-[1,1'-biphenyl]-2,3'-dicarboxylic acid, dimethyl ester (1.71 g, 60%): $^1$H NMR (DMSO-$d_6$) δ3.61(s, 3H), 3.88 (s, 3H), 4.84 (s, 2H), 7.48–7.50 (d, J=8.0 Hz, 1H), 7.59–7.60 (m, 2H), 7.72–7.75 (m, 1H), 7.85 (s, 1H), 7.90 (m, 1H), 7.97–7.99 (m, 1H).

4-Acetylthiomethyl-[1,1'-biphenyl]-2,3'-dicarboxylic acid, dimethyl ester

To a solution of 4-bromomethyl-[1,1'-biphenyl]-2,3'-dicarboxylic acid, dimethyl ester (1.59 g, 4.4 mmol) in acetone (75 mL) was added potassium thioacetate (0.60 g, 5.3 mmol), and the mixture was refluxed for 1 h. The mixture was allowed to cool to rt, filtered, and concentrated. The residual product was purified by column chromatography (hexanes/EtOAc, 9/1) to afford 4-acetylthiomethyl-[1,1'-biphenyl]-2,3'-dicarboxylic acid, dimethyl ester (1.21 g, 76%): $^1$H NMR (DMSO-$d_6$) δ2.39 (s, 3H), 3.60 (s, 3H), 3.88 (s, 3H), 4.23 (s, 2H), 7.42–7.44 (d, J=8.0 Hz, 1H), 7.57–7.60 (m, 3H), 7.74 (s 1H), 7.83 (s, 1H), 7.96–7.99 (m, 1H).

4-Mercaptomethyl-[1,1'-biphenyl]-2,3'-dicarboxylic acid (26)

To a solution of 4-acetylthiomethyl-[1,1'-biphenyl]-2,3'-dicarboxylic acid, dimethyl ester (0.27 g, 0.75 mmol) in deoxygenated THF was added a degassed solution of sodium hydroxide (0.12 g, 3.0 mmol) in $H_2O$ (5 mL) at rt. After 24 h, additional solution of sodium hydroxide (0.09 g) in $H_2O$ (2 mL) was added to the reaction mixture and the mixture was stirred for 24 h. The mixture was acidified with 10% HCl and extracted with EtOAc. The extract was dried over $MgSO_4$ and concentrated. The crude material was purified by column chromatography with (9:1 dichloromethane/EtOAc with 1% acetic acid) to afford 4-mercaptomethyl-[1,1'-biphenyl]-2,3'-dicarboxylic acid (0.20 g, 92%) as a white solid: $^1$H NMR (DMSO-$d_6$) δ3.10 (t, J=8.03 Hz, 1H), 3.89 (d, J=8.03 Hz, 2H), 7.43 (d, J=7.53 Hz, 1H), 7.58–7.65 (m, 3H), 7.83 (d, J=2.01 Hz, 1H), 7.92 (s, 1H), 7.97–8.00 (m, 1H). Anal. Calcd. for $C_{15}H_{12}O_4S \cdot 0.5AcOH$: C, 60.37; H, 4.43; O, 25.13; S, 10.07. Found: C, 60.28; H, 4.45; S, 10.15.

Example 4

Procedure for the Synthesis of 2-Carboxymethyl-6-(2-Mercaptoethyl)-Benzoic Acid (48) (Scheme IV)

2-Hydroxy-6-methoxycarbonylmethyl-benzoic acid methyl ester

To a solution of 2-carboxymethyl-6-hydroxy-benzoic acid (5.021 g, 25.6 mmol) in DMF (100 mL) at 0° C. were added $K_2CO_3$ (3.567 g, 25.9 mmol) and $CH_3I$ (7.9 mL, 51.9 mmol). After stirring under nitrogen at 0° C. for 4 h, the reaction was partitioned between $H_2O$ (100 mL) and ether (150 mL). The aqueous layer was acidified with 1 N HCl and extracted with EtOAc (200 mL). The EtOAc layer was dried over $MgSO_4$ and concentrated in vacuo to give the crude 2-hydroxy-6-methoxycarbonylmethyl-benzoic acid methyl ester as a colorless oil (3.2 g, 56%): $^1$H NMR (CDCl$_3$) δ3.69 (s, 3H), 3.89 (s, 5H), 6.72 (d, J=6.7 Hz, 1H), 6.96 (d, J=8.0 Hz, 1H), 7.33–7.38 (m, 1H).

2-Methoxycarbonylmethyl-6-trifluoromethanesulfonyloxy-benzoic acid methyl ester To a solution of 2-hydroxy-6-methoxycarbonylmethyl-benzoic acid methyl ester (2.51 g, 11.2 mmol) in $CH_2Cl_2$ (50 mL) at 0° C. were added triflic anhydride (3.0 mL, 17.8 mmol) and pyridine (2.40 mL, 29.7 mmol). The solution was allowed to warm to rt overnight and was concentrated in vacuo. The residue was diluted with EtOAc (100 mL), washed with 1 N HCl (25 mL), saturated aqueous $NaHCO_3$ (25 mL), $H_2O$ (25 mL), and brine (25 mL). The organic layer was dried over $MgSO_4$ and concentrated. The residue was purified by flash chromatography (10% EtOAc/hexanes) to provide 2-methoxycarbonylmethyl-6-trifluoromethanesulfonyloxy-benzoic acid methyl ester as an oil (3.5 g, 90%): $^1$H NMR (CDCl$_3$) δ3.86 (s, 3H), 4.06 (s, 2H), 4.10 (s, 3H), 7.4 (d, J=7.6 Hz, 1H), 7.50 (d, J=7.6 Hz, 1H), 7.67 (t, J=8.2 Hz, 1H).

2-Methoxycarbonylmethyl-6-vinyl-benzoic acid methyl ester

A mixture of 2-methoxycarbonylmethyl-6-trifluoromethanesulfonyloxy-benzoic acid methyl ester (2.705 g, 7.6 mmol), LiCl (2.355 g, 55.6 mmol), NEt$_3$ (1.5 mL, 10.8 mmol), Pd[P(C$_6$H$_5$)$_3$]$_4$(1.09 g, 0.94 mmol), and tributyl (vinyl)tin (2.85 mL, 9.75 mmol) in dioxane (50 mL) was heated at reflux. After 3 h, the reaction was allowed to cool to rt, filtered through a pad of silica gel and concentrated. The crude product was purified by flash chromatography on SiO$_2$(13% EtOAc/hexanes) to afford 2-methoxycarbonylmethyl-6-vinyl-benzoic acid methyl ester as a yellow solid (1.50 g, 84%): $^1$H NMR (CDCl$_3$) δ3.67 (s, 3H), 3.89 (s, 5H), 5.32 (d, J=10.9 Hz, 1H), 5.68 (d, J=17.4 Hz, 1H), 6.82 (dd, J=17.4, 10.9 Hz, 1H), 7.20 (d, J=7.1 Hz, 1H), 7.36 (m, 1H), 7.50 (d, J=7.8 Hz, 1H).

2-(2-Acetylsulfanyl-ethyl)-6-methoxycarbonylmethyl-benzoic acid methyl ester Nitrogen was bubbled through a solution of 2-methoxycarbonylmethyl-6-vinyl-benzoic acid methyl ester (1.31 g, 5.60 mmol), thioacetic acid (4.00 mL, 56.0 mmol), and AIBN (0.184 g, 1.10 mmol) in benzene (30 mL) for 3 h at rt to remove oxygen. The mixture was heated at reflux for 3 h. The solution was allowed to cool to rt and saturated aqueous $NaHCO_3$ (100 mL) was added. The mixture was extracted with EtOAc (100 mL) and the organic layer was washed with H$_2$O (100 mL) and brine (100 mL), then dried over MgSO$_4$ and concentrated in vacuo. Flash chromatography on SiO$_2$ (10% EtOAc/hexanes) provided 2-(2-acetylsulfanyl-ethyl)-6-methoxycarbonylmethyl-benzoic acid methyl ester as a yellow solid (0.555 g, 33%): $^1$H NMR (CDCl$_3$): δ2.40 (s, 3H), 2.94–2.99 (m, 2H), 3.13–3.18 (m, 2H), 3.75 (s, 3H), 3.78 (s, 2H), 3.99 (s, 3H), 7.25 (d, J=7.6 Hz, 1H), 7.32 (d, J=7.6 Hz, 1H), 7.42 (t, J=7.6 Hz, 1H).

2-Carboxymethyl-6-(2-mercapto-ethyl)-benzoic acid (48)

A deoxygenated mixture of 2-(2-acetylsulfanyl-ethyl)-6-methoxycarbonylmethyl-benzoic acid methyl ester (0.555 g, 1.77 mmol) and 6 N KOH (3 mL) in EtOH (7 mL) was heated at reflux for 18 h. After allowing to cool to rt, the mixture was partitioned between 1 N HCl (75 mL) and EtOAc (100 mL). The organic layer was washed with H$_2$O (100 mL), brine (100 mL), dried over MgSO$_4$ and concentrated in vacuo. The crude product was dissolved in ether (100 mL), filtered to remove some unidentified solid material, and concentrated to give 2-carboxymethyl-6-(2-mercapto-ethyl)-benzoic acid as a white solid (0.310 g, 73%): $^1$H NMR (CDCl$_3$) δ1.37 (t, J=8.2 Hz, 1H), 2.76 (m, 2H), 3.06 (m, 2H), 3.90 (s, 2H), 7.10 (d, J=7.6 Hz, 1H), 7.21 (d, J=6.9 Hz, 1H), 7.34 (t, J=7.8 Hz, 1H): $^{13}$C NMR (CDCl$_3$) δ27.25, 40.43, 41.83, 131.58, 131.64, 132.45, 132.55, 134.66, 141.41, 176.14, 179.40. Anal. Calcd for C, H$_{11}$H$_{12}$O$_4$S: C, 54.99; H, 5.03; S, 13.35. Found: C, 55.20; H, 5.26; S, 13.32.

Example 5A

In Vitro Inhibition of NAALADase Activity

Various compound of the invention were tested for in vitro inhibition of NAALADase activity, and the results are provided below in Table II.

TABLE II

| Compound No. | IC$_{50}$ |
|---|---|
| 1 | 613 |
| 2 | 9170 |
| 3 | 71.5 |
| 4 | 380 |
| 5 | 215 |
| 6 | 84.5 |
| 7 | 89.8 |
| 8 | 11.5 |
| 9 | 28.8 |
| 10 | 84.8 |
| 11 | 188 |
| 12 | 2580 |
| 13 | 266 |
| 14 | 160 |
| 15 | 23.7 |
| 16 | 4.28 |
| 17 | 7 |
| 18 | 10.5 |
| 19 | 2.65 |
| 20 | 18 |
| 21 | 1150 |
| 26 | 24.3 |
| 27 | 85 |
| 28 | 3200 |
| 29 | 6050 |
| 30 | 3780 |
| 31 | 100000 |
| 32 | 25 |
| 33 | 95 |

TABLE II-continued

| Compound No. | IC$_{50}$ |
|---|---|
| 34 | 0.9 |
| 35 | 1.2 |
| 36 | 100 |
| 37 | 70 |
| 38 | 0.8 |
| 39 | 40 |
| 40 | 1 |
| 41 | 1250 |
| 42 | 300 |
| 43 | 104 |
| 44 | 954 |
| 45 | 35200 |
| 46 | 12200 |
| 47 | 75400 |
| 48 | 43 |

Protocol for Assaying In Vitro Inhibition of NAALADase Activity

The following were combined in assay tubes: 100 μL of 10 mM CoCl$_2$, 250 μL of 200 mM Tris chloride, 100 μL tissue, 100 μL of 10 mM NAALADase inhibitor in Bakers H$_2$O, and Bakers H$_2$O to make a total volume of 950 μL. Each assay tube was then incubated for 10 minutes in a 37° C. water bath. 50 μL of 3-H-NAAG was then added to each assay tube and incubated for an additional 15 minutes in a 37° C. water bath. The assay was stopped by adding 1.0 ml of 0.1 M sodium phosphate.

Glutamate released by the action of the NAALADase enzyme was separated from the assay solution using an anion exchange resin. The resin was equilibrated to 25° C., 2.0 ml of the resin was added to a Pasteur pipette pre-loaded with a single glass bead, and each column was washed twice with distilled H$_2$O. A column was placed over a scintillation vial and 200 μL of an assay sample was loaded onto the column. After draining, glutamate was eluted using two 1.0 ml washes of 1 M formic acid. After addition of 10 ml of scintillation cocktail, each sample was counted for 2 minutes on a scintillation counter.

Example 5B

In Vitro Assay on Ischemia

To examine the in vitro effect of the compounds of the invention on ischemia, cortical cell cultures were treated with various compounds of the invention during an ischemic insult utilizing potassium cyanide and 2-deoxyglucose, and for one hour thereafter. For a description of the experimental method used, see Vornov et al., J. Neurochem., Vol. 65, No. 4, pp. 1681–1691 (1995). The results are provided below in Table III. Neuroprotective effect is expressed as EC$_{50}$, the concentration of the compound, which is required to cause a 50% reduction in glutamate toxicity following an ischemic insult.

TABLE III

| Compound No. | EC$_{50}$ |
|---|---|
| 1 | 846 |
| 3 | 10000 |
| 4 | 9600 |
| 6 | 84 |
| 7 | 96 |

TABLE III-continued

| Compound No. | EC$_{50}$ |
|---|---|
| 8 | 29 |
| 9 | 19 |
| 25 | 2000 |
| 26 | 151 |
| 27 | 728 |
| 29 | 2400 |
| 30 | 619 |

Example 6

Effect of NAALADase Inhibition on TGF-β in In Vitro Ischemia Model

Figure 2:
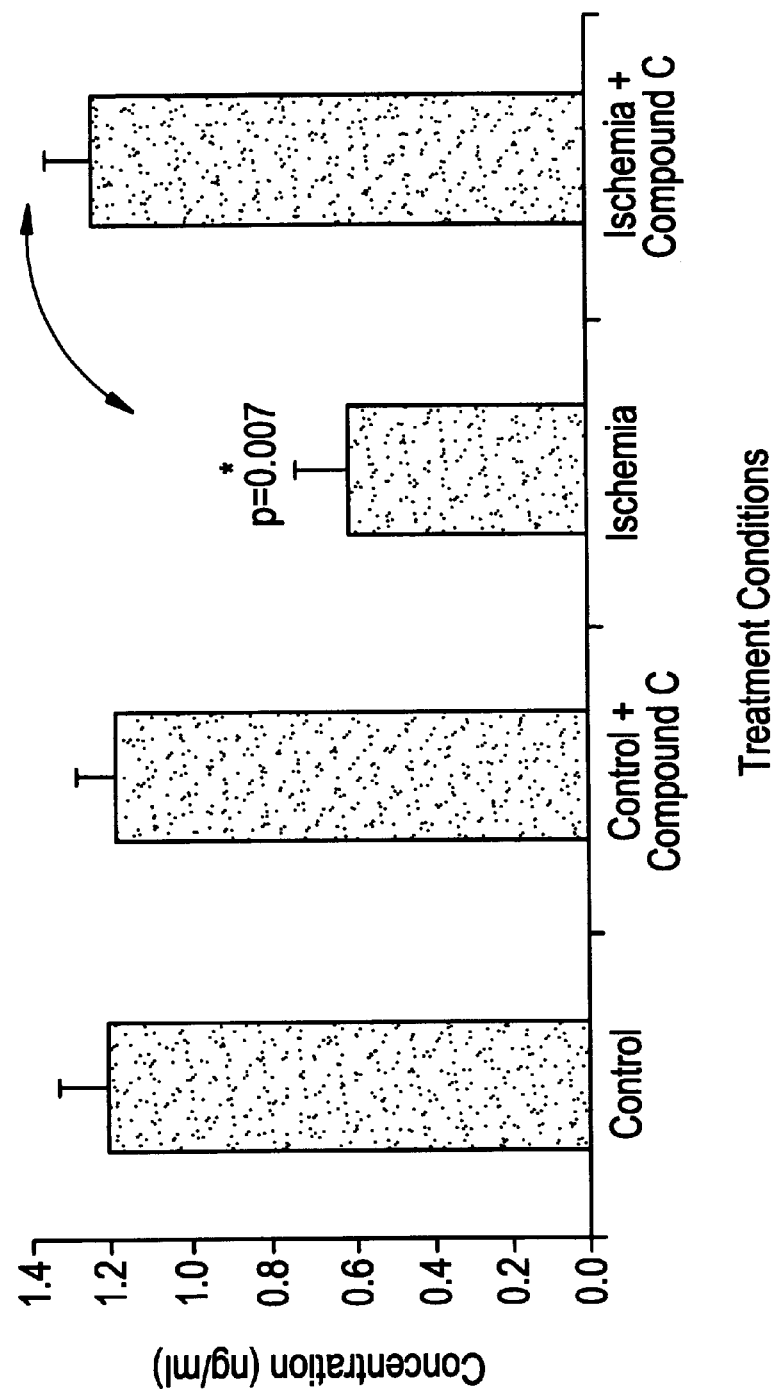
FIG. 2 is a bar graph showing the effect of Compound C on TGF-β2 concentrations in ischemic cell cultures.

Compound C was added to ischemia cell cultures to determine its effect on TGF-β levels during stroke. The experimental data, set forth in FIGS. 1 and 2, show increased concentrations of TGF-β1 and TGF-β2 (FIG. 2) in ischemic cell cultures treated with Compound C. The results indicate that NAALADase inhibition promotes the release of endogenous TGF-β's from glial cells, which in turn provides neuroprotection for neighboring neurons.

Figure 3:
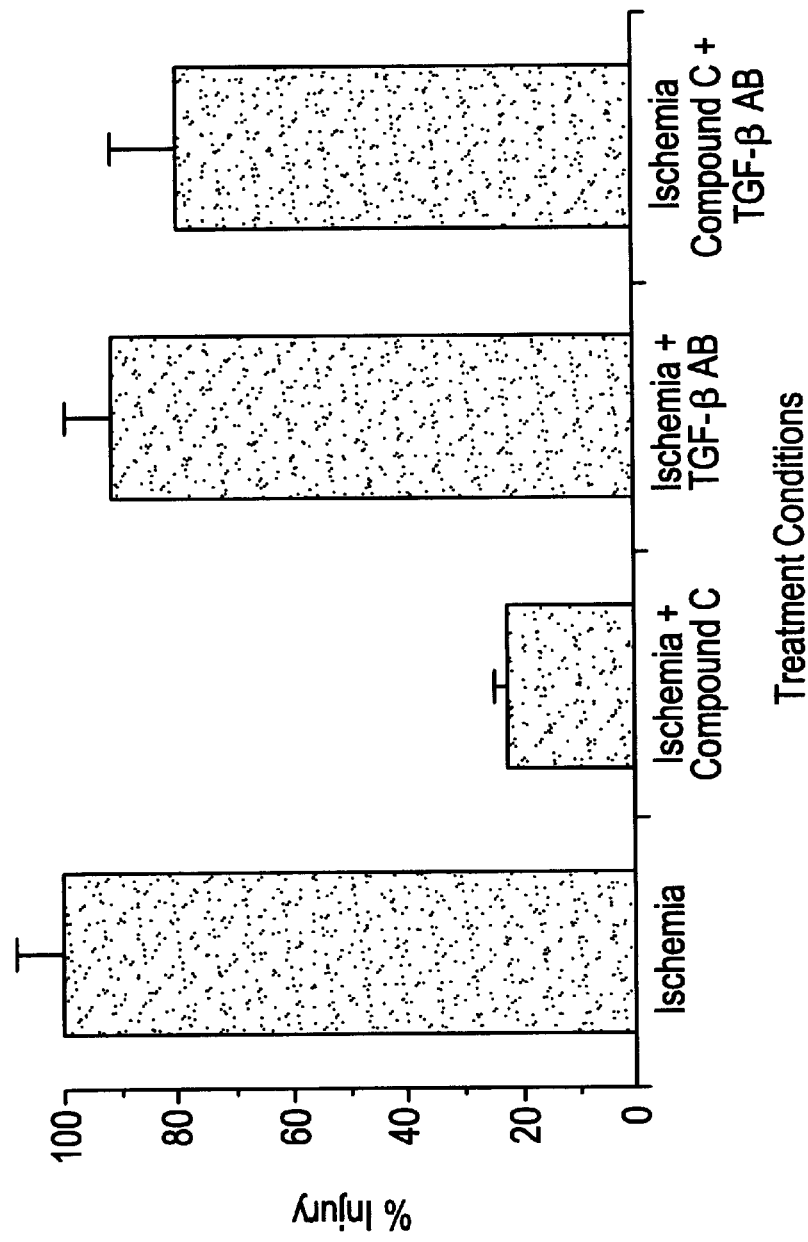
FIG. 3 is a bar graph showing the reversal of the neuroprotective effect of Compound C by TGF-β neutralizing antibodies in ischemic cell cultures.
Figure 4:
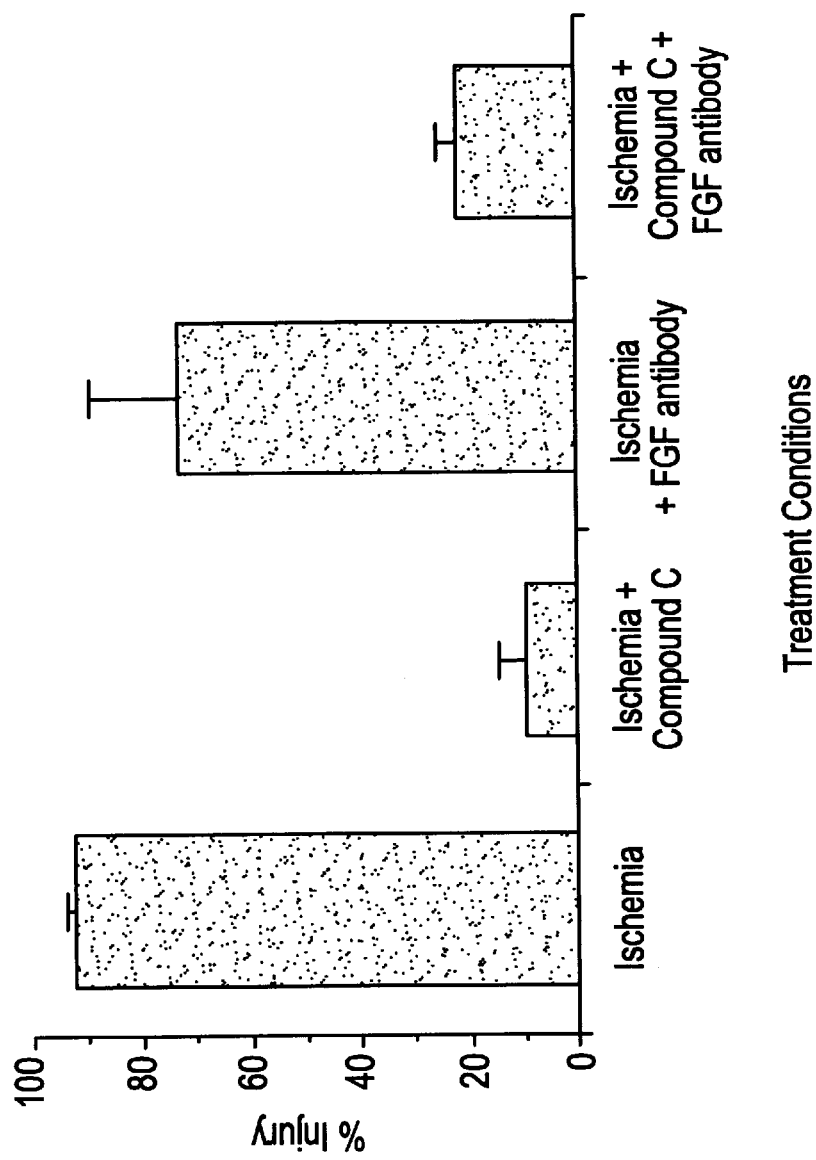
FIG. 4 is a bar graph showing the non-reversal of the neuroprotective effect of Compound C by FGF neutralizing antibodies in ischemic cell cultures

TGF-β neutralizing antibodies were then added to the ischemic cell cultures. FIG. 3 shows that the TGF-β neutralizing antibodies blocked the neuroprotective effect of Compound C in the in vitro ischemia model. By contrast, FIG. 4 shows that the addition of another growth factor antibody, FGF antibody, did not block the neuroprotective effect of Compound C. The results indicate that NAALADase inhibition specifically affects TGF-β levels during stroke.

Example 7

Effect of NAALADase Inhibition on TGF-β in In Vivo Ischemia Model

The effect of TGF-β neutralizing antibodies on the neuroprotective effect of Compound C was also studied in rats following MCAO. FIG. 6 shows that treatment of MCAO rats with Compound C caused a significant rise in TGF-β1 levels during both occlusion and reperfusion, as assessed by microdialysis. The results indicate that NAALADase inhibition provides neuroprotection, at least in part, by regulating endogenous TGF-β's.

Figure 5:
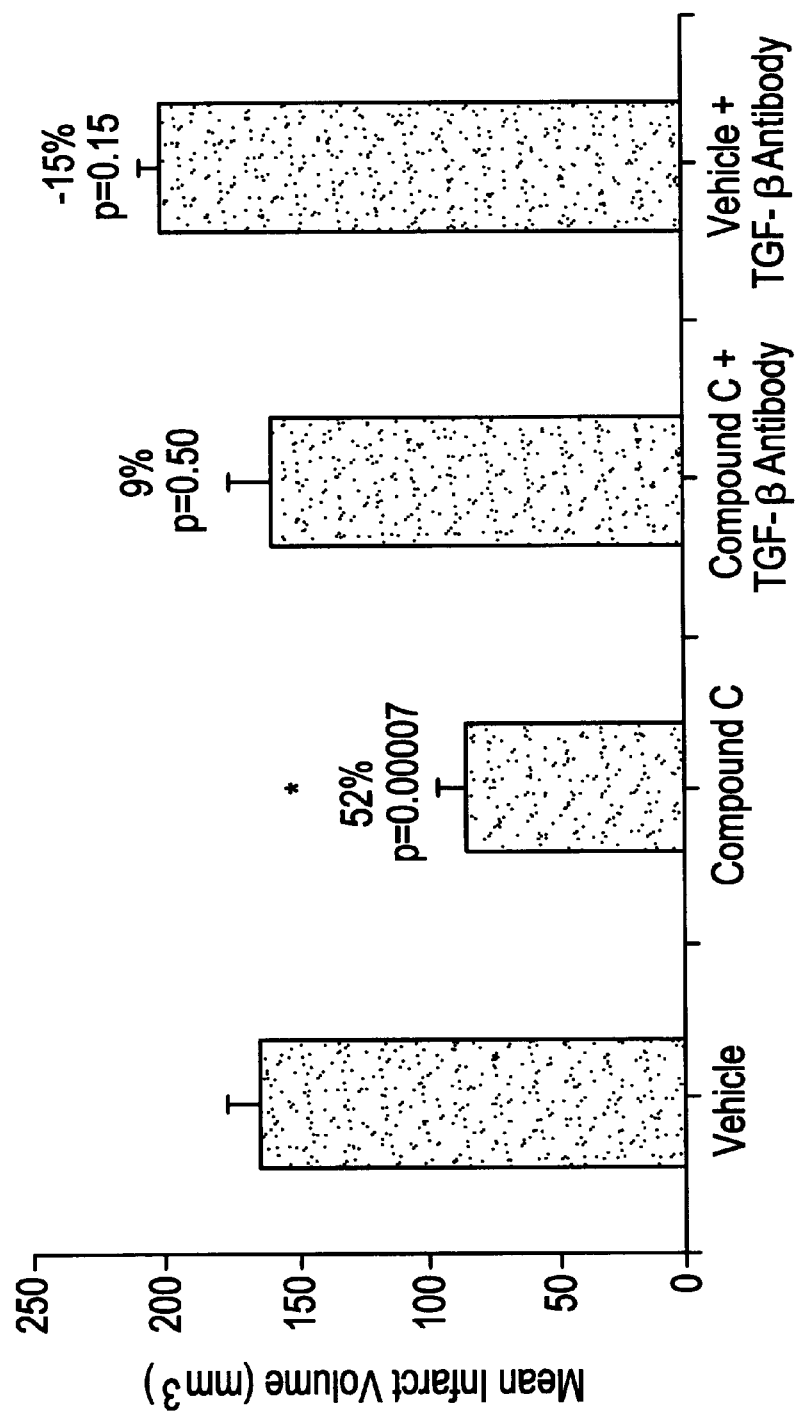
FIG. 5 is a bar graph showing the reversal of the neuroprotective effect of Compound C by TGF-β neutralizing antibodies in rats subjected to middle cerebral artery occlusion ("MCAO").

Additionally, FIG. 5 shows that TGF-β neutralizing antibodies significantly attenuated the neuroprotective effect of Compound C in vivo. One of ordinary skill in the art can appreciate that the regulation of TGF-β's by NAALADase inhibitors may have implications not only in stroke, but also in other diseases, disorders and conditions including, without limitation, neurological diseases, psychiatric diseases, demyelinating diseases, prostate cancer, inflammation, diabetes and angiogenesis.

Example 8

In Vivo Assay of NAALADase Inhibitors on Neuropathic Pain in STZ Model

Figure 7A:
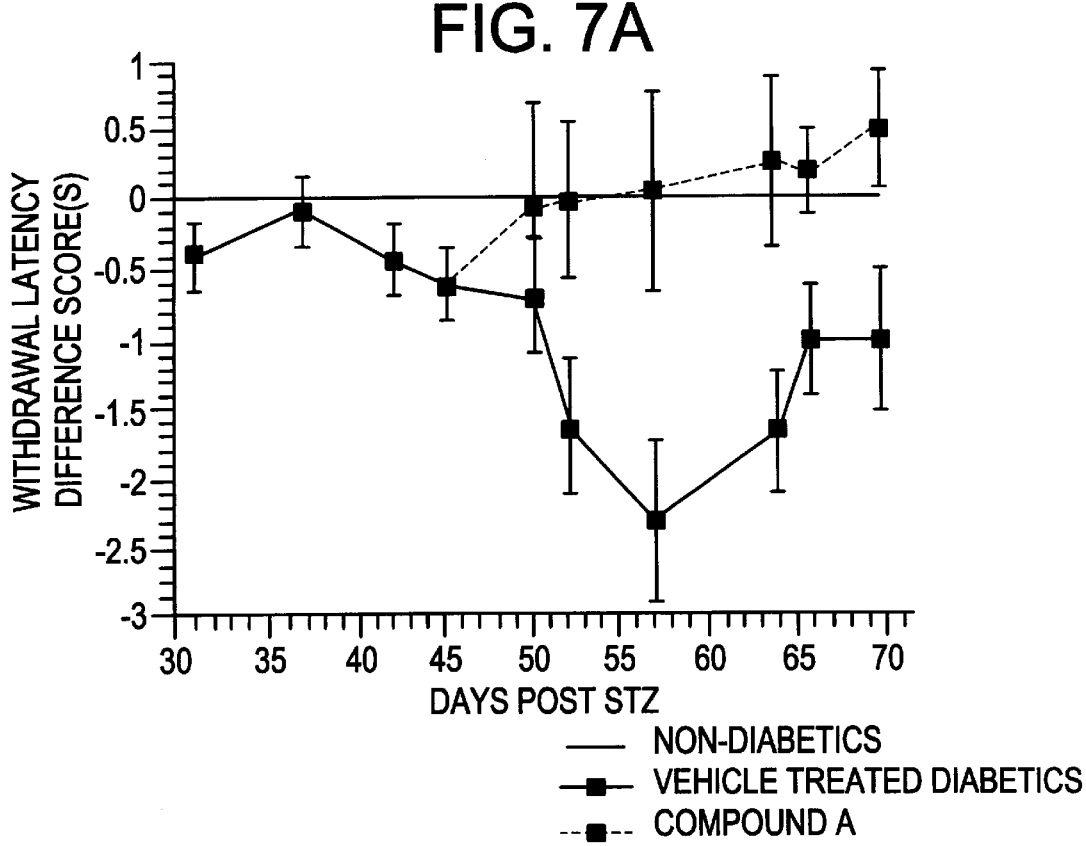
FIG. 7A is a bar graph plotting the withdrawal latency difference scores of non-diabetic rats and STZ-diabetic rats treated with a vehicle or Compound A, against the days following administration with STZ.
Figure 7B:
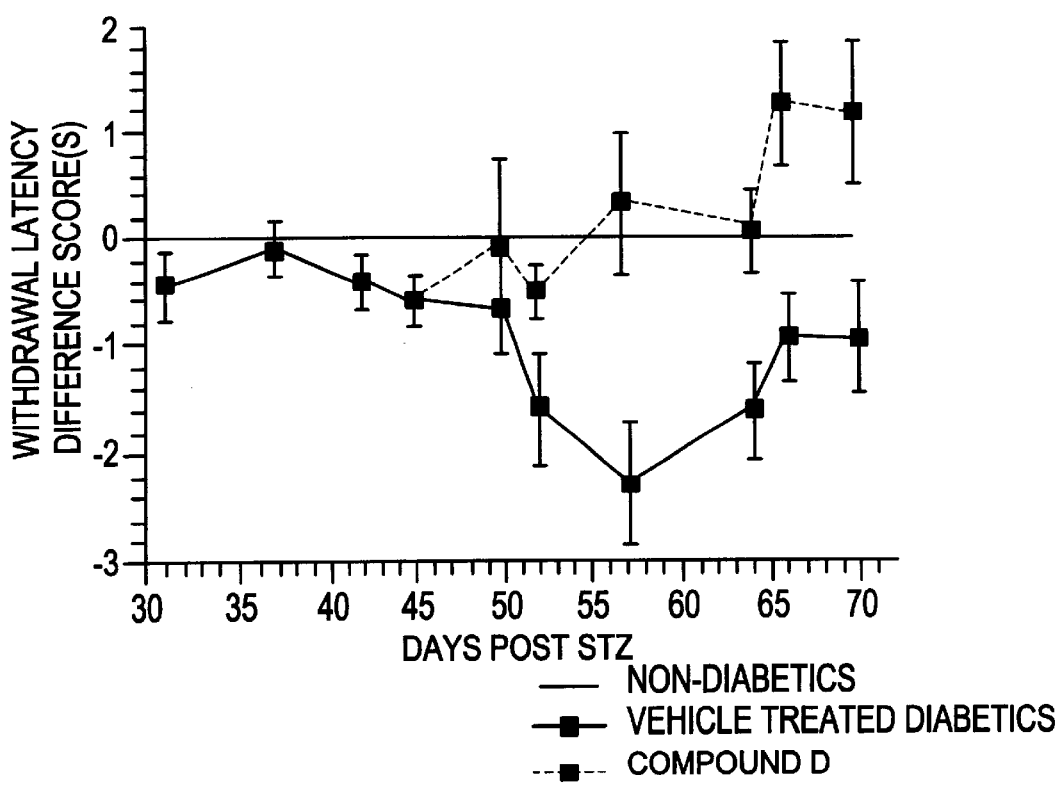
FIG. 7B is a bar graph plotting the withdrawal latency difference scores of non-diabetic rats and STZ-diabetic rats treated with a vehicle or Compound D, against the days following administration with STZ.

Male Sprague-Dawley rats (200–225 g) were rendered diabetic by intravenous administration of streptozotocin ("STZ", 70 mg/kg in phosphate buffered saline). Diabetic animals were divided into five groups: one group receiving Compound A (10 mg/kg or 1 mg/kg), Compound D (10 mg/kg or 1 mg/kg) or vehicle. Another group of animals (non-STZ treated) served as non-diabetic controls. Drug/vehicle treatment was started in diabetic animals 45 days post-STZ administration. STZ-induced diabetic rats were tested for sensitivity to a heat source as soon as blood glucose levels rose to 320 mg/dl or above (30 days post STZ). The rats were then acclimated to a Hargreaves apparatus and thermal nociception was monitored using an infrared heat source directed into the dorsal surface of the hindpaw, and the time taken for the animal to remove its paw noted to the nearest 0.1 seconds (see Hargreaves et al., *J. Biol. Chem.* (1988) 263(36):19392-7 for a description of the experimental method). The intensity of the beam source was adjusted such that the mean latency for control animals (non-STZ treated) was approximately 10 seconds. Each animal was tested 8 times and the mean difference score (between mean non-diabetic control latency and mean diabetic latency) are graphically presented in FIGS. 7A and 7B. Diabetic rats displayed a hyperalgesia (shorter response latency) compared to non-diabetic controls, starting 30 days post STZ treatment and progressively worsening in vehicle treated rats. This hyperalgesic response was completely reversed in diabetic rats receiving treatment with Compound D or A (10 mg/kg i.p. daily). Thus, the results show that NAALADase inhibition attenuates neuropathic pain.

Example 9

In Vivo Assay of NAALADase Inhibitors on Neuropathic Pain in CCI Model

Sciatic nerve ligation, consisting of 4 ligatures tied loosely around the sciatic nerve at 1 mm intervals proximal to the nerve trifurcation, was performed on rats. Following sciatic nerve ligation, the rats exhibited a thermal hyperalgesia and allodynia. The rats were habituated to a Hargreaves apparatus. An infrared heat source was directed onto the dorsal surface of each rat's hindpaws and the time taken for the rat to withdraw its paws was noted. The difference in scores between the latency of the response for the paw on the operated side versus the paw on the unoperated control side was determined.

Compound C

Figure 8:
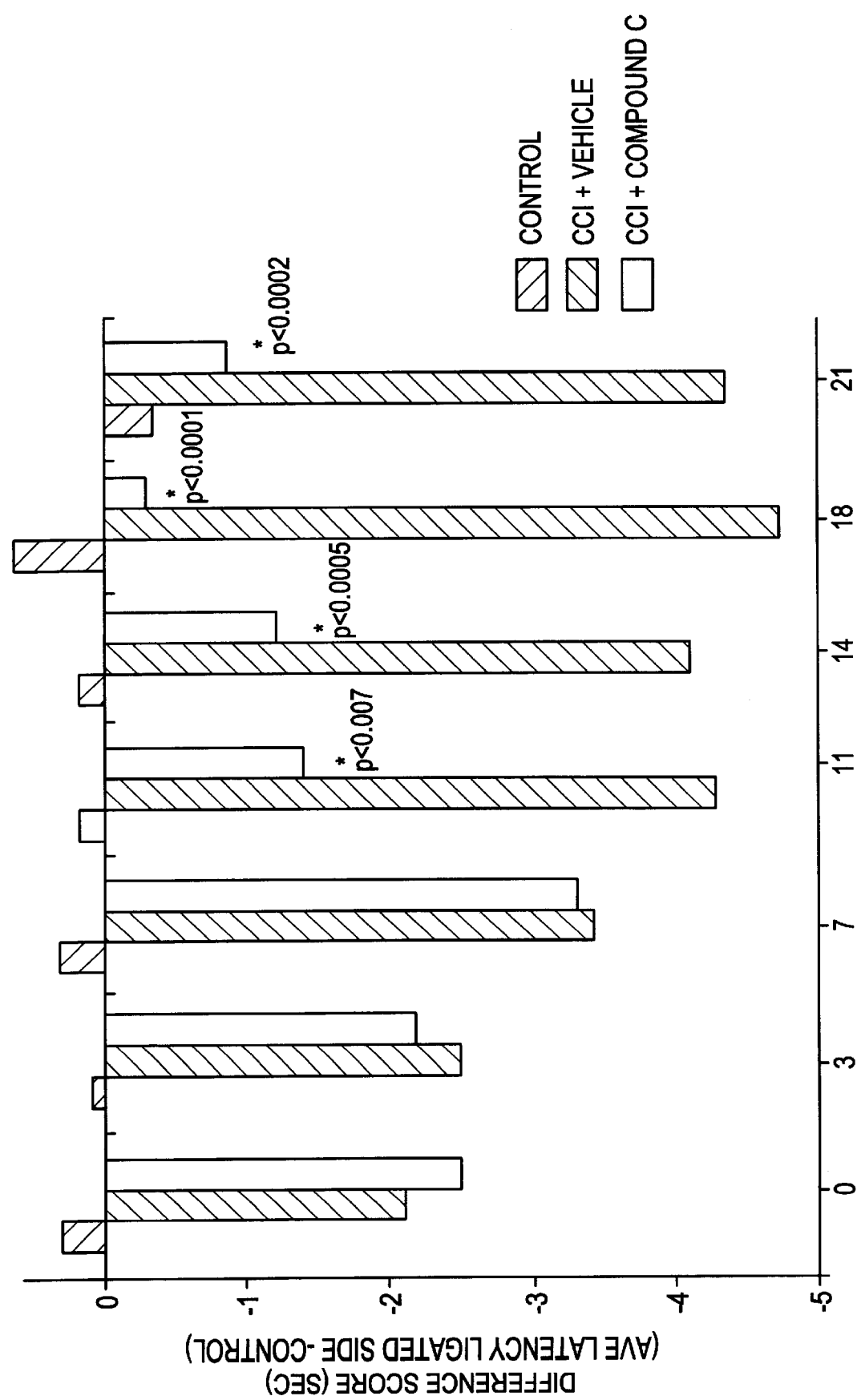
FIG. 8 is a bar graph plotting the withdrawal latency difference scores of normal (unoperated) rats and chronic constrictive injury-induced rats treated with a vehicle or Compound C, against the days following surgery.

The rats received either Compound C (50 mg/kg i.p. daily) or a vehicle starting 10 days post surgery. Treatment with Compound C dramatically normalized the difference scores between the two paws compared to the continued hyperalgesic vehicle treated controls. Normal (unoperated) rats had approximately equal latencies for both paws. This effect was significant starting at 11 days of drug treatment and persisted through to the end of the study (for 21 days of daily dosing). The difference scores are graphically presented in FIG. 8. The results show that NAALADase inhibition attenuates CCI-associated hyperalgesia.

Compound 9

Figure 13:
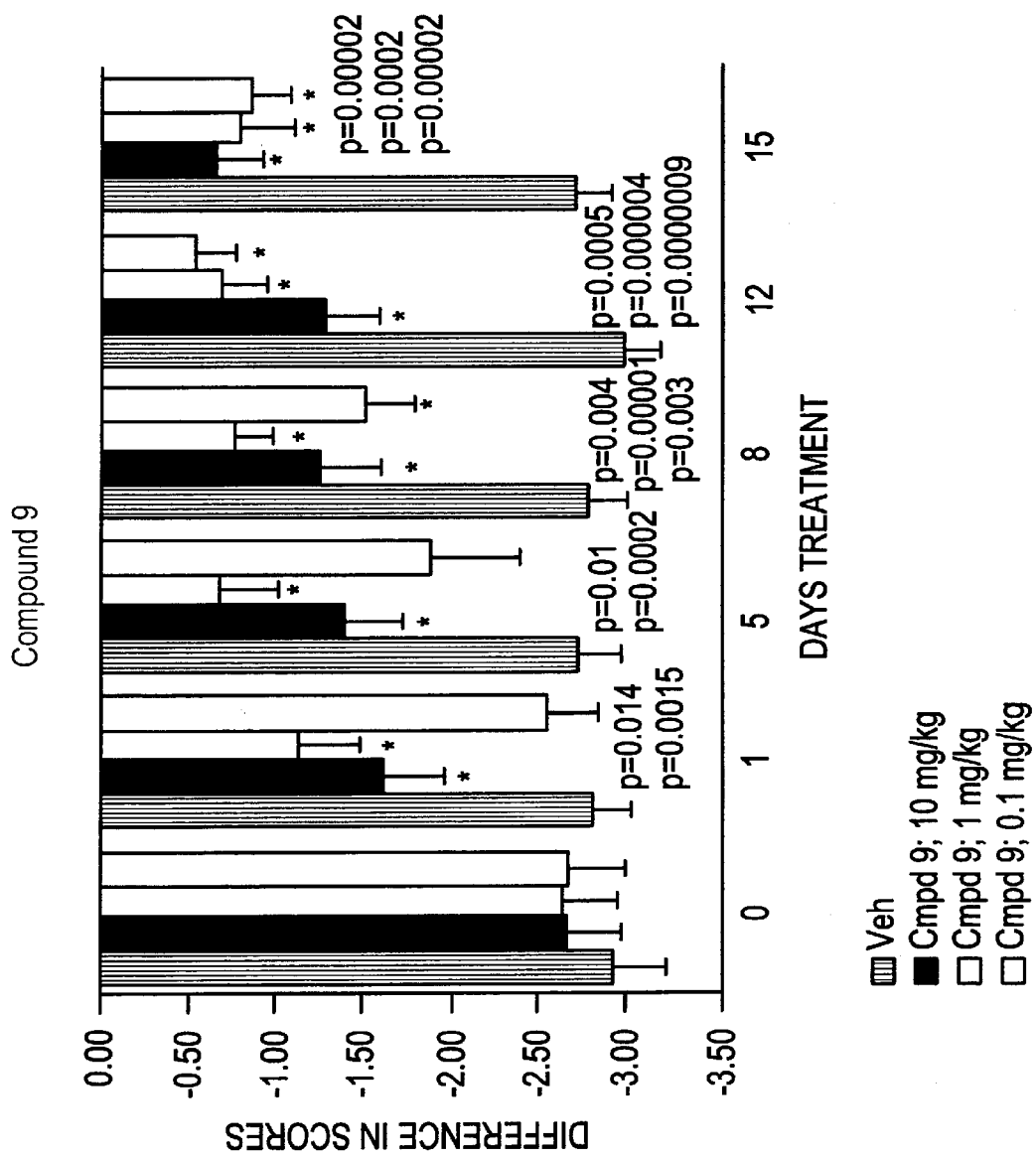
FIG. 13 is a bar graph plotting the withdrawal latency difference scores of chronic constrictive injury-induced rats treated with a vehicle or varying amounts of Compound 9 against the days of treatment.

The rats were treated with either Compound 9 (10, 1 or 0.1 mg/kg) or a vehicle for 15 days after sciatic nerve ligation. Thermal pain responses were measured at days 0, 1, 5, 8, 12 and 15. The differences in scores for the rats treated with a vehicle and the rats treated with Compound 9 are graphically presented in FIG. 13. The results show that treatment with Compound 9 normalized the difference in scores between the operated and unoperated paws compared to the continued hyperalgesic vehicle-treated rats.

Compound 10

Figure 14:
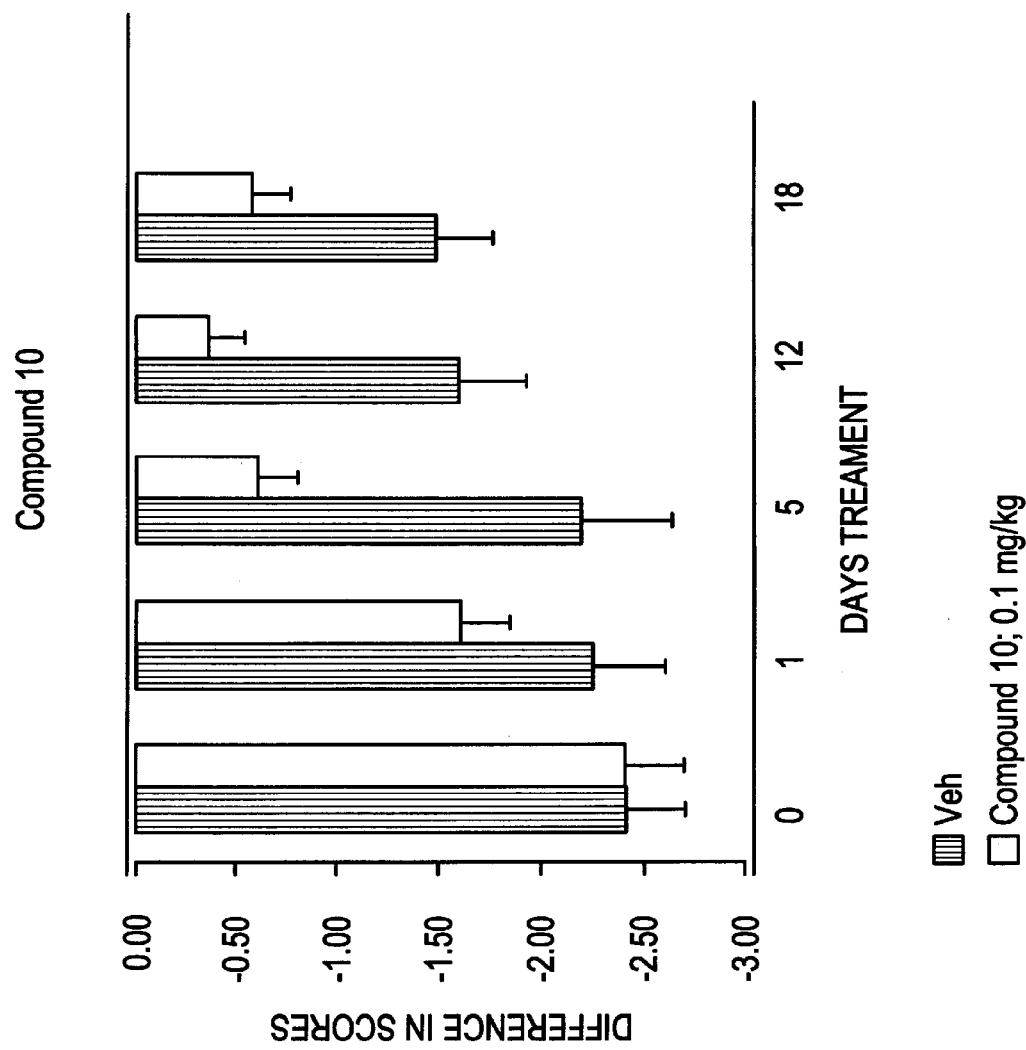
FIG. 14 is a bar graph plotting the withdrawal latency difference scores of chronic constrictive injury-induced rats treated with a vehicle or Compound 10, against the days of treatment.
Figure 15:
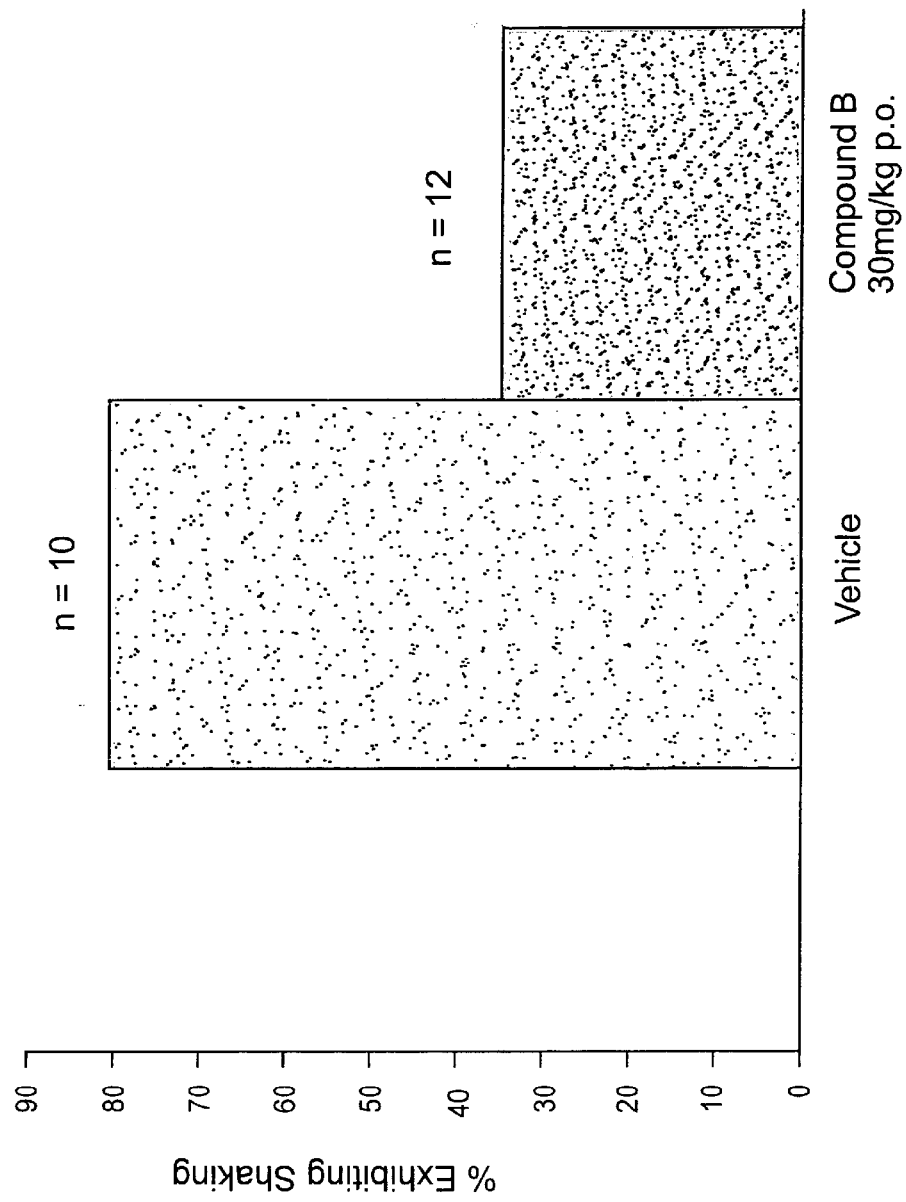
FIG. 15 is a bar graph plotting the percent of transgenic mice at 210 days of age that exhibited limb shaking after treatment with Compound B or a vehicle.
Figure 16:
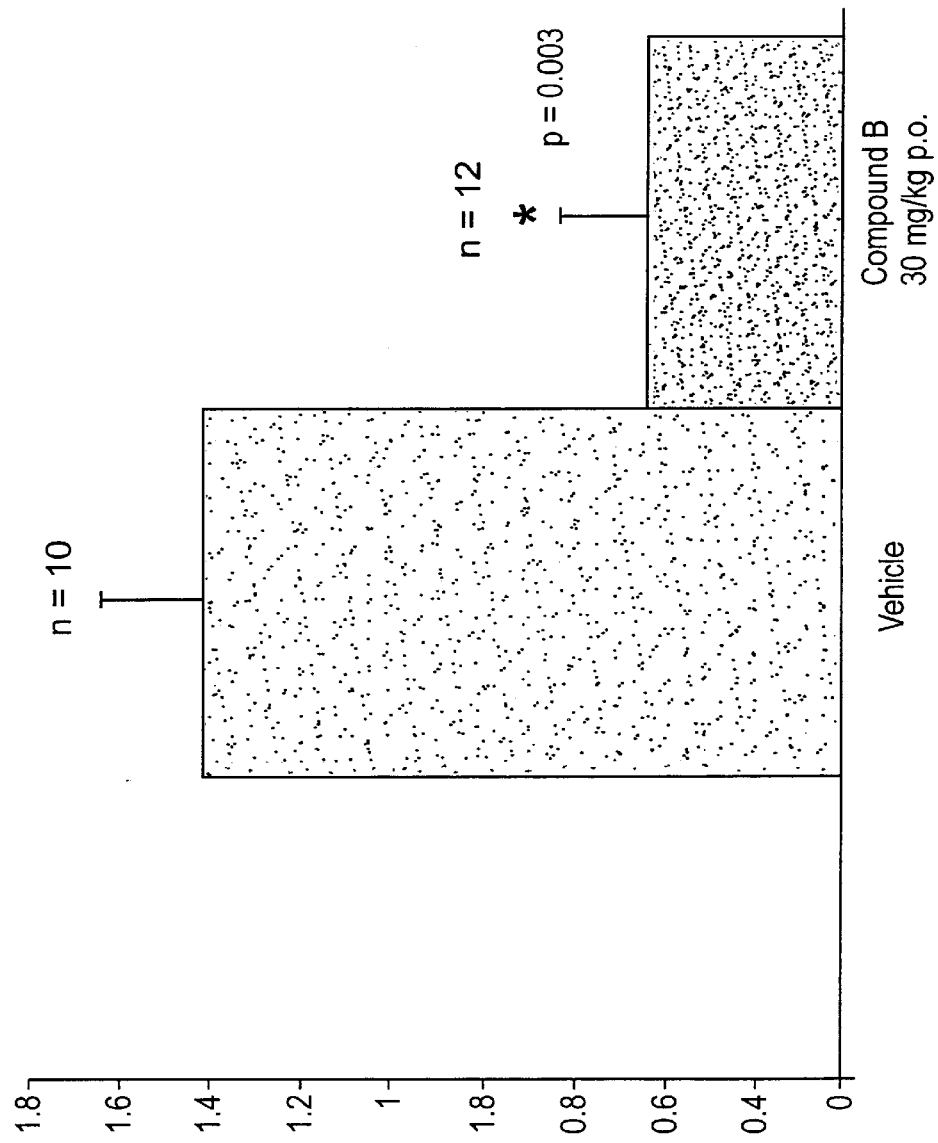
FIG. 16 is a bar graph plotting the gait, measured on an arbitrary scale ranging from 0 to 3, of transgenic mice at 210 days of age after treatment with Compound B or a vehicle.
Figure 17:
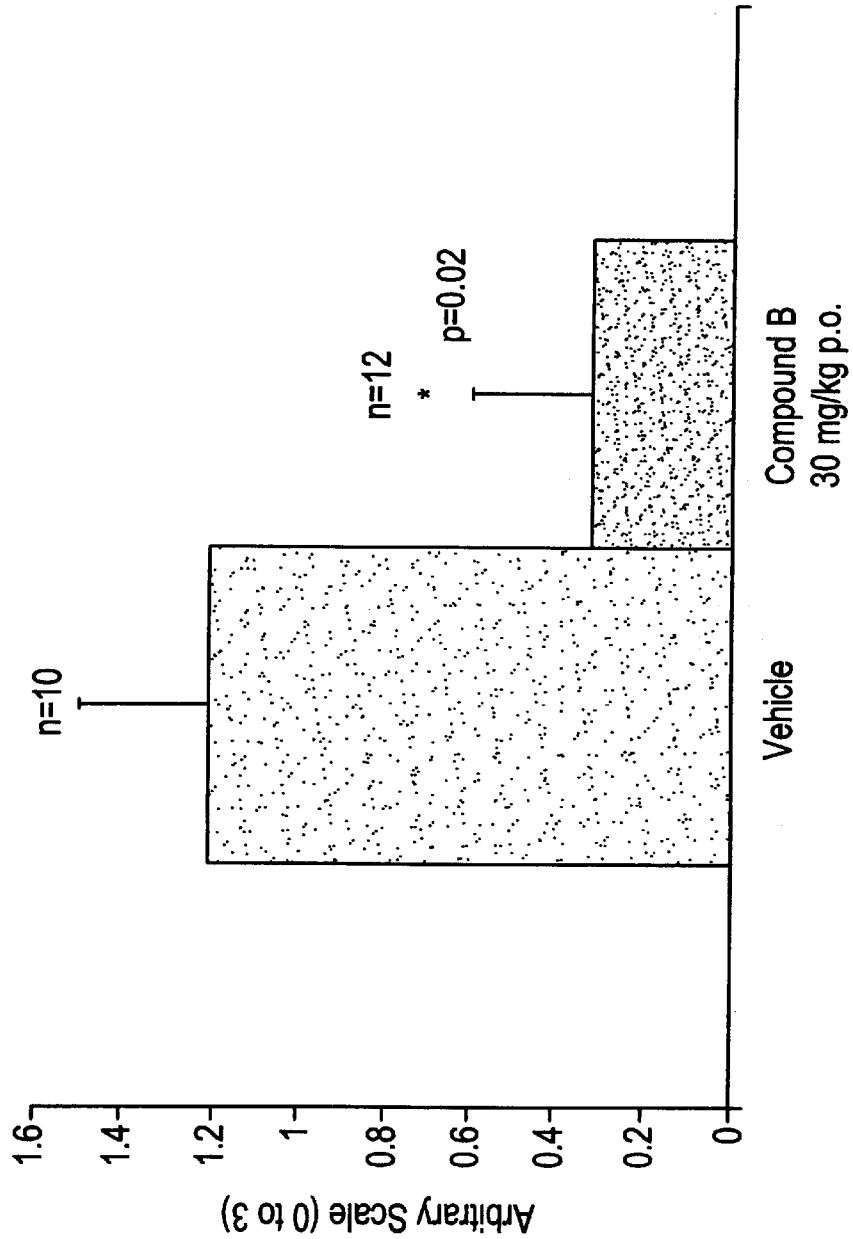
FIG. 17 is a bar graph plotting hind limbs dragging, measured on an arbitrary scale ranging from 0 to 3, of transgenic mice at 210 days of age after treatment with Compound B or a vehicle.
Figure 18:
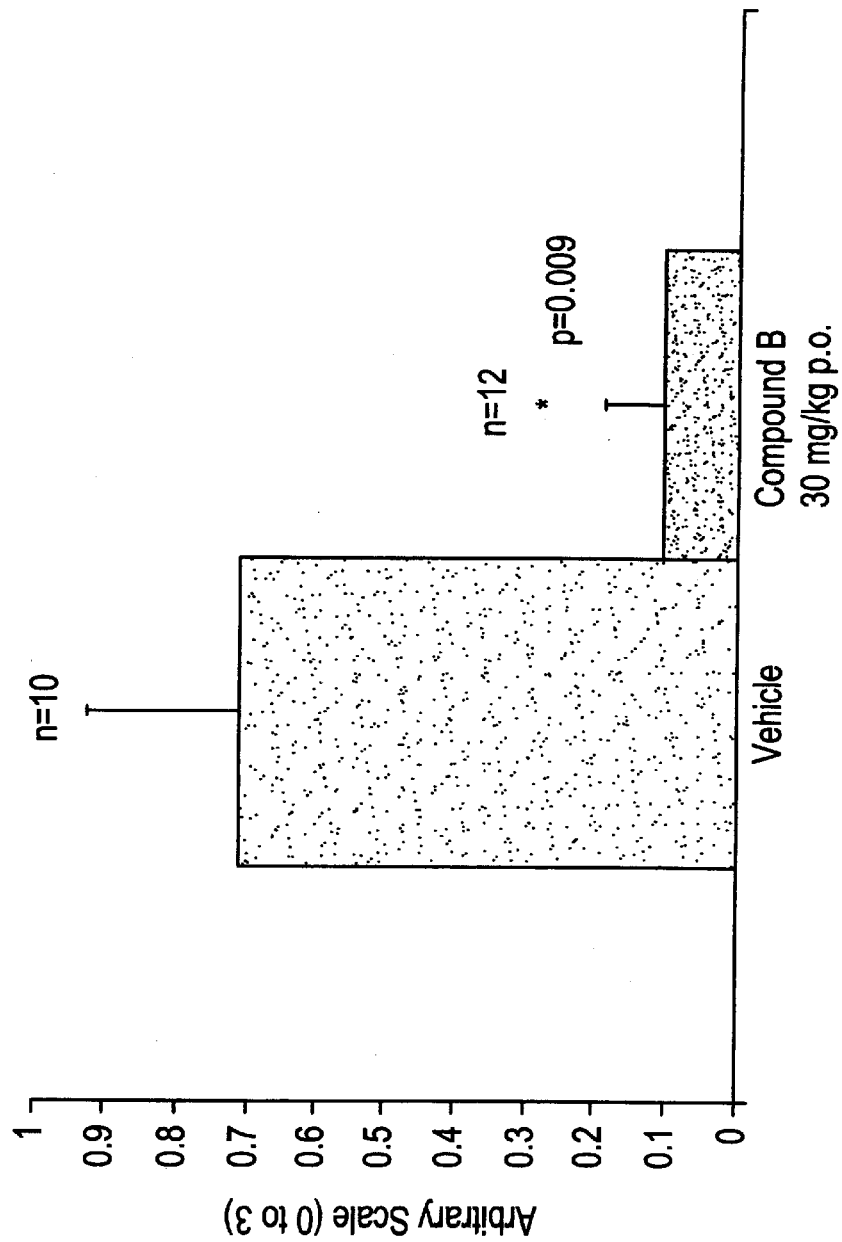
FIG. 18 is a bar graph plotting the crossing of limbs, measured on an arbitrary scale ranging from 0 to 3, of transgenic mice at 210 days of age after treatment with Compound B or a vehicle.
Figure 19:
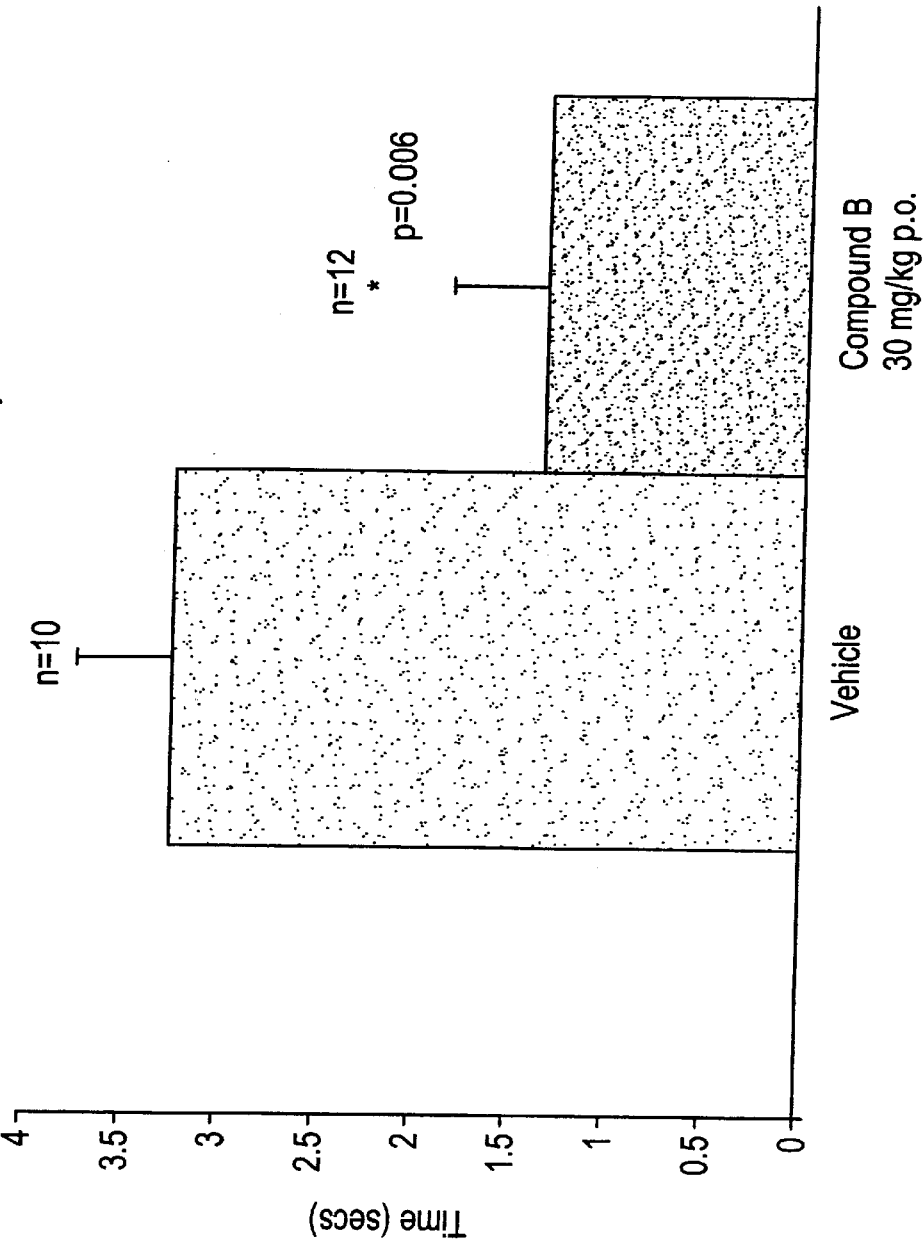
FIG. 19 is a bar graph plotting the righting reflex of transgenic mice, measured by the time (seconds) it took the mice to right themselves when placed on their sides, at 210 days of age after treatment with Compound B or a vehicle.
Figure 20:
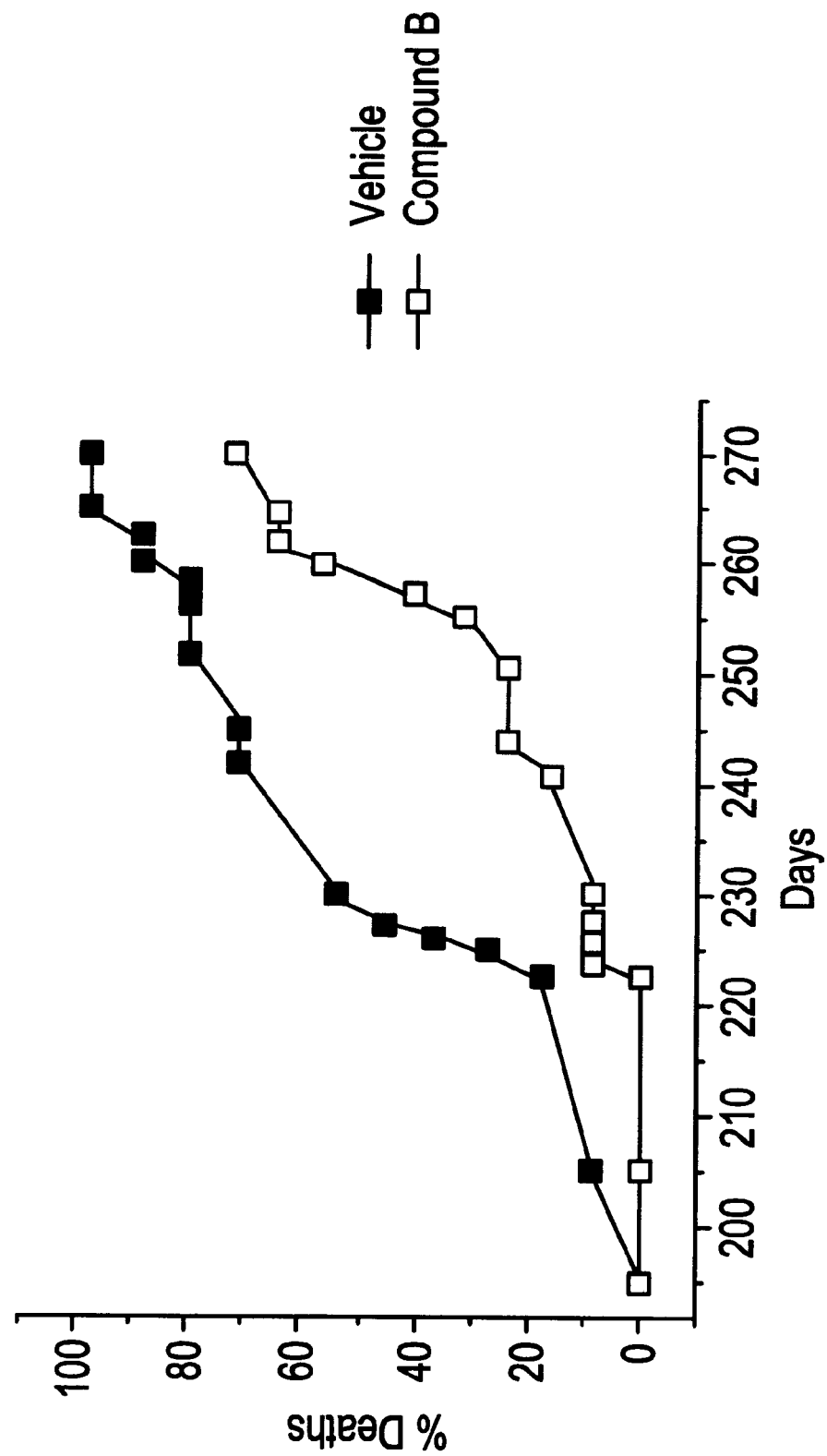
FIG. 20 is a graph plotting the percent of transgenic mice treated with Compound B or a vehicle that died against the age of the mice (days).
Figure 21:
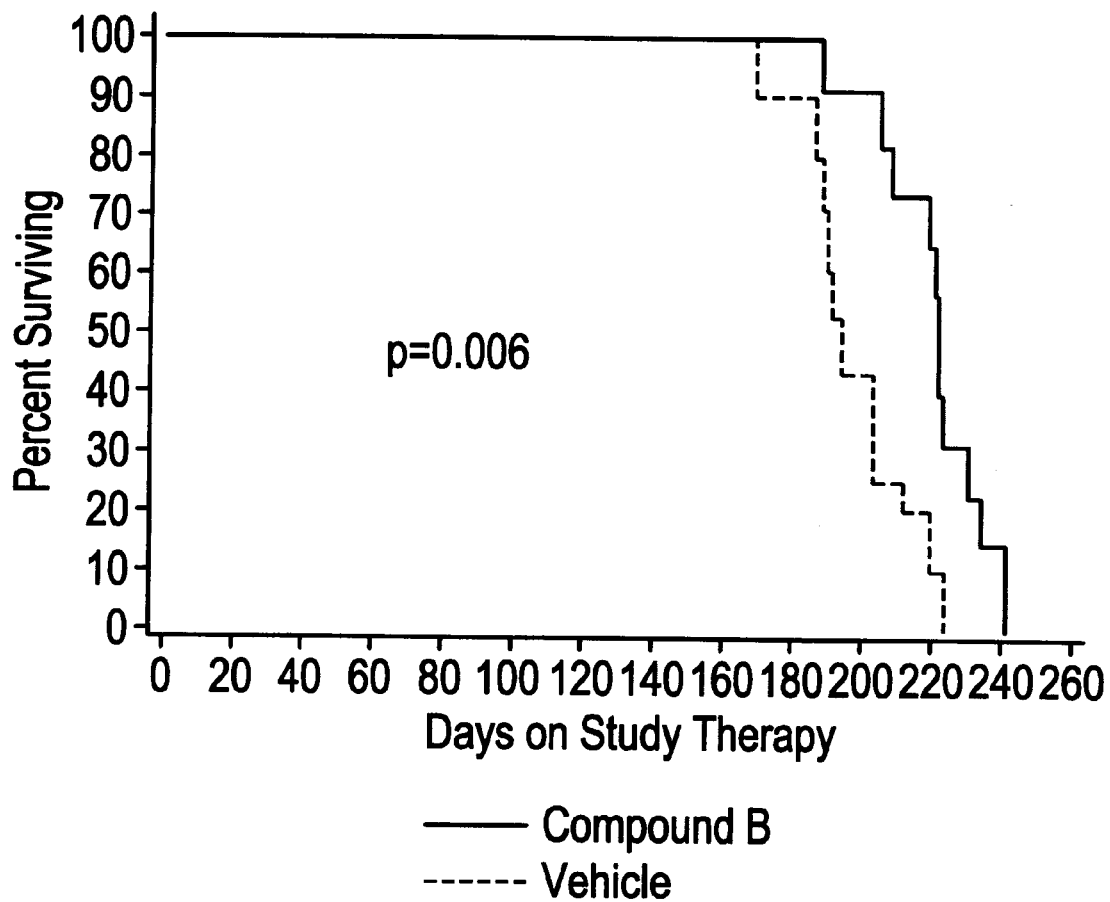
FIG. 21 is a Kaplan-Meier survival graph plotting the percent of transgenic mice treated with Compound B or a vehicle that survived against the number of days that the mice were on study therapy.

The rats were treated with either Compound 10 (0.1 mg/kg) or a vehicle for 18 days after sciatic nerve ligation. Thermal pain responses were measured at days 0, 1, 5, 12, and 18. The differences in scores for the rats treated with a vehicle and the rats treated with Compound 10 are graphically presented in FIG. 14. The results show that treatment with Compound 10 normalized the difference in scores between the operated and unoperated paws compared to the continued hyperalgesic vehicle-treated rats.

Example 10

In Vivo Assay of NAALADase Inhibitors on Progression of Neuropathic Pain in BB/W Models Male BB/W rats (BRI, Mass) spontaneously develop a cell mediated autoimmune destruction of pancreatic B cells, resulting in onset of insulin-dependent (Type I) diabetes (Awata, Guberski, *Endocrinology* (1995) 136(12):5731-5). These rats have been characterized and shown to demonstrate neuropathies with accompanying neural deficits such as fiber loss and degeneration, changes which are correlative with those seen in peripheral nerve of human diabetic patients (Yagihasi, *J. Peripher. Nerv. Syst.* (1997) 2(2):113-32). This renders them valuable for experimental trials of new compounds for future treatments of this major disorder. In the present study, Compound A and Compound D were examined for their ability to alter the progression of diabetic neuropathy. The rats received daily injection of Compound A or Compound D (10 mg/kg i.p.) or vehicle, starting at the onset of diabetes (hyperglycemia) and up to 6 months thereafter. Another group of non-diabetic rats also receiving vehicle were tested. All animals were continuously monitored for body weight, urine volume, blood sugar and glycated haemoglobin. In the first month of the study, all animals were tested for thermal nociception in a Hargreaves apparatus, weekly. After the first month this was done biweekly and then monthly. The testing consists of directing an infrared heat source onto the dorsal surface of the rat hindpaw and noting the time taken for the animal to remove its paw (see Hargreaves et al., *J. Biol. Chem.* (1988) 263 (36):19392-7 for a description of the experimental method). Each animal was tested 8 times and the mean withdrawal latency noted.

Figure 11:
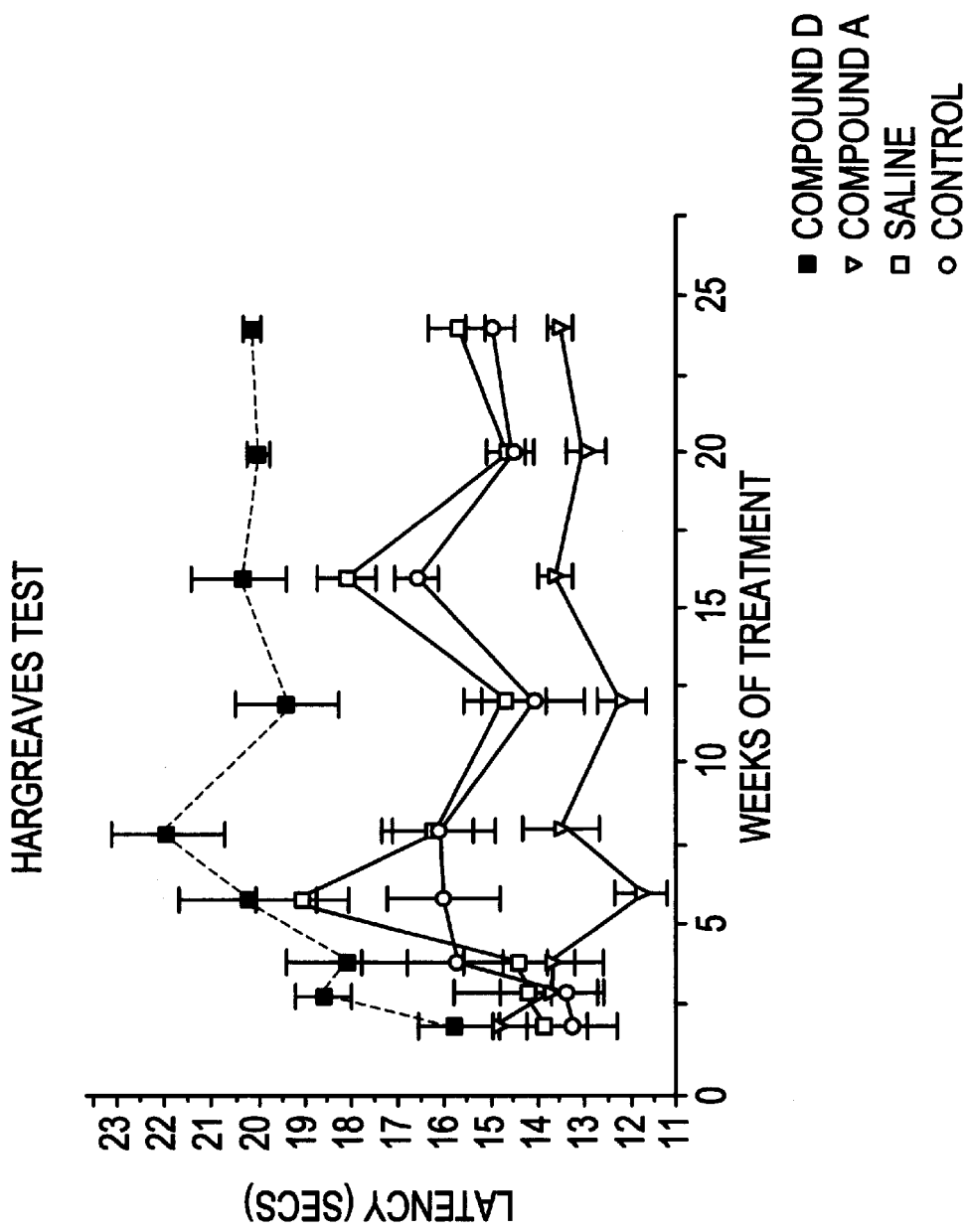
FIG. 11 is a graph plotting the withdrawal latency of non-diabetic rats and BB/W diabetic rats treated with a vehicle, Compound D, or Compound A, against the weeks of treatment.

The results are graphically presented in FIG. 11. The results show that diabetic rats displayed a hyperalgesia (shorter response latency) compared to non-diabetic controls. Diabetic drug-treated rats (both Compound A and Compound D) displayed longer withdrawal latencies than diabetic vehicle-treated rats, starting after 4 weeks of treatment and persisting through the six months of treatment.

Figure 12:
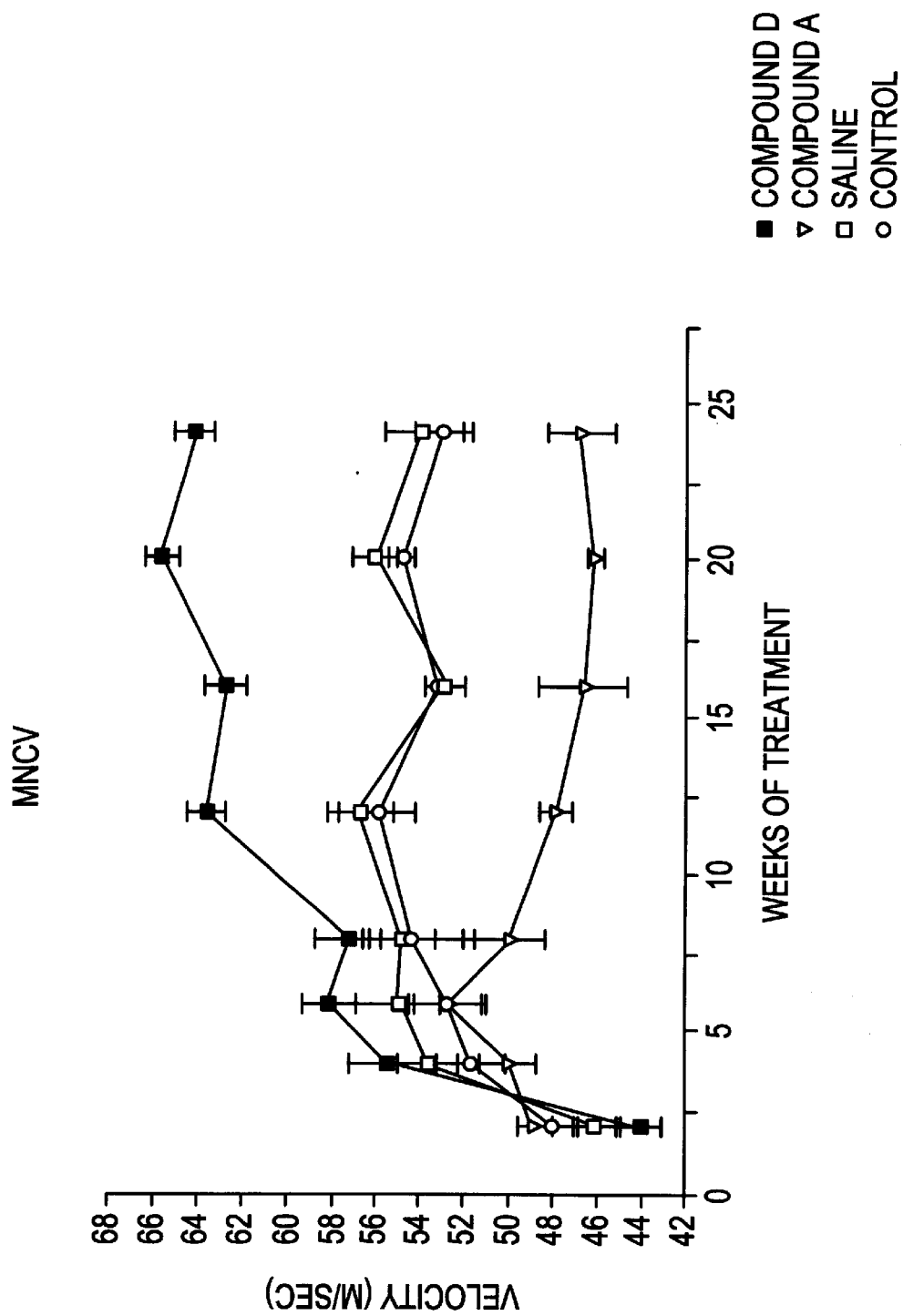
FIG. 12 is a graph plotting the nerve conduction velocity of non-diabetic rats and BB/W diabetic rats treated with a vehicle, Compound D, or Compound A, against the weeks of treatment.

Nerve conduction velocity was also measured every two weeks through the first eight weeks of treatment and every month thereafter through to the six months of treatment (see De Koning et al., *Peptides*, Vol. 8, No. 3, pp. 415–22 (1987) for a description of the experimental method). The results are graphically presented in FIG. 12. Diabetic animals generally showed a reduction in nerve conduction velocity compared to non-diabetic controls. However, diabetic animals receiving daily injections of NAALADase inhibitor (either Compound A or Compound D at a dose of 10 mg/kg) showed significantly less severe nerve conduction deficits than did the diabetic controls receiving vehicle treatment. This was apparent starting at 8 weeks of treatment and persisted to a similar degree through to the six month termination point of the study. Diabetic vehicles, on the other hand, showed a progressive deterioration in nerve conduction velocity from 6 to 16 weeks after start of vehicle administration which was maintained through to six months.

Example 11

In Vivo Assay of NAALADase Inhibitors on Diabetic Neuropathy in STZ Model

Figure 9A:
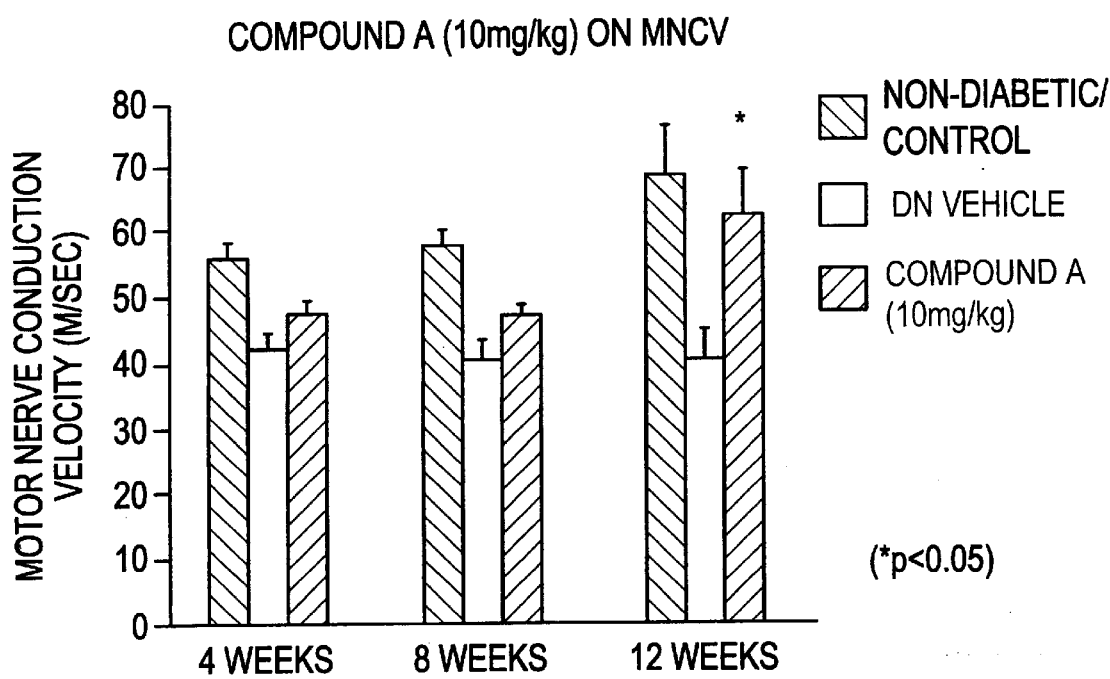
FIG. 9A is a bar graph plotting the motor nerve conduction velocity of non-diabetic rats and STZ-diabetic rats treated with a vehicle or Compound A, against the weeks following administration with STZ.
Figure 9B:
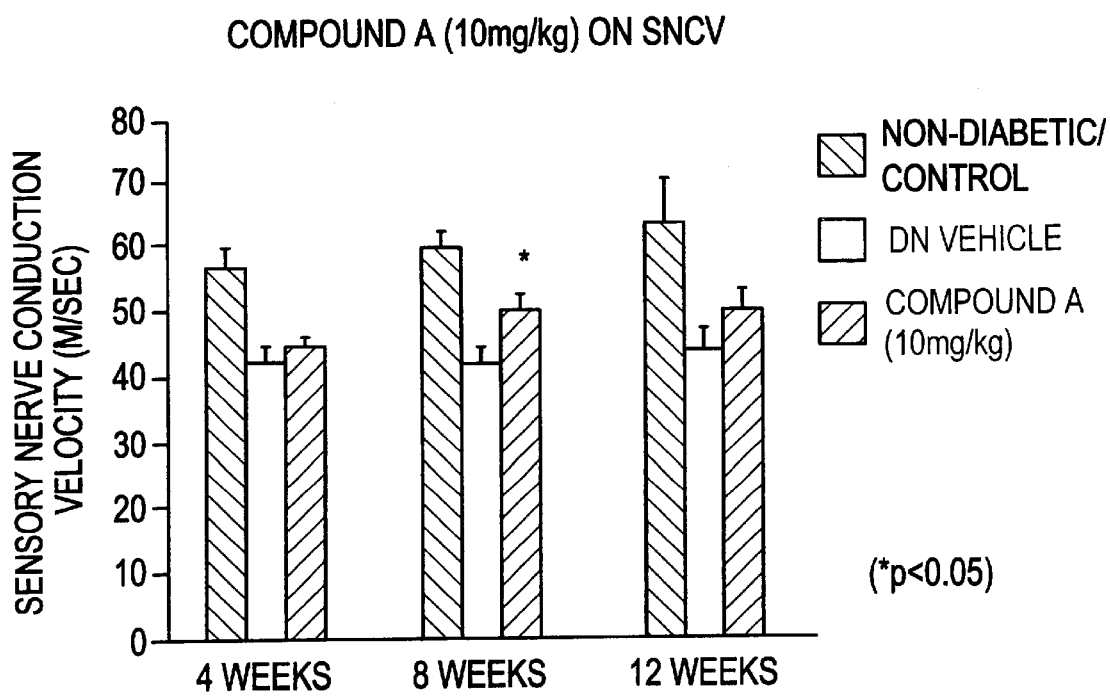
FIG. 9B is a bar graph plotting the sensory nerve conduction velocity of non-diabetic rats and STZ-diabetic rats treated with a vehicle or Compound A, against the weeks following administration with STZ.
Figure 10A:
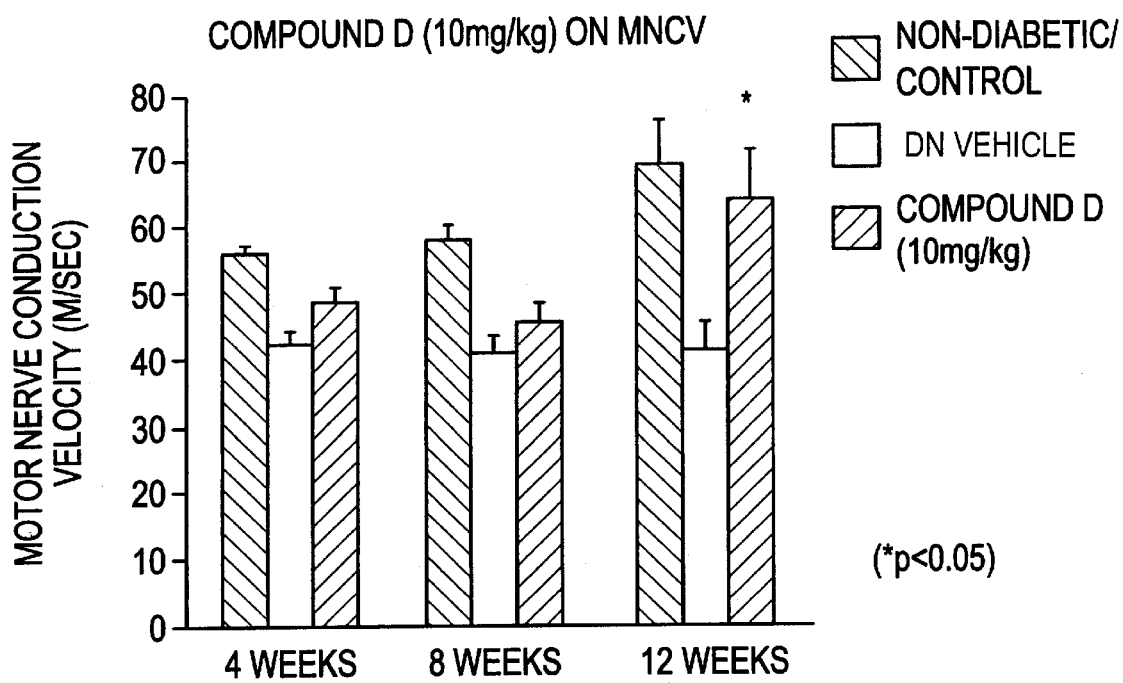
FIG. 10A is a bar graph plotting the motor nerve conduction velocity of non-diabetic rats and STZ-diabetic rats treated with a vehicle or Compound D, against the weeks following administration with STZ.
Figure 10B:
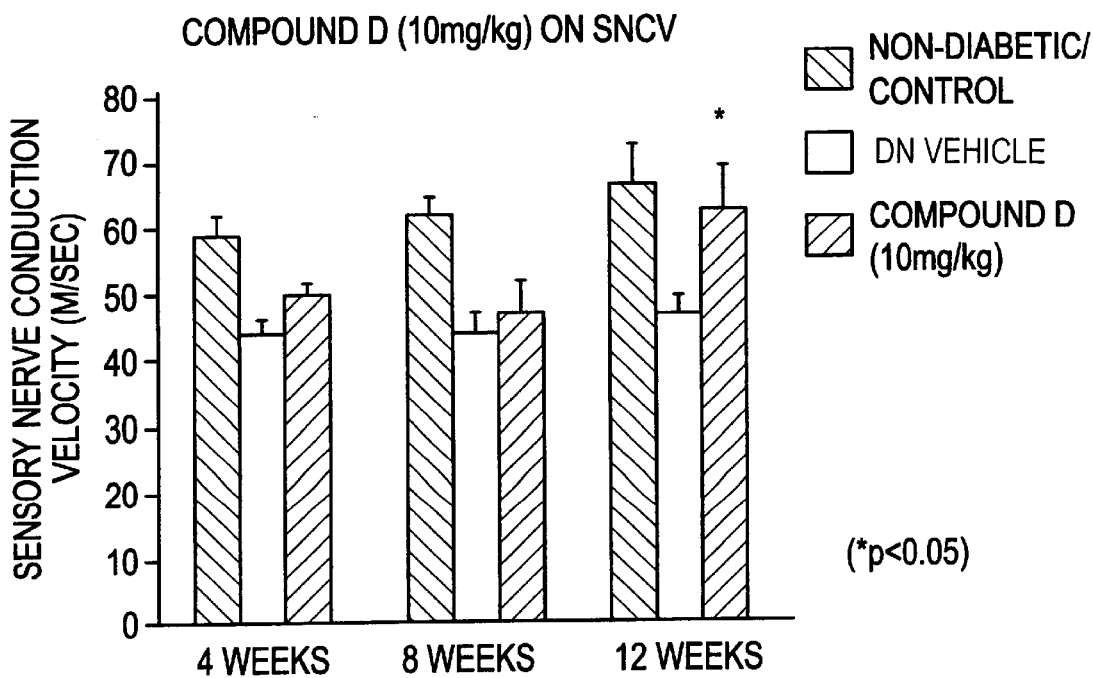
FIG. 10B is a bar graph plotting the sensory nerve conduction velocity of non-diabetic rats and STZ-diabetic rats treated with a vehicle or Compound D, against the weeks following administration with STZ.

Motor and sensory nerve conduction velocity was also measured in STZ-diabetic animals after 4, 8 and 12 weeks of treatment (see De Koning et al., supra, for a description of the experimental method). Briefly, stimulating needle electrodes were inserted close to the sciatic and tibial nerves with recording electrodes being placed subcutaneously over the distal foot muscles, in anesthetized rats. The results are graphically presented in FIGS. 9A, 9B, 10A and 10B. Diabetic animals receiving vehicle showed a significant reduction in both motor and sensory nerve conduction compared to non-diabetic animals. Treatment with 10 mg/kg of Compound A daily for 4, 8 and 12 weeks all tended to improve (increase) both motor and sensory nerve conduction velocities, with a significant improvement being observed after 12 weeks and 8 weeks for motor and sensory nerve conduction velocity, respectively (FIGS. 9A and 9B). The lower dose of Compound A tested (1 mg/kg) had similar effects. Treatment of animals with Compound D at either dose also increased both motor and sensory nerve conduction velocities above that of diabetic controls, significantly so after 12 weeks of treatment for the 10 mg/kg treatment group (FIGS. 10A and 10B) and at the earlier time periods after treatment with the 1 mg/kg dose. Thus, the results show that NAALADase inhibition alters the progression of diabetic neuropathy.

Example 11A

In Vivo Assay of NAALADase Inhibitors— Reversal of Diabetic Neuropathy in STZ Model General Method for STZ Model—Delayed Dosing Rats (200–225 grams) were injected with STZ (70 mg/kg) into the tail vein. Diabetes (>350 mg/dl) was confirmed in all rats, 4 weeks after STZ administration. Rats were left untreated until 35–49 days after STZ. Compound D (1, 3, or 10 mg/kg), Compound E (10 mg/kg), or vehicle were dosed daily p.o. following confirmation of hyperalgesia and/or nerve conduction velocity deficits. In separate experiments, onset of treatment was delayed until 60 to 90 days after SZ administration. Nerve conduction velocity or withdrawal response to thermal stimulation of hind paws was measured at intervals, usually bi-weekly for thermal response and monthly for nerve conduction velocity.

General Method for db/db Mice Study

Spontaneously diabetic mice (db/db mice) and non-diabetic littermates were obtained from Jackson labs. Mice were left untreated until 7–8 months of age (or after 4–5 months of chronic diabetes) and then dosed daily with compound F (1 mg/kg) p.o. Nerve conduction velocity was measured prior to the onset and after eight weeks of treatment.

Nerve Conduction Velocity Measurements

Sensory and motor nerve conduction velocities were evaluated using the method of De Koning and Gispen (*Peptides* 8:415–422, 1987). Electrophysiological evaluation was carried out within one hour of dosing. Animals were anesthetized with isoflurane and stimulating needle electrodes were inserted close to the sciatic nerve at the sciatic notch and the tibial nerve near the ankle. Recording electrodes were placed over the foot muscles. Stimuli were applied and responses recorded. Motor and sensory nerve conduction velocities were calculated by measuring the distance between the sciatic notch and ankle sites, and the latency between the M-wave and the H-reflex.

Thermal Hyperalgesia

Animals were acclimated to the apparatus for at least 5 min. An infra-red source was placed under below the plantar surface of the rat hind-paw. The intensity of the source was adjusted so that latency for normal rats was about 10 secs. Animals were tested for thermal response latency according to the method of Hargreaves et al (Pain 77–88, 1988). Each animal was tested 8 times (4 each hind limb) and the latency of response recorded automatically to nearest 0.1 sec. An average of the last 4 measurements for each paw was calculated (8 total measurements) and noted for each rat.

Figure 22:
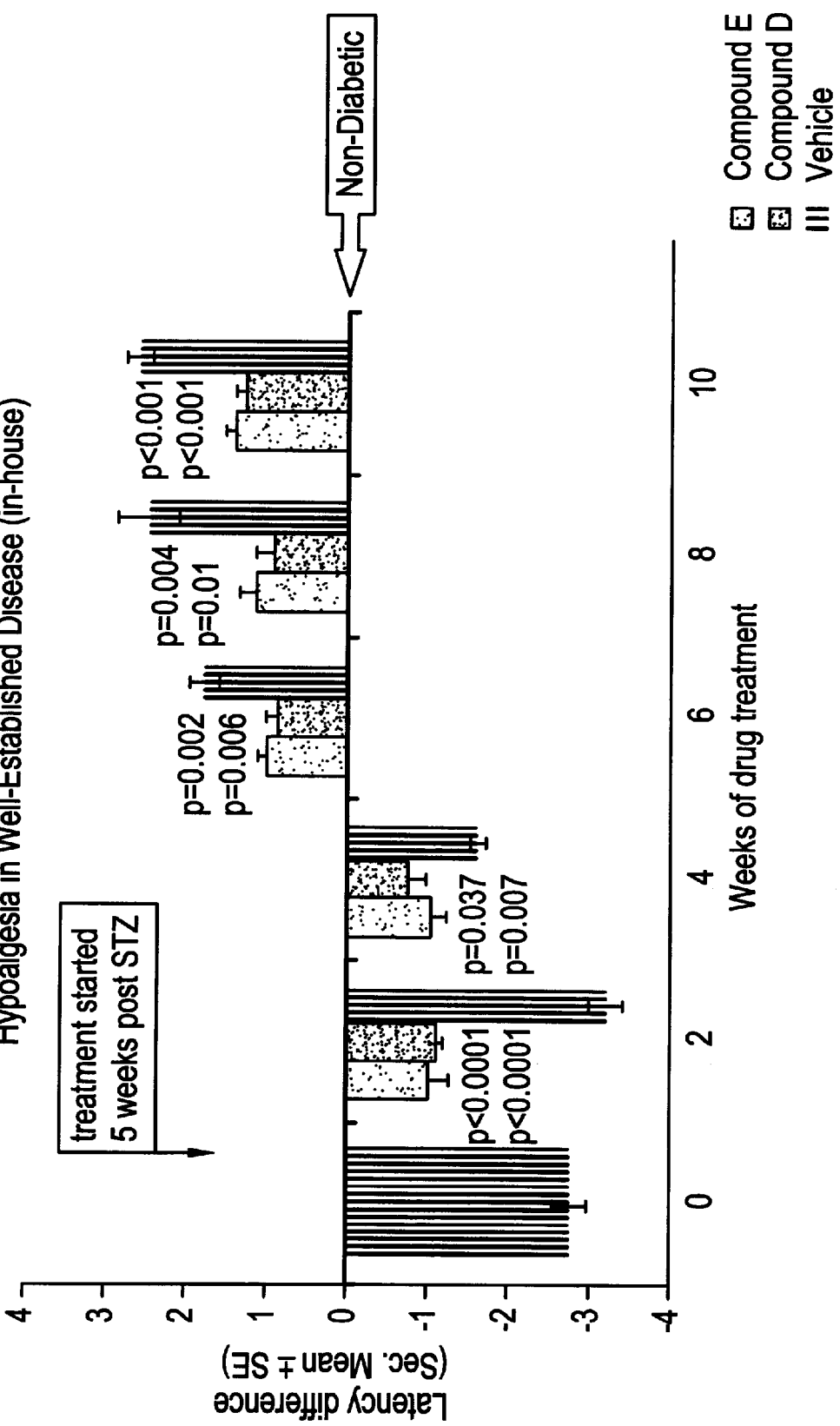
FIG. 22 shows the effect of treatment with Compounds D and E on neuropathic pain abnormalities in STZ diabetic rats.

FIG. 22 shows the effect of NAALADase inhibitor (Compound D and Compound E) treatment on neuropathic pain abnormalities in STZ diabetic rats. All rats showed apparent hyperalgesia compared to non-diabetics prior to NAALADase inhibitor treatment (5 weeks post STZ). However, within two weeks of treatment neuropathic hyperalgesia was reversed towards normal in both NAALADase inhibitor treated groups. This reversal persisted throughout the subsequent hypoalgesic phase usually seen in prolonged diabetic-STZ rats, with a reduced hypoalgesic phase displayed in NAALADase treated rats.

Figure 23:
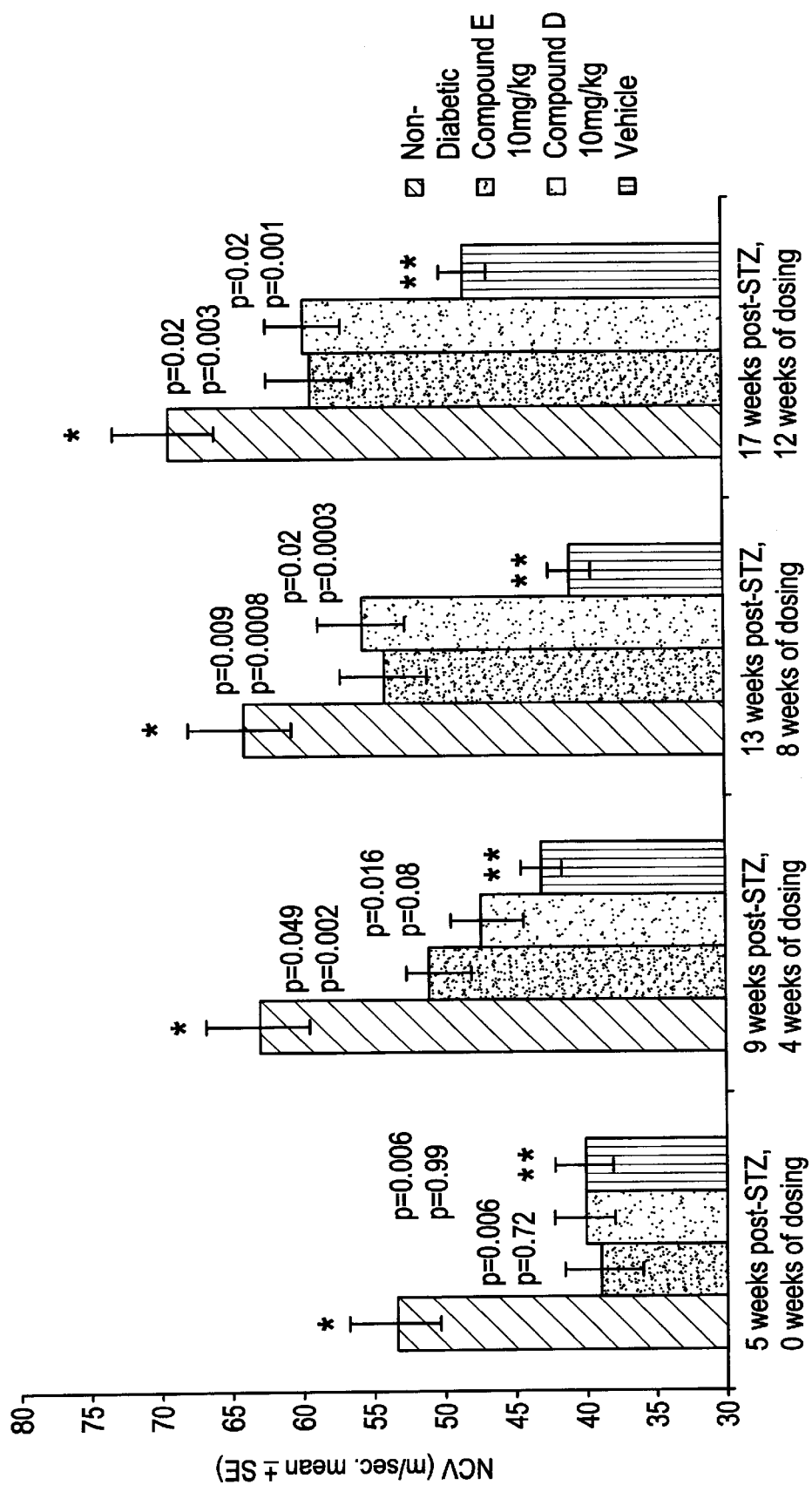
FIG. 23 shows motor nerve conduction velocity measurements in STZ diabetic rats and non-diabetic controls prior to and after treatment with Compounds D and E.

FIG. 23 shows the motor nerve conduction velocity measurements in STZ diabetic rats and non-diabetic controls prior to and at time periods after NAALADase inhibitor treatment. Within 8 weeks of dosing, both NAALADase inhibitors Compound D and Compound E reversed the motor nerve conduction velocity towards normal (non-diabetic values). This effect persisted through 12 weeks of treatment.

Figure 24:
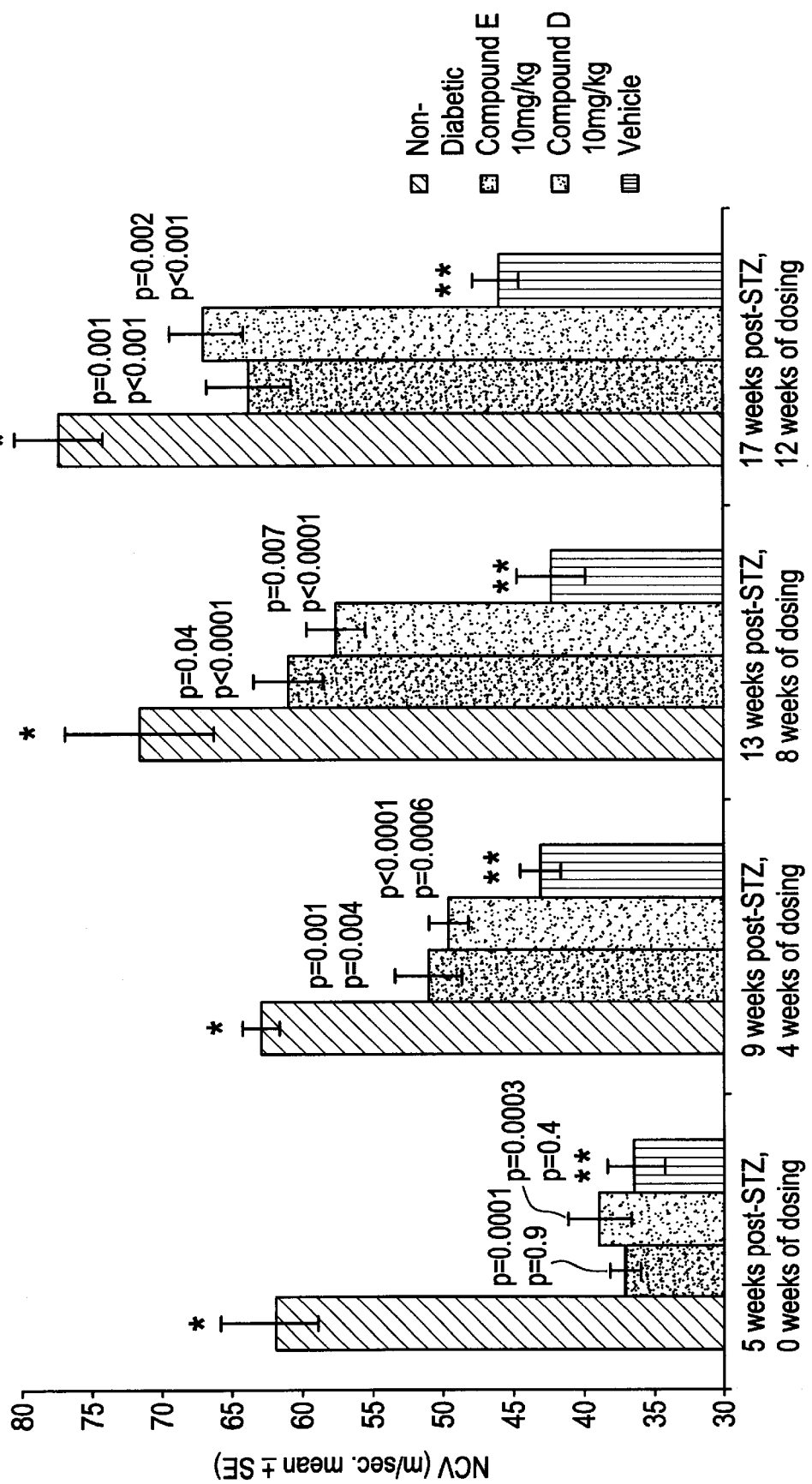
FIG. 24 depicts sensory nerve conduction velocity deficits after treatment with Compounds D and E.

FIG. 24 depicts sensory nerve conduction velocity deficits, similarly tested. NAALADAse inhibitor treatment similarly reversed sensory nerve conduction velocity deficits, significantly so after only 2 weeks of treatment.

Figure 25:
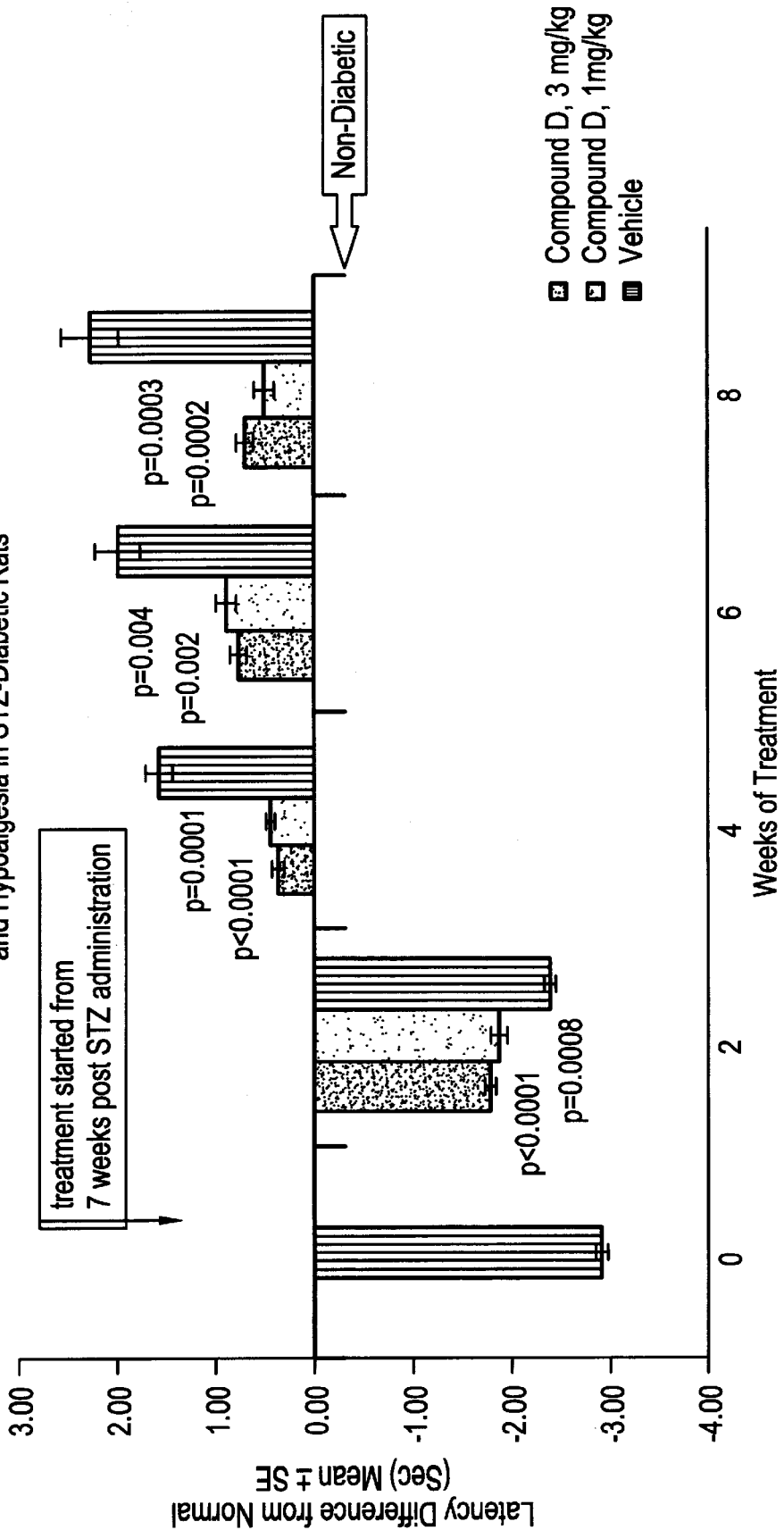
FIG. 25 shows neuropathic pain abnormalities with lower doses (1 and 3 mg/kg) of Compound D initiated after 7 weeks of STZ treatment.

FIG. 25 shows neuropathic pain abnormalities in another experiment where lower doses (1 and 3 mg/kg) of the NAALADase inhibitor Compound D initiated after 7 weeks of STZ treatment were tested. Significant reduction in pain abnormalities were again apparent with both doses of Compound D.

Figure 26:
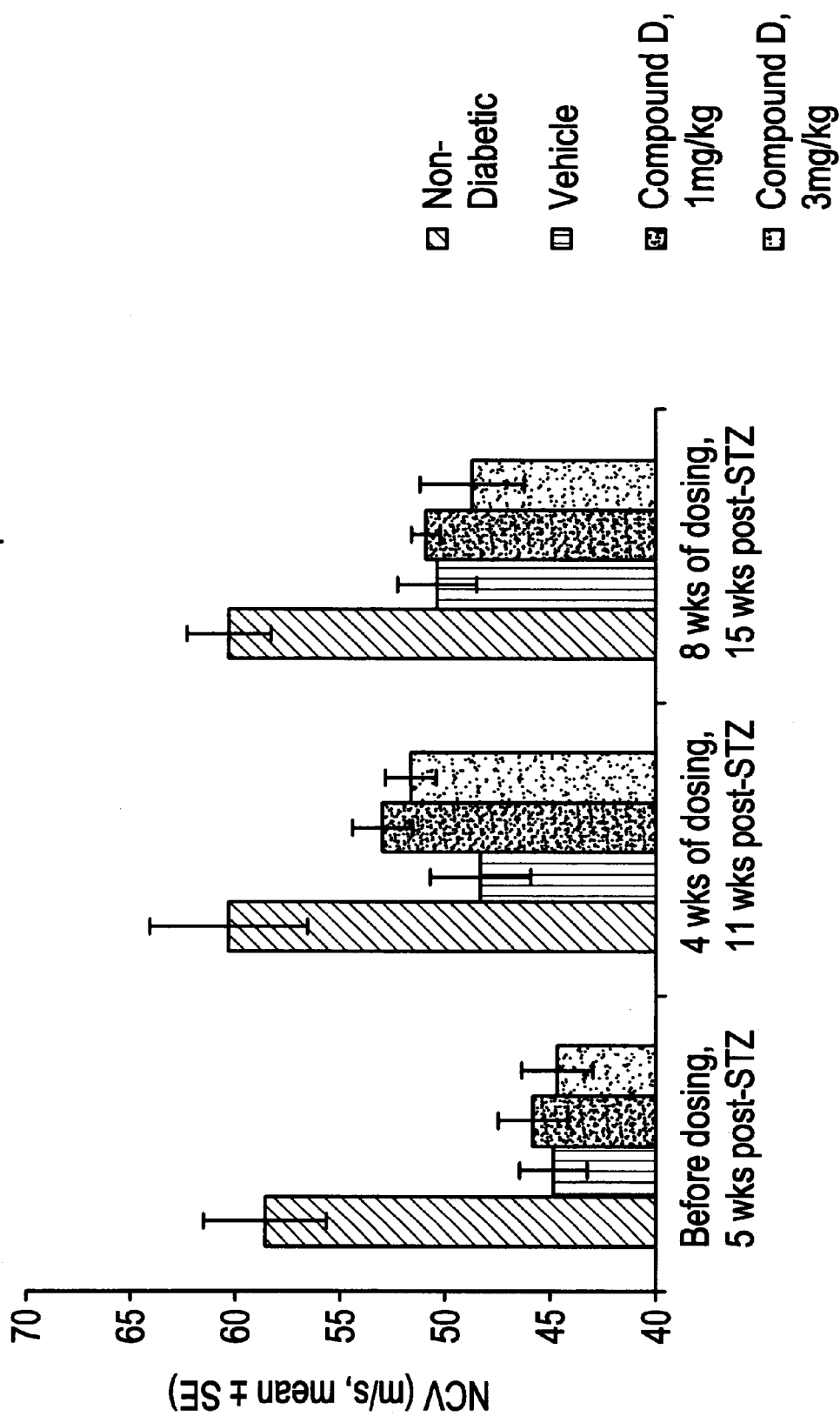
FIGS. 26 and 27 show sensory and motor nerve conduction velocity respectively in chronically diabetic STZ rats treated with lower doses of Compound D.
Figure 27:
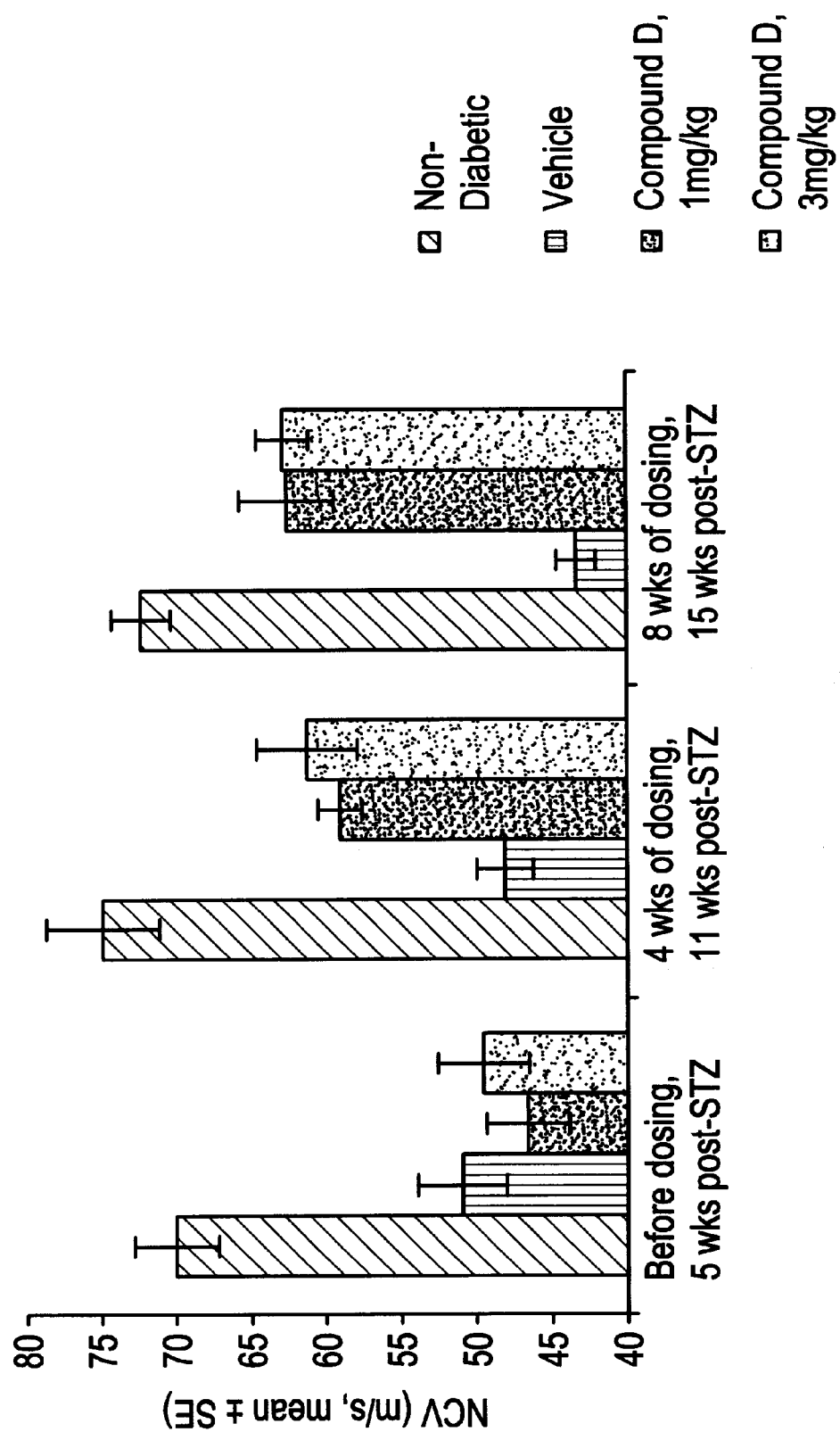

FIGS. 26 and 27 show sensory and motor nerve conduction velocity respectively in these chronically diabetic STZ rats treated with the lower doses of Compound D. Sensory nerve conduction was significantly improved towards normal within 4 weeks of treatment whereas motor nerve conduction remained unimproved by these low doses, even 8 weeks after dosing.

Figure 28:
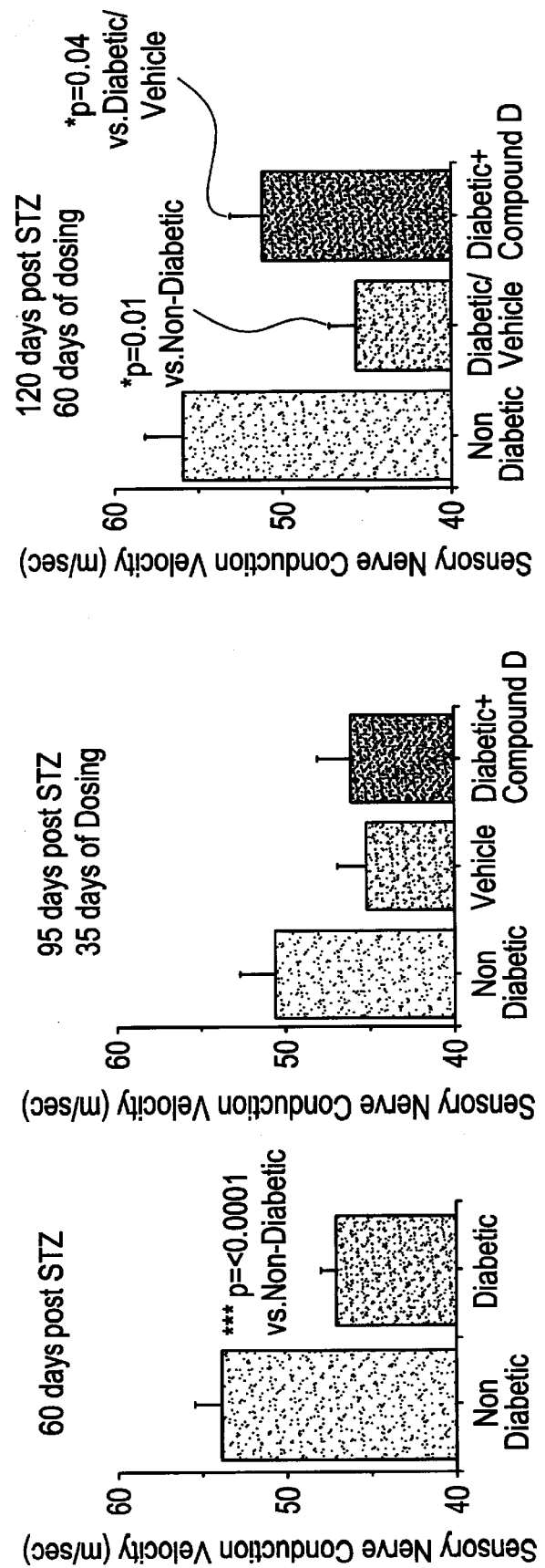
FIGS. 28 and 29 show sensory and motor nerve conduction velocity measurements where rats were left untreated until 60 days after STZ treatment.
Figure 29:
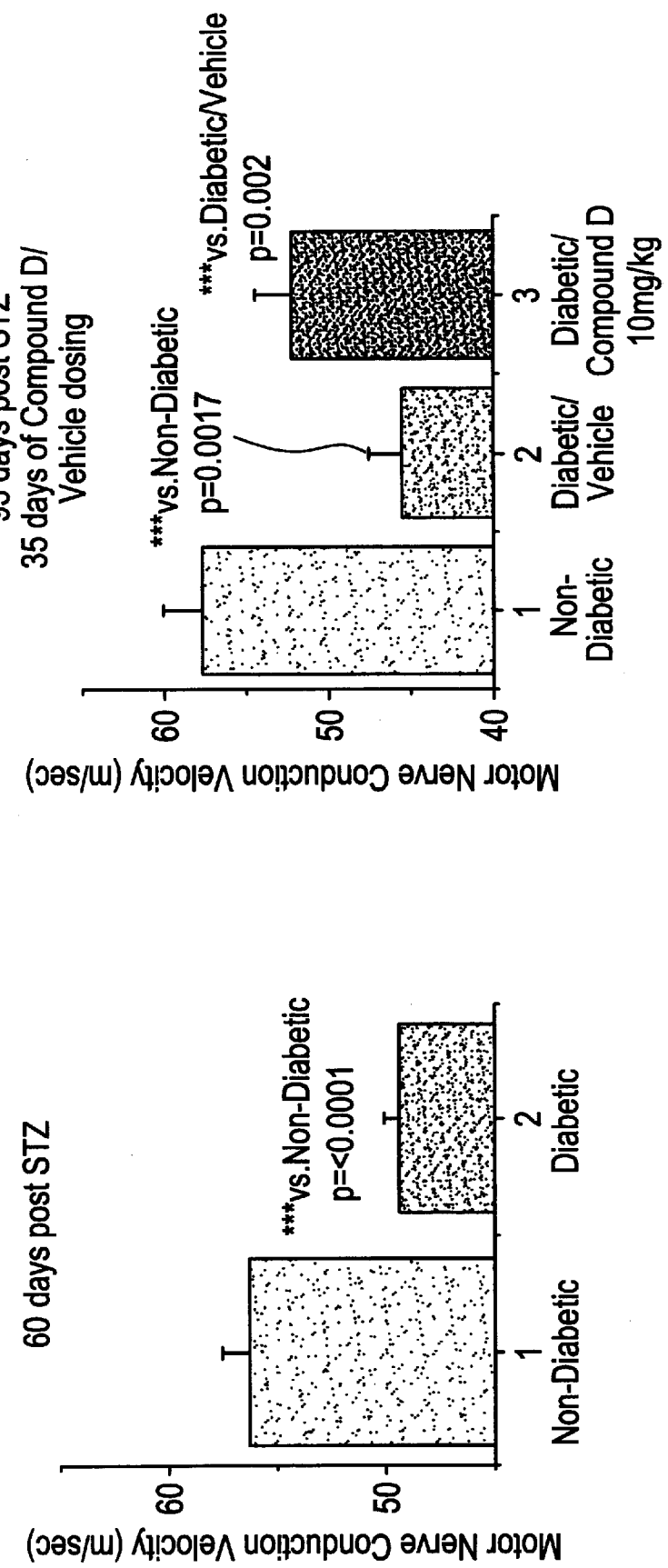
Figure 30:
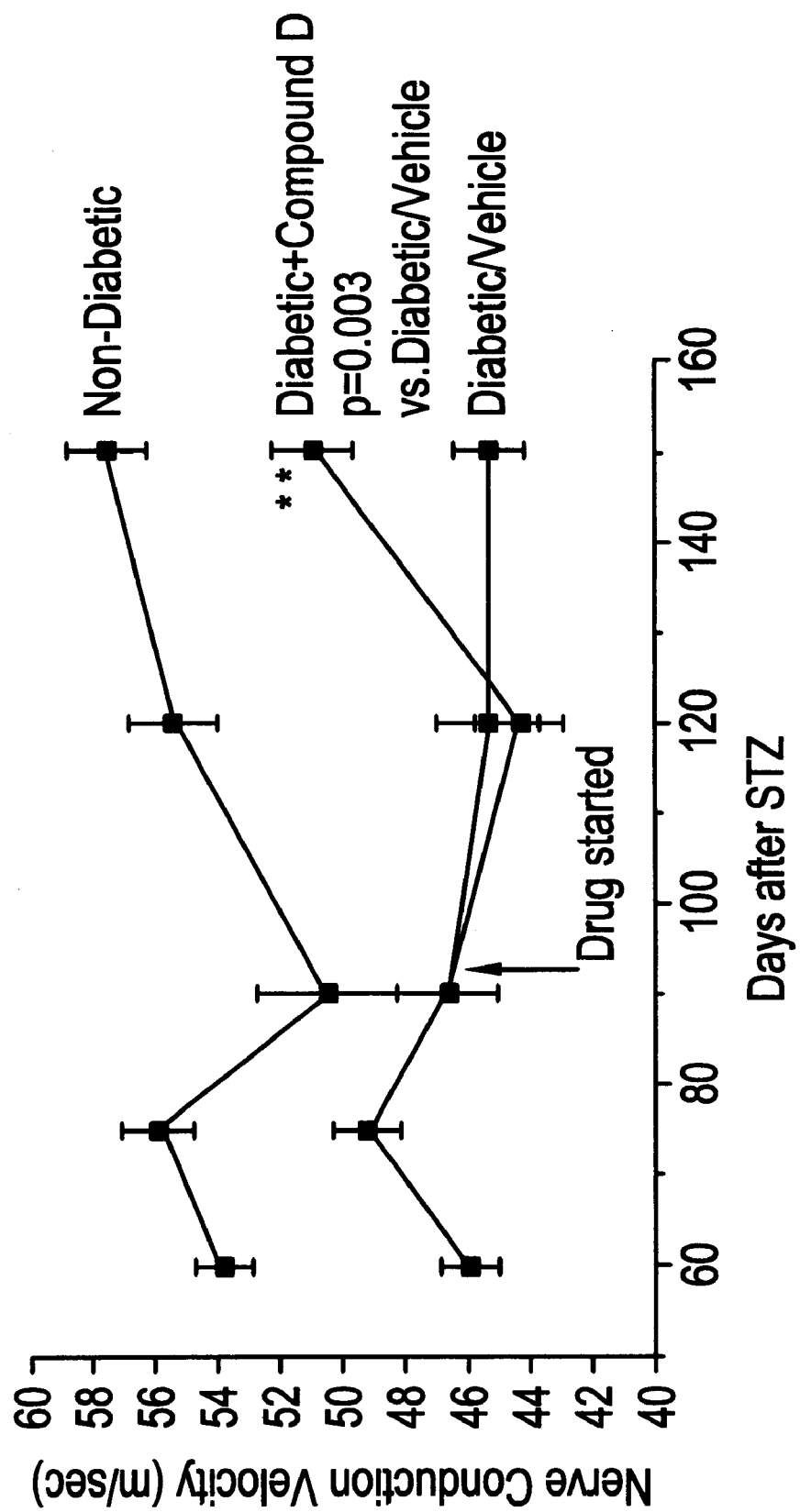
FIG. 30 shows sensory nerve conduction velocity where treatment was delayed until 90 days after STZ.

FIGS. 28 and 29 show sensory and motor nerve conduction velocity measurements generated from an external CRO in a similar chronically diabetic STZ model, where rats were left untreated until 60 days after STZ treatment. Partial reversal of both deficits was again produced by Compound D treatment. FIG. 30 shows the same where treatment was delayed yet further, until 90 days after STZ.

Figure 31:
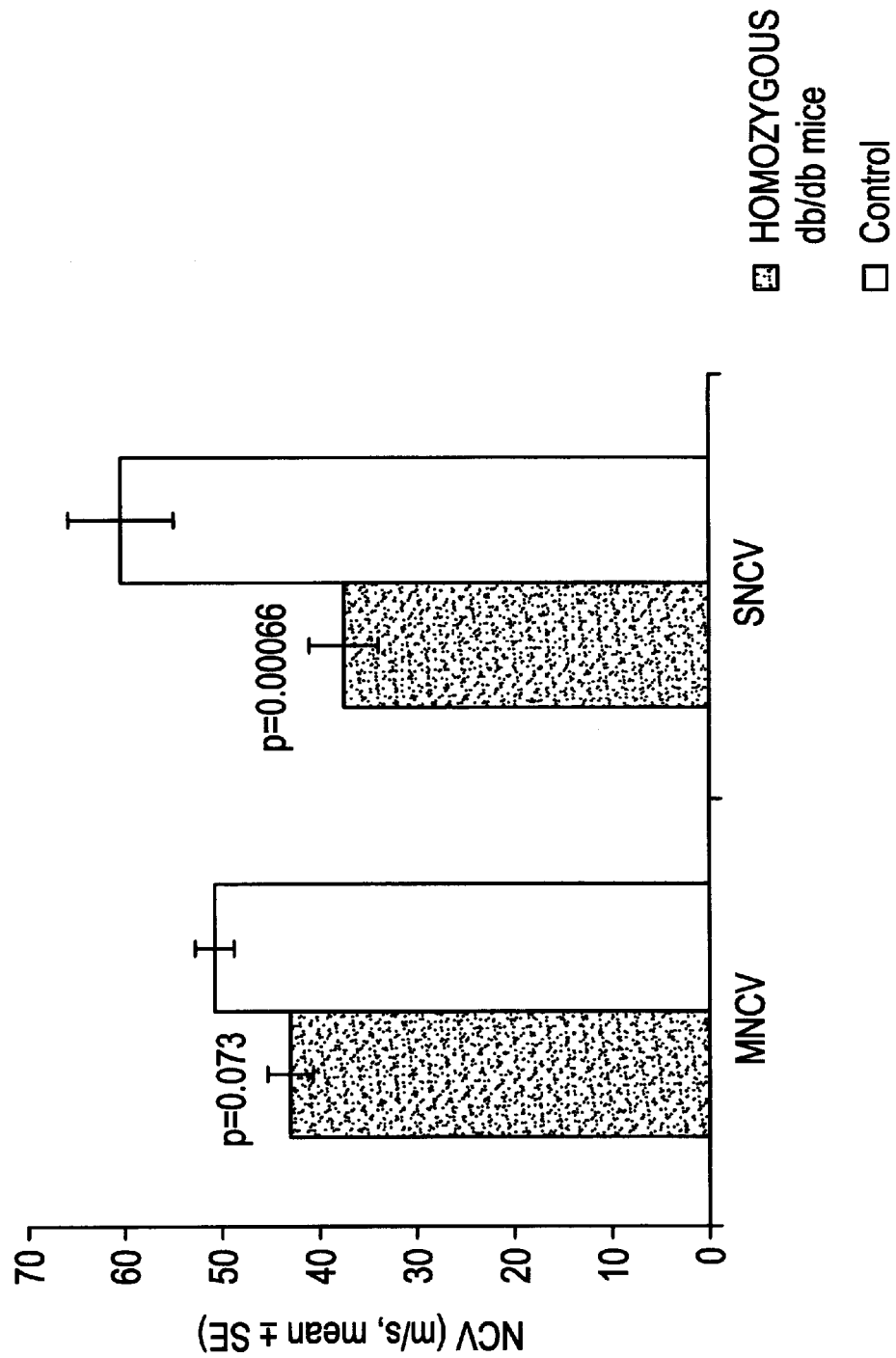
FIG. 31 shows nerve conduction velocity measurements from a genetic mouse model of diabetes, at 6–7 months of age.
Figure 32:
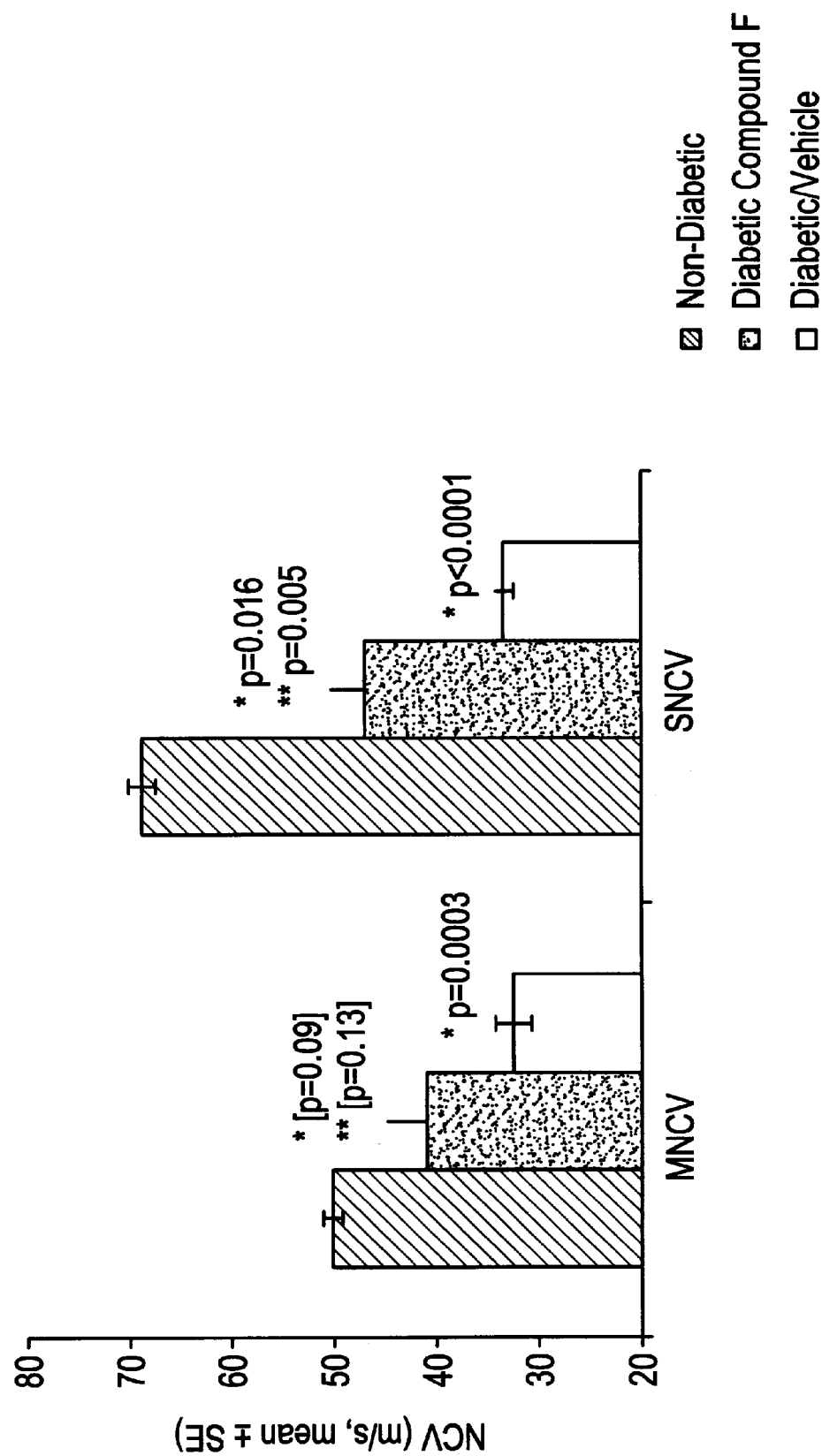
FIG. 32 shows nerve conduction velocity after 8 weeks of treatment with Compound F administered at 1 mg/kg daily.

FIG. 31 shows nerve conduction velocity measurements from a genetic mouse model of diabetes, at 6–7 months of age (after about 4 months of chronic diabetes). A significant impairment in sensory NCV was apparent at this time. FIG. 32 shows the nerve conduction velocity in these mice after 8 weeks of treatment with another, more potent NAALADase inhibitor administered at 1 mg/kg daily. Significant improvement in the sensory nerve conduction was apparent following drug treatment.

Example 12

Effect of NAALADase Inhibitors on Onset of ALS

The effect of NAALADase inhibitors on the onset of ALS was tested using the transgenic mice model of familial amyotrophic lateral sclerosis ("FALS"), which is detailed in Gurney, M., *Annals of Neurology* (1996) 39:147–157, and otherwise well known in the art. One month old transgenic G1H mice were treated with daily intraperitoneal injections of a vehicle (50 mM HEPES-buffered saline) or a NAALADase inhibitor (50 mg/kg Compound A). Clinical symptoms of the mice were monitored daily. The onset of clinical disease was scored by examining each mouse for its shaking of limbs when suspended in the air by its tail, cross spread of spinal reflexes, hindlimb paralysis, body weight and wheel running activity.

The results, set forth below in Table IV, show that disease onset was delayed in mice treated with a NAALADase inhibitor.

TABLE IV

Effect Of Naaladase Inhibitor On Onset Of Clinical Disease

| STUDY | DISEASE ONSET COMPOUND A (days) | DISEASE ONSET VEHICLE (days) | DIFFERENCE |
|---|---|---|---|
| Study 1 | 221 | 189 | 32 |
| Study 2 | 166 | 141 | 25 |

Example 13

Effect of NAALADase Inhibitor on ALS Survival and Clinical Symptoms

The effect of NAALADase inhibitors on ALS survival and clinical symptoms was tested using again the transgenic mice model of FALS. One month old transgenic G1H mice were treated daily with a vehicle (50 mM HEPES-buffered saline) or Compound B p.o. (by oral administration). Clinical symptoms of the mice were monitored twice a week. Such symptoms included shaking of limbs, gait, dragging of hind limbs, crossing of limbs, righting reflex and mortality. Gait and crossing of limbs were graded on an arbitrary scale ranging from 0 to 3, with 0 representing most normal and 3 representing least normal, e.g. severest difficulty in walking or crossing limbs. Righting reflex was measured by the time (seconds) it took the mice to right themselves when placed on their sides on a flat surface.

The results, set forth in FIGS. 15–21, show that survival was prolonged and clinical symptoms were attenuated in mice treated with a NAALADase inhibitor.

Example 14

Protective Effect of NAALADase Inhibitors in Experimental Rat Glaucoma

Experimental Protocol

All experiments complied with the Association for Research in Vision and Ophthalmology Statement for the Use of Animals in Ophthalmic and Vision Research. 82 male Brown Norway rats (Rattus norvegicus), each weighing approximately 250 gm, were treated using procedures approved by the Animal Care Committee of the Johns Hopkins University School of Medicine. The rats were housed with a 12 hour light/12 hour dark cycle and fed ad libitum.

EXPERIMENTAL GLAUCOMA: Unilateral elevation of intraocular pressure ("IOP") was produced in 56 rats by microinjection of hypertonic saline into episcleral veins, following procedures described in Morrison, J. et al., IOVS (March 1998) 39:526–531. Beginning on the day of IOP elevation, the rats were treated daily with intraperitoneal injections of either a vehicle (23 rats with 50 mM HEPES-buffered saline) or a NAALADase inhibitor (11 rats with 10 mg/kg of Compound A and 22 rats with 10 mg/kg of Compound B). 11 saline treated rats, 11 Compound A treated rats and 11 Compound B treated rats were sacrificed at 8 weeks, and the remaining rats at 12 weeks, after initial IOP elevation.

OPTIC NERVE TRANSECTION: The optic nerve was transected unilaterally in 26 rats under intraperitoneal pentobarbital anesthesia. The conjunctiva was opened with scissors and the optic nerve exposed by traction on extraocular muscles. The transection was performed with microscissors 5 mm posterior to the globe, with specific attention to avoidance of injury to major ocular blood vessels. Immediately after transection, the retina was examined ophthalmoscopically to assure that the retinal arterial blood supply was not disrupted. The conjunctiva was closed with absorbable suture and the eye dressed with antibiotic ointment. Beginning on the day of transection, the rats were treated daily with intraperitoneal injections of either a vehicle (9 rats with 50 mM HEPES-buffered saline) or a NAALADase inhibitor (8 rats with 10 mg/kg of Compound A and 9 rats with 10 mg/kg of Compound B). 5 saline treated rats, 3 Compound A treated rats, and 4 Compound B treated rats were sacrificed at 2 weeks, and the remaining rats at 4 weeks, after transection.

OPTIC NERVE COUNTING: The rats were sacrificed by exsanguination under deep pentobarbital anesthesia. They were perfused through the heart with 2% paraformaldehyde/2% glutaraldehyde in 0.1 M phosphate buffer, pH 7.2, and the eyes with attached optic nerves were removed. A cross-section of the optic nerve from both experimental (glaucoma or transection) and control eyes was removed 1.5 mm posterior to the globe, 1 mm in thickness, and post-fixed in 2% osmium tetroxide in buffer. These were processed into epoxy resin, sectioned at 1 micron and stained with toluidine blue.

The area of the optic nerve cross-section was measured by outlining its outer border at 10×magnification on an image analysis system (Universal Imaging Corp., Westchester, Pa.) with Synsys digital camera and Metamorph software. Three area measurements were taken and the mean value was determined. To measure the density and fiber diameter distributions, images were captured with a 100×phase contrast objective from 10 different areas of each nerve. These were edited to eliminate non-neural objects and the size of each axon internal to the myelin sheath (its minimum diameter) and the density of axons/square mm were calculated for each image and nerve. The mean density was multiplied by total nerve area to yield fiber number for each nerve. The total fiber number in glaucoma or transection nerves was compared to the normal, fellow eye of each rat to yield a percent loss value. The number of axons counted among the 10 images was an approximately 20% sample of the 80–90,000 axons in normal rat nerves. The person measuring axon number was masked to the protocol conducted on the nerves.

Results

EXPERIMENTAL GLAUCOMA: The mean fiber percent difference in the saline-treated, control rats was significantly lower in their glaucoma eyes compared to their normal eyes, with a mean fiber loss of 14.44±5.75% (n=11 rats; Table V) in the 8 week follow-up group, and 8.15±7.84% in the 12 week follow-up group (n=12 rats; Table VI).

By contrast, there was no significant loss of fibers in either the 8 week or 12 week NAALADase inhibitor-treated rats. The mean percent fiber loss in each NAALADase inhibitor-treated group was statistically less than the loss in the saline-treated, control groups (at 8 weeks, p=0.05 for Compound A and p=0.02 for Compound B).

TABLE V

Experimental Glaucoma Results

| 8 WEEK GROUP | N | IOP INTEGRAL DIFFERENCE[a] | FIBER NUMBER | PERCENT DIFFERENCE[b] |
|---|---|---|---|---|
| Compound A | 11 | 85 ± 37.5 | 79156 ± 2436* | −1.82 ± 2.92 |
| Compound B | 11 | 116 ± 33.2 | 80785 ± 2121** | −0.82 ± 2.97 |
| Control | 11 | 104 ± 26.4 | 68295 ± 4617 | 14.44 ± 5.75 |

[a]IOP Integral Difference = difference in intraocular pressure (IOP) exposure between glaucoma eye and normal eye in each rat (mm Hg - days).
[b]Percent Difference = mean percent difference in fiber number between glaucoma and normal eye in each rat (positive value indicates fewer fibers in the glaucoma eye).

TABLE VI

Experimental Glaucoma Results

| 12 WEEK GROUP | N | IOP INTEGRAL DIFFERENCE[a] | FIBER NUMBER | PERCENT DIFFERENCE[b] |
|---|---|---|---|---|
| Compound B | 11 | 109 ± 45.2 | 90504 ± 1718 | −3.21 ± 2.86 |
| Control | 12 | 158 ± 66.5 | 79827 ± 6783 | 8.15 ± 7.84 |

[a]IOP Integral Difference = difference in intraocular pressure (IOP) exposure between glaucoma eye and normal eye in each rat (mm Hg - days).
[b]Percent Difference = mean percent difference in fiber number between glaucoma and normal eye in each rat (positive value indicates fewer fibers in the glaucoma eye).

Differences in IOP Integral Difference are not significant (p>0.05). Differences in Percent Difference between drug-treated and saline-treated, control rats at 8 weeks post insult are significant (p=0.05* and p=0.02**).

OPTIC NERVE TRANSECTION: The experimental transection data suggest a slowing or rescue of ultimate RGC death in rats treated with NAALADase inhibitors at 2 weeks after transection. At 2 weeks after transection, both drug-treated groups had more remaining RGC axons than did the saline-treated, control group, judged either by absolute number of fibers or percent difference between transected eye and normal eye in each rat (Table VII). Rats treated with Compound A and Compound B had, respectively, 3 times and twice as many remaining axons as the saline-treated rats. All or nearly all RGC die within the first 2 months after transection, regardless of any pharmacological treatment. Thus, by 4 weeks after transection, more than 80% of RGC axons were gone in all groups (Table VII). At 4 weeks after transection, there were no significant differences between the drug-treated rats and the saline-treated rats.

TABLE VII

Optic Nerve Transection

| 2 WEEKS SURVIVAL | N | FIBER NUMBER | PERCENT DIFFERENCE[a] |
|---|---|---|---|
| Compound A | 3 | 26,426 ± 23,025 | 65.3 ± 30.9 |
| Compound B | 4 | 19,550 ± 11,383 | 75.3 ± 14.8 |
| Control | 5 | 8,220 ± 9,337 | 90.2 ± 10.7 |

[a]Percent Difference = mean percent difference in fiber number between glaucoma and normal eye in each rat (positive value indicates fewer fibers in the glaucoma eye).

TABLE VIII

Optic Nerve Transection

| 4 WEEKS SURVIVAL | N | FIBER NUMBER | PERCENT DIFFERENCE[a] |
|---|---|---|---|
| Compound A | 5 | 13,599 ± 7,868 | 82.4 ± 8.9 |
| Compound B | 5 | 5,162 ± 5,017 | 93.4 ± 6.2 |
| Control | 4 | 10,449 ± 8,157 | 86.9 ± 10.6 |

[a]Percent Difference = mean percent difference in fiber number between glaucoma and normal eye in each rat (positive value indicates fewer fibers in the glaucoma eye).

Differences in Percent Difference between drug-treated and saline-treated, control rats are not statistically significant (p=0.05).

Example 15

Neuroprotective Effect of NAALADase Inhibitors in Transgenic Mouse Model of Huntington's Disease Behavioral Testing (Rotarod)

Figure 33:
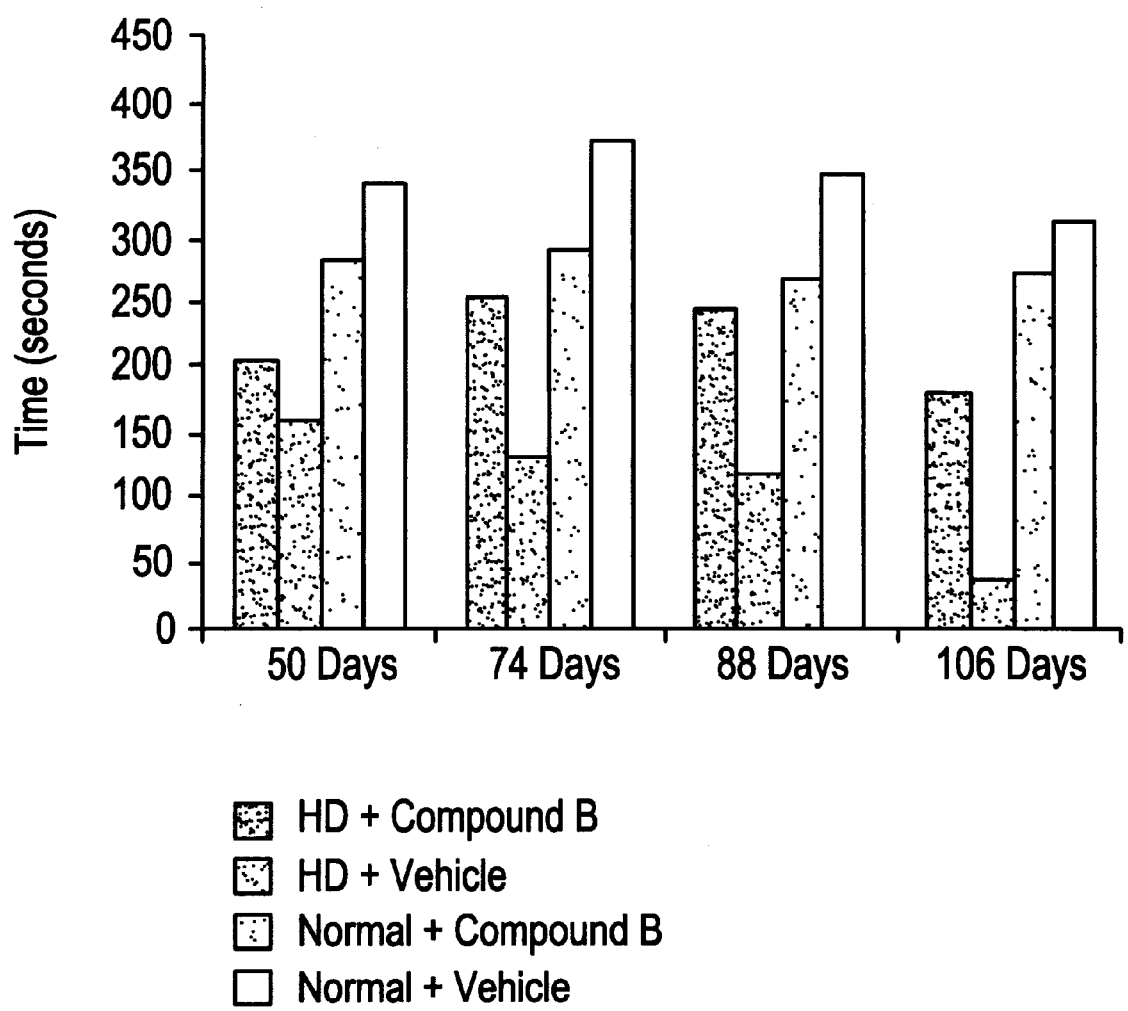
FIG. 33 is bar graph comparing the rotarod performance of transgenic HD mice and normal non-HD mice treated with Compound B, and transgenic HD mice and normal non-HD mice treated with a vehicle.

Transgenic HD mice of the N171-82Q strain and non-transgenic littermates were treated with NAALADase inhibitor Compound B (30 mg/kg) or a vehicle from 10 weeks of age. The mice were placed on a rotating rod ("rotarod"). The length of time at which the mouse fell off the rotarod was recorded as a measure of motor coordination. FIG. 33 shows that transgenic HD mice treated with Compound B stayed longer on the rotarod than similar transgenic HD mice treated with a vehicle. The treatment with Compound B had no effect on the rotarod performance of normal non-HD mice.

Figure 34:
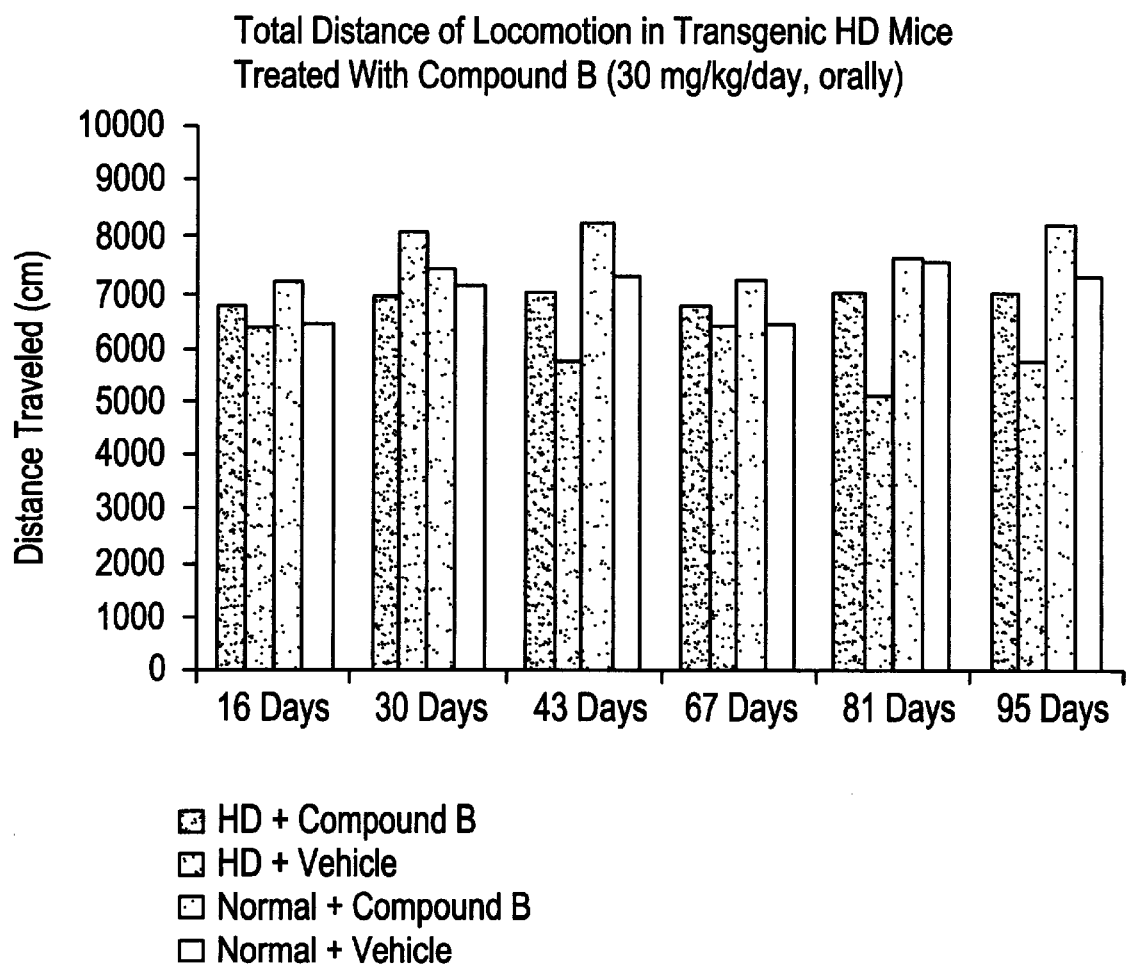
FIG. 34 is a bar graph comparing the total distance traveled by transgenic HD mice and normal non-HD mice treated with Compound B, and transgenic HD mice and normal non-HD mice treated with a vehicle.

The total distance traveled by the mice was also recorded as a measure of overall locomotion. FIG. 34 shows that while the vehicle treated HD mice demonstrated the lowest mean locomotor score, the treatment with NAALADase inhibitor had no apparent effect on overall locomotion.

Survival

The effects of Compound B and vehicle on the survival of transgenic HD mice (N171-82Q) were evaluated. Thirteen mice (six male and seven female) were assigned to the Compound B treatment group, and fourteen mice (six male and eight female) were assigned to the vehicle treatment group. Treatment was continued until all the mice died.

Figure 35:
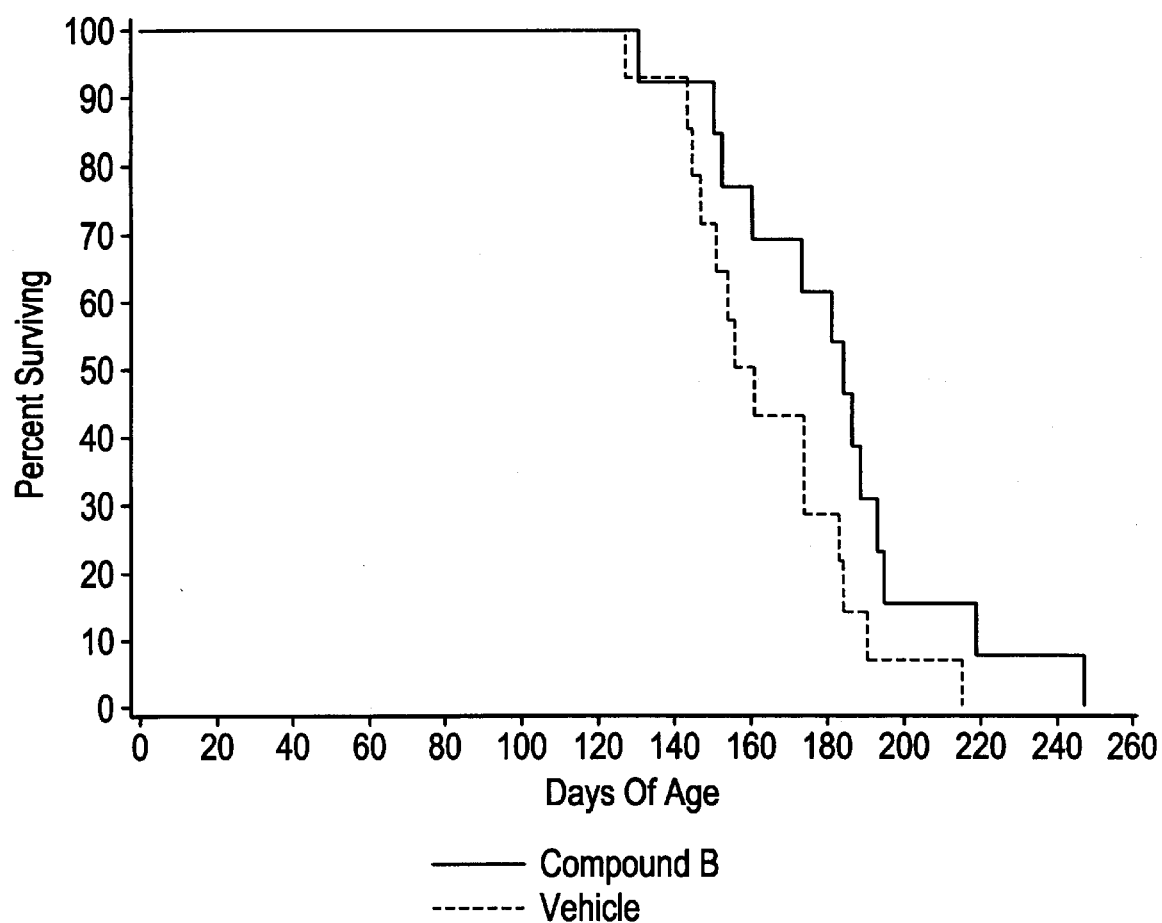
FIG. 35 is a graph plotting the survival time of transgenic D mice treated with Compound B or a vehicle.

FIG. 35 shows the survival distributions over time by treatment group. The median survival time is 184 days for the Compound B treatment group, and 158.5 days for the vehicle treatment group. Although the Compound B treatment group had a longer median survival time than the vehicle treatment group, the difference is not statistically significant (p-value=0.07).

Figure 36:
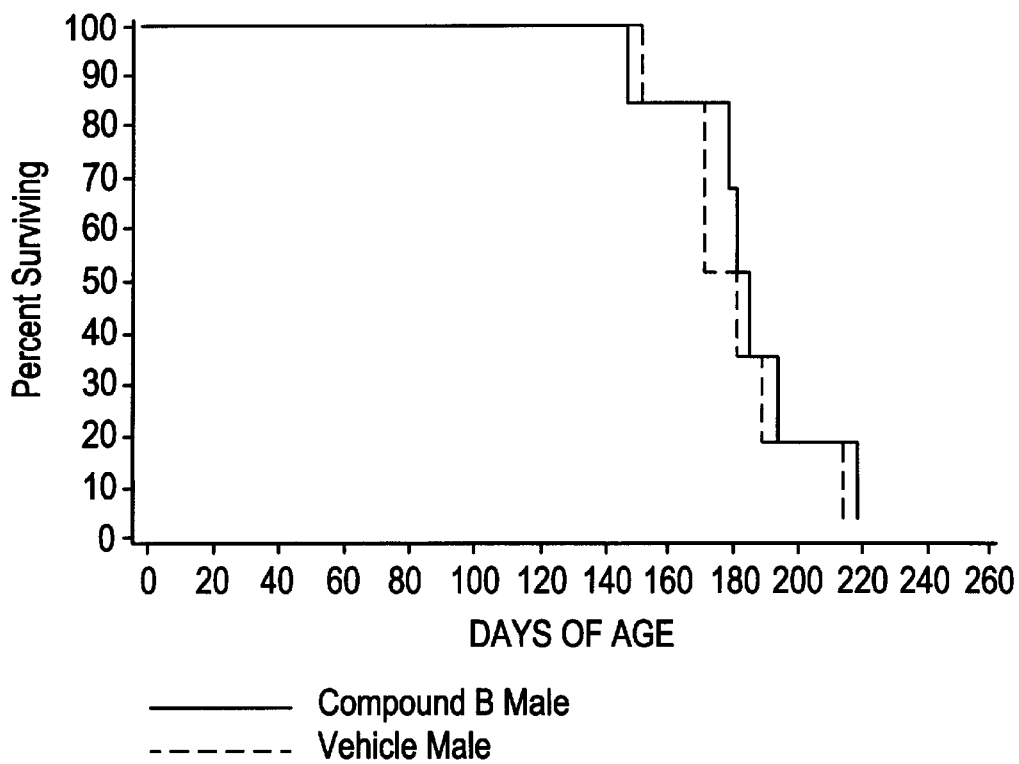
FIG. 36 is a graph plotting the survival time of male transgenic HD mice treated with Compound B or a vehicle.
Figure 37:
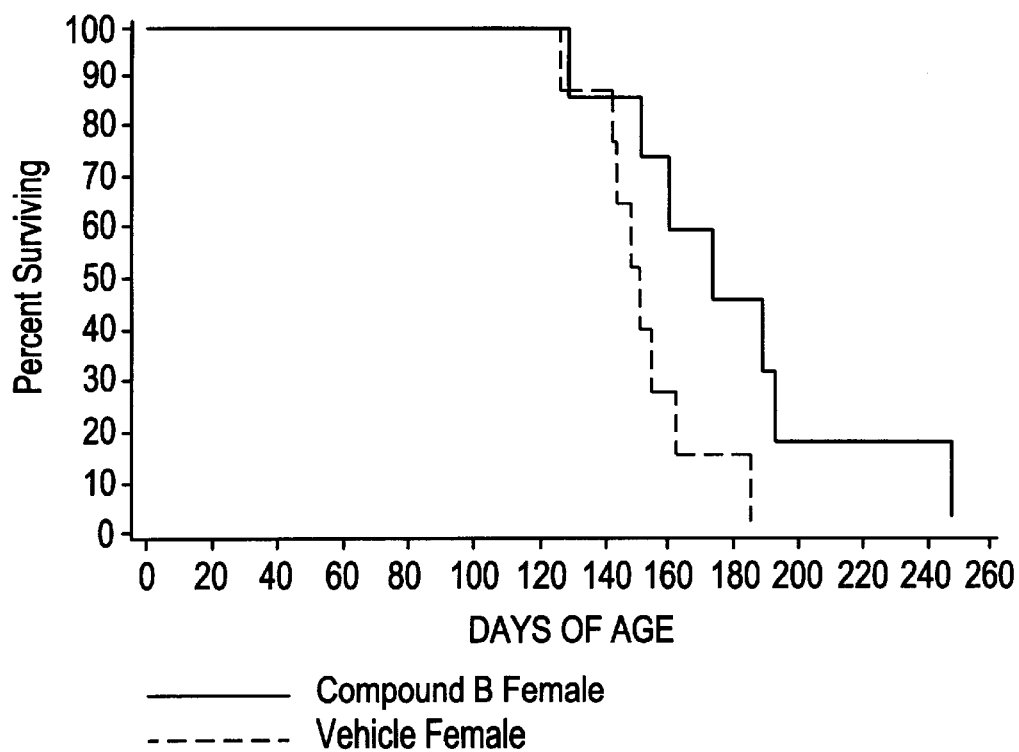
FIG. 37 is a graph plotting the survival time of female transgenic HD mice treated with Compound B or a vehicle.

FIGS. 36 and 37 show the survival distributions over time by treatment group and sex. When analyzing the results specific to sex, female mice treated with Compound B had significantly prolonged survival time (p-value=0.03) compared to their vehicle treated counterparts. Within the vehicle treatment group, the males have better survival times than the females although this trend was not observed in the Compound B treatment group. The data suggest that sex may influence survival distributions over time.

Example 16

A patient is suffering from any disease, disorder, or condition where NAALADase levels are altered, including any of the diseases, disorders, or conditions described above. The patient may then be administered an effective amount of a compound of the invention. It is expected that after such treatment, the patient would not suffer any significant injury due to, would be protected from further injury due to, or would recover from the disease, disorder or condition.

All publications, patents and patent applications identified above are herein incorporated by reference, as though set forth herein in full.

The invention being thus described, it will be apparent to those skilled in the art that the same may be varied in many ways without departing from the spirit and scope of the invention. Such variations are included within the scope of the following claims.

We claim:

1. A compound of formula Ia or a pharmaceutically acceptable equivalent:

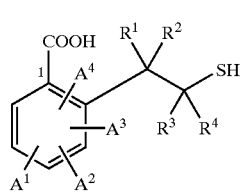

Ia wherein:

$R^1$, $R^2$, $R^3$, and $R^4$ are independently hydrogen or $C_1$–$C_3$ alkyl; and $A^1$, $A^2$, $A^3$, and $A^4$ are independently hydrogen, $C_1$–$C_9$ alkyl, $C_2$–$C_9$ alkenyl, $C_2$–$C_9$ alkynyl, aryl, heteroaryl, carbocycle, heterocycle, halo, hydroxy, sulfhydryl, nitro, amino, cyano, isocyano, thiocyano, isothiocyano, formamido, thioformamido, sulfo, sulfino, $C_1$–$C_9$ alkylsulfonyl, $C_1$–$C_9$ alkoxy, $C_2$–$C_9$ alkenoxy, phenoxy, or benzyloxy, le;.5qwherein said alkyl, alkenyl, alkynyl, aryl, heteroaryl, carbocycle, heterocycle, alkoxy, alkenoxy, phenoxy, and benzyloxy are independently unsubstituted or substituted with one or more substituent(s).

2. A compound according to claim 1 wherein:

$R^1$, $R^2$, $R^3$, $R^4$, $A^2$, $A^3$, and $A^4$ are hydrogen; and $A^1$ is hydrogen, —$(CH_2)_n$-W, or —Y—$(CH_2)_n$-W, wherein: n is 0–3; Y is O, S, or NR wherein R is hydrogen or C1 –C4 alkyl; and W is C1–C6 alkyl or phenyl, wherein W is unsubstituted or substituted with C1–C4 alkyl, C1–C4 alkoxy, carboxy, or halo.

3. A compound according to claim 2, wherein the compound is an enantiomer or part of an enantiomer-enriched mixture.

4. A compound according to claim 2 wherein:

$A^1$ is —$(CH_2)_n$-W, or —Y—$(CH_2)_n$—W, n is 1 or 2, and

Y is O.

5. A compound according to claim 2 wherein the compound is:

2-(2-mercaptoethyl)-benzoic acid;

5-[(4-carboxyphenyl)methoxy]-2-(2-mercaptoethyl)-benzoic acid;

2-(2-mercaptoethyl)-5-(phenylmethoxy)-benzoic acid;
2-(carboxymethoxy)-6-(2-mercaptoethyl)-benzoic acid;
5-[(3-carboxyphenyl)methoxy]-2-(2-mercaptoethyl)-benzoic acid;
2-(2-mercaptoethyl)-6-(phenylmethoxy)-benzoic acid;
2-[(2-carboxyphenyl)methoxy]-6-(2-mercaptoethyl)-benzoic acid;
2-[(4-carboxyphenyl)methoxy]-6-(2-mercaptoethyl)-benzoic acid;
3-(2-mercaptoethyl)-[1,1'-biphenyl]-2,3'-dicarboxylic acid;
2-(3,3-dimethylbutoxy)-6-(2-mercaptoethyl)-benzoic acid;
2-(2-mercaptoethyl)-6-(2-phenylethoxy)-benzoic acid;
2-[(2-chlorophenyl)methoxy]-6-(2-mercaptoethyl)-benzoic acid;
2-[[3 carboxy-5-(1,1-dimethylethyl)phenyl]methoxy]-6-(2-mercaptoethyl)-benzoic acid;
3-(2-mercaptoethyl)-[1,1'-biphenyl]-2,4'-dicarboxylic acid;
2-[(4-carboxy-2-methoxyphenyl)methoxy]-6-(2-mercaptoethyl)-benzoic acid;
2-[(4-carboxy-3-methoxyphenyl)methoxy]-6-(2-mercaptoethyl)-benzoic acid;
2-[(2-bromo-4-carboxyphenyl)methoxy]-6-(2-mercaptoethyl)-benzoic acid;
2-[(3-bromo-4-carboxyphenyl)methoxy]-6-(2-mercaptoethyl)-benzoic acid;
2-(2-mercaptoethyl)-6-phenoxy-benzoic acid;
2-(2-mercaptoethyl)-6-phenylamino-benzoic acid;
2-(2-mercaptoethyl)-6-(phenylthio)-benzoic acid;
5'-(1,1-dimethylethyl)-3-(2-mercaptoethyl)-[1,1'-biphenyl]-2,3'-dicarboxylic acid;
2-[(4-chlorophenyl)methoxy]-6-(2-mercaptoethyl)-benzoic acid;
2-(biphenyl-2-ylmethoxy)-6-(2-mercaptoethyl)-benzoic acid;
2-[(3-bromo-5-carboxyphenyl) methoxy]-6-(2-mercaptoethyl)-benzoic acid;
2-[(2-bromo-5-carboxyphenyl) methoxy]-6-(2-mercaptoethyl)-benzoic acid;
2-(2-mercaptoethyl)-6-[(4-methoxyphenyl)methoxy]-benzoic acid;
2-(2-mercaptoethyl)-6-[(4-methylphenyl)methoxy]-benzoic acid;
2-[(4-bromo-3-carboxyphenyl) methoxy]-6-(2-mercaptoethyl)-benzoic acid;
2-[(2-carboxy-5-methoxyphenyl) methoxy]-6-(2-mercaptoethyl)-benzoic acid;
2-(3-carboxy-benzyloxy)-6-(2-mercapto-ethyl)-benzoic acid;
2-(4-bromo-benzyloxy)-6-(2-mercapto-ethyl)-benzoic acid;
2-(4-tert-butyl-benzyloxy)-6-(2-mercapto-ethyl)-benzoic acid;
2-(3-bromo-benzyloxy)-6-(2-mercapto-ethyl)-benzoic acid;
2-(2-mercapto-ethyl)-6-methoxy-benzoic acid;
2-(3-chloro-benzyloxy)-6-(2-mercapto-ethyl)-benzoic acid;
3-(2-mercapto-ethyl)-biphenyl-2-carboxylic acid; or
2-carboxymethyl-6-(2-mercapto-ethyl)-benzoic acid; or a pharmaceutically acceptable salt thereof.

6. A compound according to claim 5 wherein the compound is:
2-(2-mercaptoethyl)-6-(phenylmethoxy)-benzoic acid;
3-(2-mercaptoethyl)-[1,1'-biphenyl]-2,3'-dicarboxylic acid; or 2-carboxymethyl-6-(2-mercapto-ethyl)-benzoic acid; or a pharmaceutically acceptable salt thereof.

7. A method for inhibiting NAALADase enzyme activity, treating a glutamate abnormality, effecting a neuronal activity, treating a prostate disease, treating cancer, inhibiting angiogenesis or effecting a TGF-β activity, comprising administering to a mammal in need of such inhibition, treatment or effect, an effective amount of a compound of claim 1.

8. The method of claim 7, wherein said method is for treating a glutamate abnormality selected from the group consisting of a compulsive disorder, stroke, demyelinating disease, schizophrenia, Parkinson's disease, amyotrophic lateral sclerosis, anxiety, anxiety disorder, memory impairment and glaucoma.

9. The method of claim 7, wherein said method is for effecting a neuronal activity selected from the group consisting of stimulation of damaged neurons, promotion of neuronal regeneration, prevention of neurodegeneration and treatment of a neurological disorder.

10. The method of claim 9, wherein the neuronal activity is treatment of a neurological disorder and said neurological disorder is pain, diabetic neuropathy, peripheral neuropathy caused by physical injury or disease state, traumatic brain injury, physical damage to spinal cord, stroke associated with brain damage, a demyelinating disease or a neurological disorder relating to neurodegeneration.

11. The method of claim 7, wherein said method is for treating cancer.

12. The method of claim 7, wherein said method is for inhibiting angiogenesis.

13. The method of claim 7, wherein said method is for treating a TGF-β abnormality selected from the group consisting of neurodegenerative disorder, extra-cellular matrix formation disorder, cell-growth related disease, infectious disease, immune related disease, epithelial tissue scarring, collagen vascular disease, fibroproliferative disorder, connective tissue disorder, inflammation, inflammatory disease, respiratory distress syndrome, infertility, and diabetes.

14. A method for detecting a disease, disorder or condition where NAALALDase levels are altered, comprising:
(i) contacting a sample of bodily tissue or fluid with a compound according to claim 1, wherein said compound binds to any NAALADase in said sample; and
(ii) measuring the amount of any NAALADase bound to said sample, wherein the amount of NAALADase is diagnostic for said disease, disorder, or condition.

15. A method for detecting a disease, disorder or condition where NAALADase levels are altered, comprising:
(i) labeling a compound according to claim 1, with an imaging reagent;
(ii) administering to an animal or mammal an effective amount of the labeled compound;
(iii) allowing said labeled compound to localize and bind to NAALADase present in said animal or mammal; and
(iv) measuring the amount of NAALADase bound to said labeled compound, wherein the amount of NAALADase is diagnostic for said disease, disorder, or condition.

16. A diagnostic kit for detecting a disease, disorder, or condition where NAALADase levels are altered, comprising a compound according to claim 1 labeled with a marker.

17. A pharmaceutical composition comprising:
(i) an effective amount of a compound according to claim 1; and
(ii) a pharmaceutically acceptable carrier.

* * * * *

UNITED STATES PATENT AND TRADEMARK OFFICE
CERTIFICATE OF CORRECTION

| | |
|---|---|
| PATENT NO. | : 6,740,777 B2 |
| APPLICATION NO. | : 10/156880 |
| DATED | : May 25, 2004 |
| INVENTOR(S) | : Takashi Tsukamoto et al. |

It is certified that error appears in the above-identified patent and that said Letters Patent is hereby corrected as shown below:

Col. 68, line 45, change "le;.5qwherein" to --wherein--.

Signed and Sealed this

Fifteenth Day of September, 2009

David J. Kappos
*Director of the United States Patent and Trademark Office*